（12） United States Patent
Yin et al.

(10) Patent No.: US 10,851,130 B2
(45) Date of Patent: Dec. 1, 2020

(54) **CHEMICAL SYNTHESIS METHOD OF *PLESIOMONAS SHIGELLOIDES* SEROTYPE O51 O-ANTIGEN OLIGOSACCHARIDE**

(71) Applicants: Jiangnan University, Wuxi (CN); Max Planck Institute of Colloids and Interfaces, Potsdam (DE)

(72) Inventors: Jian Yin, Wuxi (CN); Jing Hu, Wuxi (CN); Peter Seeberger, Potsdam (DE); Chunjun Qin, Wuxi (CN)

(73) Assignees: Jiangnan University, Wuxi (CN); Max Planck Institute of Colloids and Interfaces, Potsdam (DE)

( * ) Notice: Subject to any disclaimer, the term of this patent is extended or adjusted under 35 U.S.C. 154(b) by 0 days.

(21) Appl. No.: 16/215,349

(22) Filed: Dec. 10, 2018

(65) Prior Publication Data

US 2019/0233459 A1    Aug. 1, 2019

Related U.S. Application Data

(63) Continuation of application No. PCT/CN2018/082660, filed on Apr. 11, 2018.

(30) Foreign Application Priority Data

Jan. 29, 2018  (CN) .......................... 2018 1 0083471

(51) Int. Cl.
| | |
|---|---|
| *C07H 15/04* | (2006.01) |
| *C07H 15/06* | (2006.01) |
| *C07H 15/12* | (2006.01) |
| *C07H 1/00* | (2006.01) |
| *A61P 31/04* | (2006.01) |
| *C07H 13/04* | (2006.01) |
| *A61K 39/02* | (2006.01) |
| *A61K 39/112* | (2006.01) |

(52) U.S. Cl.
CPC .......... *C07H 15/12* (2013.01); *A61K 39/025* (2013.01); *A61K 39/0208* (2013.01); *A61P 31/04* (2018.01); *C07H 1/00* (2013.01); *C07H 13/04* (2013.01); *C07H 15/04* (2013.01); *C07H 15/06* (2013.01); *A61K 39/0283* (2013.01)

(58) Field of Classification Search
None
See application file for complete search history.

(56) References Cited

PUBLICATIONS

Kilcoyne et al., "The structure of the O-polysaccharide of the Pseudoalteromonas rubra ATCC 29570T lipopolysaccharide containing a keto sugar" Carbohydrate Research vol. 340 pp. 2369-2375 (Year: 2005).*
Nazarenko et al., "The Structural Diversity of Carbohydrate Antigens of Selected Gram-Negative Marine Bacteria" Marine Drugs vol. 9 pp. 1914-1954 (Year: 2011).*
Chunjun Qin, et al., Total Synthesis of a Densely Functionalized Plesiomonas shigelloides Serotype 51 Aminoglycoside Trisaccharide Antigen J. Am. Chem. Soc. Jan. 29, 2018 (Jan. 29, 2018), No. 8, vol. 140, p. 3120-3127.
A. Maciejewska, et al., Structural analysis of the O-specific polysaccharide isolated from Plesiomonas shigelloides O51 lipopolysaccharide. Carbohydr Res May 12, 2009 (May 12, 2009), No. 7, vol. 344, p. 894-900.

* cited by examiner

*Primary Examiner* — Eric Olson
(74) *Attorney, Agent, or Firm* — IPro, PLLC

(57) ABSTRACT

The present disclosure discloses the chemical synthesis method of the *Plesiomonas shigelloides* serotype O51 O-antigen oligosaccharide, belonging to the field of chemistry. Source-abundant D-glucose, L-fucose, D-glucosamine and the like are used as raw materials to prepare three glycosylation building blocks, the synthetic route composed of 11 reaction modules is designed, and through the optimization of protecting group and the optimization of the time of introducing functional group, the preparation of the target oligosaccharide chain is successfully achieved. The oligosaccharide chain prepared in the present disclosure has the advantages of cheap and easy-to-get raw materials, and simple and easy-to-repeat preparation method. The present disclosure will have good application prospects in the aspects of development of new drugs and vaccines of *Plesiomonas shigelloides*, and the like.

15 Claims, 23 Drawing Sheets

CHEMICAL SYNTHESIS METHOD OF *PLESIOMONAS SHIGELLOIDES* SEROTYPE O51 O-ANTIGEN OLIGOSACCHARIDE

TECHNICAL FIELD

The present disclosure relates to a chemical synthesis method of *Plesiomonas shigelloides* serotype O51 O-antigen oligosaccharide, and more particularly relates to a hetero-modified polyaminooligosaccharide assembled with an amino linker at the reducing end, belonging to the field of chemistry.

BACKGROUND

*Plesiomonas shigelloides* is a Gram-negative pathogen discovered in 1947 and is the most important pathogen causing worldwide travelers' severe diarrhea. In addition, *Plesiomonas shigelloides* may cause a series of serious extraintestinal infections, and especially can infect children and adults with underlying diseases, wherein sepsis and meningitis caused by infection with *Plesiomonas shigelloides* have a very high lethality rate (I. Stock, *Rev. Med. Microbiol.* 2004, 15, 129-139). At present, the treatment of this pathogen infection relies on antibiotic treatment, and the continuous emergence of drug resistance reports in clinical treatment makes the treatment of *Plesiomonas shigelloides* infections more difficult. What is worrying is that there are no *Plesiomonas shigelloides* vaccines that have been registered for listing in the world. As international exchanges become increasingly close, it is particularly urgent to develop an effective *Plesiomonas shigelloides* vaccine.

The study on the serotype of *Plesiomonas shigelloides* shows that it has 102 somatic antigens (O-antigens) and 51 flagella antigens (H-antigens) (E. Aldova et al., *Folia Microbiol.* 2000, 45, 301-304). Since *Plesiomonas shigelloides* is a non-capsule-producing bacterium, its cell surface is wrapped by a lipopolysaccharide (LPS) layer. Since the O-antigen portion of LPS of the bacterium has high structural specificity, and plays an important role in biological processes such as pathogen infection and host immune response (J. Lukasiewicz et al., *Biochemistry* 2006, 45, 10434-10447), the O-antigen of *Plesiomonas shigelloides* is an important target molecule for the development of the *Plesiomonas shigelloides* vaccine.

Among many reported structures of the *Plesiomonas shigelloides* O-antigen, the 0-antigen polysaccharide structure of the serotype O51 has attracted attention because of its high structural specificity. The polysaccharide structure consists of a hetero-modified polyamino trisaccharide repeat unit: [→4)-β-D-GlcpNAc3NHbA-(1-4)-α-L-FucpAm3O-Ac-(1→3)-α-D-QuipNAc-(1→] (as shown in FIG. 1), comprising two aminodideoxyhexoses and one diaminodideoxyhexuronic acid, amino groups in the structure being modified by acetyl, acetamidino (Am) and D-3-hydroxybutyryl (Hb) respectively (A. Maciejewska et al., *Carbohydr. Res.* 2009, 344, 894-900). Although the high diversity of saccharide structures in nature is well known, saccharide molecules having diacylaminouronic acid similar to that in the *Plesiomonas shigelloides* O51 polysaccharide structure as well as rare groups acetamidino and 3-hydroxybutyryl are still extremely rare. Similar structures that have been reported are cell surface components from some important pathogens, such as *Vibrio vulnificus* YJ016 strain (S. N. Senchenkova et al., *Carbohydr. Res.* 2009, 344, 1009-1013) and CECT 5198 strain (A. S. Shashkov et al., *Carbohydr. Res.* 2009, 344, 2005-2009), *Pseudomonas aeruginosa* serotype O5 (A. Larkin et al., *Biochemistry* 2009, 48, 5446-5455), *Acinetobacter baumannii* ATCC 17961 strain (E. Fregolino et al., *Carbohydr. Res.* 2011, 346, 973-977) and the like, suggesting that such saccharide structures may be associated with pathogenicity of pathogens, and further verification of the related biological effects of saccharide structures relies on the availability of pure products for related research. The obtainment of polysaccharides by extraction is limited by the cumbersome pathogen culture and extraction and purification processes, and the extracted polysaccharide has the problem of structural heterogeneity and difficulty in completely removing impurities. In summary, the related oligosaccharide pure product with a definite structure obtained by a chemical synthesis method will provide an important basis for the research of pathogenicity of pathogens, the development of new antibacterial drugs and the research and development of new vaccines.

Although in the past few decades, synthetic chemists have continued to develop synthetic carbohydrate chemistry, such as the development of protecting group strategies, the development of new protecting groups, the development of glycosylation methods, and automated synthesis techniques. However, the hetero-modified polyamino saccharide structure represented by *Plesiomonas shigelloides* O51 polysaccharide is still considered to be a challenging target molecule by synthetic chemists. At present, the chemical synthesis of a similar hetero-modified polyamino saccharide structure including the *Plesiomonas shigelloides* O51 polysaccharide has not been reported. Since the aminodideoxyhexose and diaminohexuronic acid in the structure contain four amino groups functionalized with the rare acetamidino group and hydroxybutyryl group, and thus, will have an influence on the stereoselectivity of the glycosylation reaction and the orthogonal assembly of the different functional groups. Therefore, the total synthesis of this structure requires a holistic route design, including the selection of protecting groups, the selection of time for introducing functional groups, the efficiency and selectivity of glycosylation reaction.

SUMMARY

The present disclosure relates to a linkered oligosaccharide fragment of the *Plesiomonas shigelloides* serotype O51 O-antigen polysaccharide. The chemical structural formula of the saccharide chain can be expressed as the general Formula I:

$$V^*-[U_{x+2}-U_{x+1}-U_x]_n-V-O-L-NH_2 \qquad \text{Formula I}$$

wherein x is 1, 2, 3; n is 1, 2, 3; —V— represents: the chemical bond, —$U_{x+2}$—, or —$U_{x+2}$—$U_{x+1}$—; V*— represents: H—, H—$U_x$—, or H—$U_{x+1}$—$U_x$—; L represents the linker; $U_x$, $U_{x+1}$ and $U_{x+2}$ are as shown in Formula V (FIG. 2).

Formula V

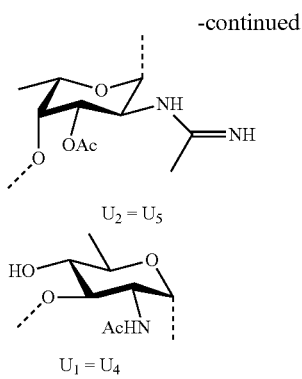

In the present disclosure, the linker L has the chain structure of 2 to 40 carbon atoms (including the number of carbon atoms in the side chain).

In the present disclosure, when the main chain length of the linker is 4-8 atoms, the chain may include 1, 2 or 3 heteroatoms (O, N and S). When the main chain length of the linker is 9-14 atoms, the chain may include 1, 2, 3, 4, 5 or 6 heteroatoms (O, N and S).

In the present disclosure, the linker -L- can be all or partially fluoro-substituted. The linker -L- may contain a three-, four-, five- or six-membered saturated carbocyclic ring; it may also contain a five-membered unsaturated carbocyclic ring (non-aromatic ring); it may also contain a four-, five- or six-membered saturated oxygen heterocyclic ring; it may also contain a four-, five- or six-membered saturated nitrogen heterocyclic ring; and it may also contain a six-membered aromatic carbocyclic ring.

In the present disclosure, the linker -L- may also contain an amide bond and/or a carbamido group.

In the present disclosure, the linker -L- may contain one or more substituent groups, and these substituents may include: —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$ and —N(C$_2$H$_5$)$_2$.

In the present disclosure, the synthesized saccharide chain structure contains basic (acetamidino) and acidic (carboxyl) groups which can form a corresponding salt with an organic or inorganic acid or base. Acids that can be used for forming a salt are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, vinyl sulfonic acid, p-toluenesulfonic acid, naphthalenesulfonic acid, sulfanilic acid, camphorsulfonic acid, mandelic acid, o-methyl mandelic acid, hydroxybenzenesulfonic acid, picric acid, adipic acid, o-toluenetartaric acid, tartronic acid, aminonaphthalene sulfonic acid, and other mineral acid or carboxylic acid substances. Inorganic or organic bases that can be used for forming a salt are sodium hydroxide, potassium hydroxide, aqueous ammonia, tetraalkylammonium hydroxide, lysine, arginine and the like.

In the present disclosure, the synthesized saccharide chain structure contains both basic (acetamidino) and acidic (carboxyl) groups, and thus, intramolecular protons, i.e., protons of acidic group can be transferred to basic group. The general Formula I can be an amphoteric molecule containing —O— and —NH$_{3+}$.

In the present disclosure, the connection between monosaccharide building blocks (U$_x$, U$_{x+1}$, U$_{x+2}$) is a glycosidic bond formed by anomeric carbon (1-position carbon) of a monosaccharide building block and corresponding hydroxyl oxygen of another monosaccharide building block.

The *Plesiomonas shigelloides* serotype O51 O-antigen saccharide chain in the present disclosure can be expressed as the general Formula II:

Formula II, wherein x, n, L, U$_x$, U$_{x+1}$, U$_{x+2}$ and V* are in accordance with the general Formula I. The general Formula II can be specifically expressed as Formulae II-a, II-b and II-c:

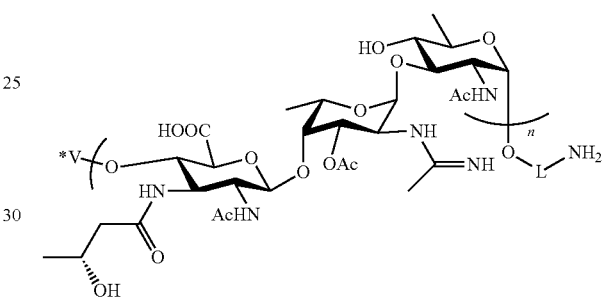

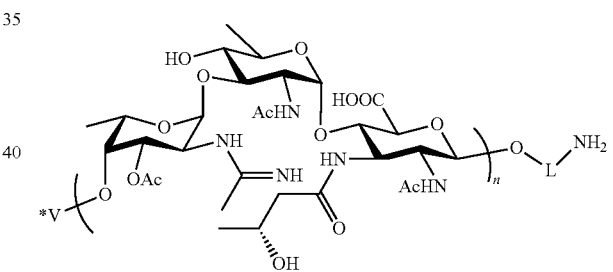

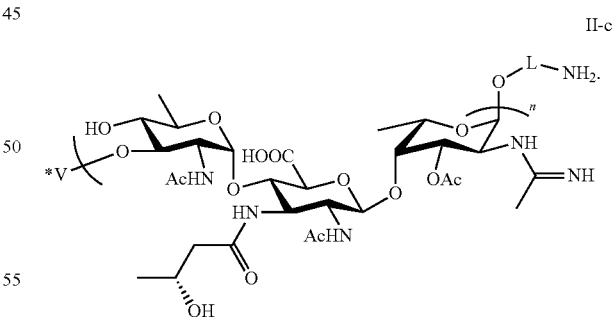

The *Plesiomonas shigelloides* serotype O51 O-antigen saccharide chain in the present disclosure can be expressed as the general Formula III:

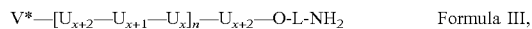

Formula III, wherein x, n, L, U$_x$, U$_{x+1}$, U$_{x+2}$ and V* are in accordance with the general Formula I. Formula III can be specifically expressed as general Formulae III-a, III-b and III-c:

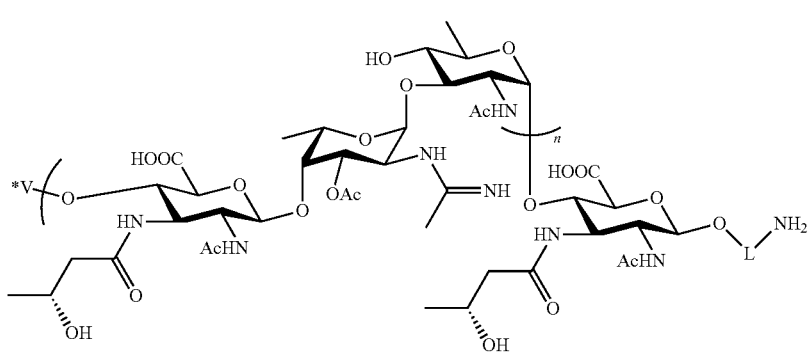

III-a

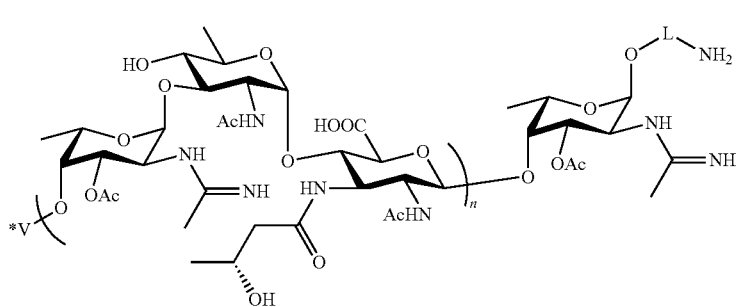

III-b

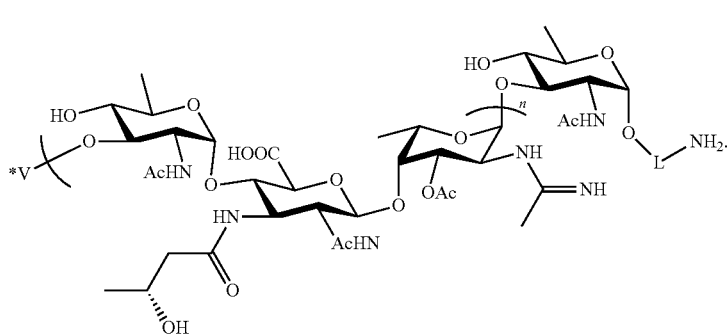

III-c

The *Plesiomonas shigelloides* serotype O51 O-antigen saccharide chain in the present disclosure can be expressed as the general Formula IV:

$$V^*-[U_{x+2}-U_{x+1}-U_x]_n-U_{x+2}-U_{x+1}-O-L-NH_2 \quad \text{Formula IV,}$$

wherein x, n, L, $U_x$, $U_{x+1}$, $U_{x+2}$ and V* are in accordance with the general Formula I. The general Formula IV can be specifically expressed as Formulae IV-a, IV-b and IV-c:

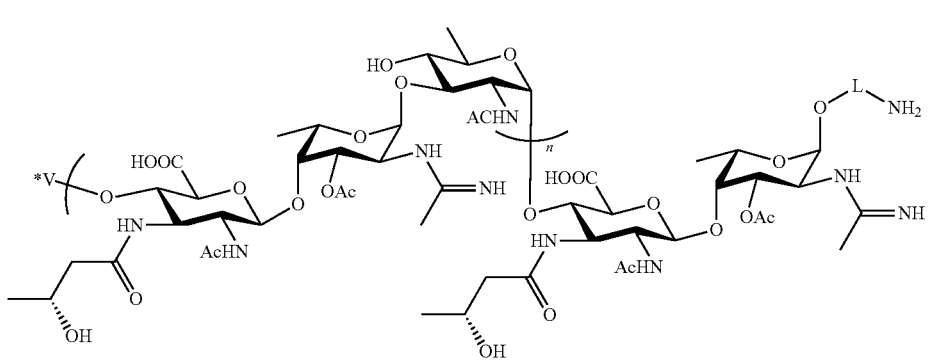

IV-a

IV-b
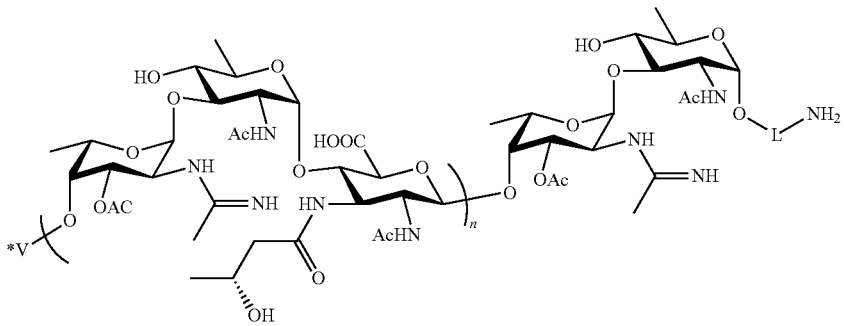
IV-c
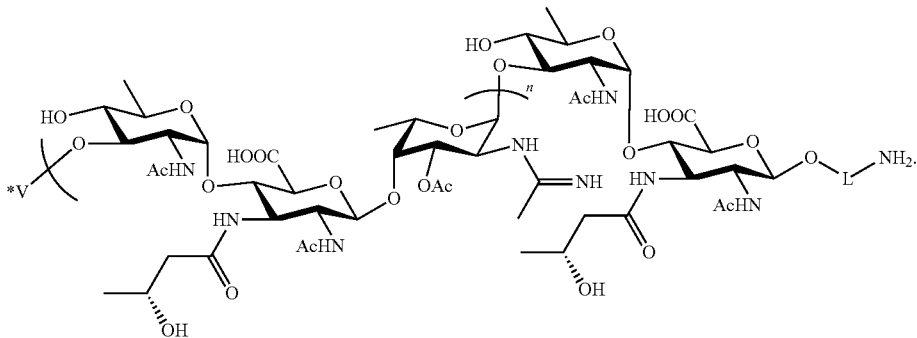
The present disclosure provides a chemical synthesis method of a linker installed saccharide chain (the general Formula I) of *Plesiomonas shigelloides* serotype O51 O-antigen oligosaccharide, characterized in that three monosaccharide building blocks 1, 2, 3 and a linker 4 are used as raw materials, as shown in Formulae V zoyl (Bz), acetyl (Ac), tert-butyldimethylsilyl (TBDMS), tert-butyldiphenylsilyl (TBDPS), triethylsilyl (TES) or the like.

The chemical synthesis method of *Plesiomonas shigelloides* O51 oligosaccharide provided by the present disclosure is characterized by including the following reaction modules:

1) Reaction Module A: Glycosylation Reaction

When the leaving group used in the glycosidation reaction is ethylthio, p-tolylthio or phenylthio, an activator in the glycosidation reaction can be selected from methyl trifluoromethanesulfonate (TfOMe), dimethyl(methylthio)sulfonium trifluoromethanesulfonate (DMTST), trifluoromethanesulfonic acid (TfOH)/N-iodosuccinimide (NIS) or trimethylsilyl trifluoromethanesulfonate (TMSOTf)/N-iodosuccinimide (NIS), and the reaction temperature can be −40° C. to room temperature;

when the leaving group is fluorine, the activator in the glycosylation reaction can be silver perchlorate ($AgClO_4$), titanium tetrafluoride ($TiF_4$), trifluoromethanesulfonic anhydride ($Tf_2O$) or the like, and the reaction temperature can be −40° C. to room temperature;

when the leaving group is bromine, the activator in the glycosylation reaction can be silver perchlorate ($AgClO_4$) or silver trifluoromethanesulfonate (AgOTf), and the reaction temperature can be −40° C. to room temperature; and when the leaving group is trichloroacetimidate, N-phenyl trifluoroacetimidate or dibutyl phosphate, the activator in the glycosylation reaction can be boron trifluoride diethyl etherate ($BF_3 \cdot OEt_2$), trimethylsilyl trifluoromethanesulfonate (TMSOTf) or silver trifluoromethanesulfonate (AgOTf), and the reaction temperature can be −40° C. to room temperature.

A molecular sieve used for water removal in the glycosylation reaction can be a 4 Å molecular sieve or a 3 Å molecular sieve.

2) Reaction Module B: Azido Reduction and Acetylation

Azido reduction and acetylation can be achieved directly by a thioacetic acid (AcSH)/pyridine method, or by reduction of azide to amine followed by acetylation. A method of reducing azide to amine can be trimethylphosphine ($PMe_3$)/water, triphenylphosphine ($PPh_3$)/water, 1,3-propanedithiol/triethylamine, sodium borohydride ($NaBH_4$)/nickel dichloride ($NiCl_2$), tin dichloride ($SnCl_2$)/thiophenol (PhSH)/triethylamine, zinc/copper/acetic acid, Lindlar catalyst/hydrogen, or the like; and the amino acetylation method can be acetic anhydride ($Ac_2O$)/methanol, acetic anhydride/pyridine, acetyl chloride (AcCl)/triethylamine or the like.

3) Reaction Module C: Monosaccharide Building Block 1 (D-Quinovosamine) 3-Position Deprotection When the hydroxyl protecting group is acetyl (Ac), benzoyl (Bz), chloroacetyl (ClAc), dichloroacetyl (DCA), trichloroacetyl (TCA) or pivaloyl (Piv), the deprotection condition can be sodium methoxide/methanol, potassium hydroxide/methanol, sodium hydroxide/methanol or the like;

when the hydroxyl protecting group is levulinyl (Lev), the deprotection condition can be hydrazine acetate/pyridine or the like;

when the hydroxyl protecting group is allyloxycarbonyl (Alloc), the deprotection condition can be palladium diacetate ($Pd(OAc)_2$)/diethylamine or the like;

when the hydroxyl protecting group is 2-naphthylmethyl (Nap) or p-methoxybenzyl (PMB), the deprotection condition can be 2,3-dichloro-5,6-dicyano-1,4-p-benzoquinone (DDQ)/water, ceric ammonium nitrate (CAN)/water or the like; and when the hydroxyl protecting group is tert-butyldimethylsilyl (TBDMS), tert-butyldiphenylsilyl (TBDPS) or triethylsilyl (TES), the deprotection condition can be tetrabutylammonium fluoride (TBAF), hydrofluoric acid or the like.

4) Reaction Module D: Azido Reduction and Protection by 2,2,2-Trichloroethoxycarbonyl (Troc)

The method of reducing azide to amine can be trimethylphosphine ($PMe_3$)/water, triphenylphosphine ($PPh_3$)/water, 1,3-propanedithiol/triethylamine, sodium borohydride ($NaBH_4$)/nickel dichloride ($NiCl_2$), tin dichloride ($SnCl_2$)/thiophenol (PhSH)/triethylamine, zinc/copper/acetic acid, Lindlar catalyst/hydrogen, or the like; and a method of protecting amino group by 2,2,2-trichloroethoxycarbonyl (Troc) can be achieved by using 2,2,2-trichloroethoxycarbonyl chloride (TrocCl) under the reaction condition with a weak base such as sodium bicarbonate, pyridine, triethylamine or the like.

5) Reaction Module E: Monosaccharide Building Block 2 (L-Fucosamine) 3,4-Position Selective Naphthylmethyl Protection The fucosamine 3,4-position selective naphthylmethyl protection specifically refers to, for 3,4-position hydroxyl groups, selectively performing naphthylmethyl protection on 3-position hydroxyl group and retaining 4-position hydroxyl group naked. The method can include: treating the raw material with dibutyltin oxide at 110° C. for 1 hour, and then treating reaction solution with 2-bromomethylnaphthalene and tetrabutylammonium bromide (TBAB) at the reaction temperature of room temperature to 110° C.

6) Reaction Module F: Monosaccharide Building Block 2 (L-Fucosamine) 3-Position Acetylation The acetylation of fucose 3-position is achieved by selective removal of a naphthylmethyl group and introduction of an acetyl group. A selective removal method of a naphthylmethyl group can be a 2,3-dichloro-5,6-dicyano-1,4-p-benzoquinone (DDQ)/water method or the like; and an introduction method of an acetyl group can be acetic anhydride/pyridine, acetyl chloride/pyridine, acetyl chloride/triethylamine or the like.

7) Reaction Module G: Azido Reduction and Butyrylation

A method of reducing azide to amine can be trimethylphosphine ($PMe_3$)/water, triphenylphosphine ($PPh_3$)/water, 1,3-propanedithiol/triethylamine, sodium borohydride ($NaBH_4$)/nickel dichloride ($NiCl_2$), tin dichloride ($SnCl_2$)/thiophenol (PhSH)/triethylamine, zinc/copper/acetic acid, Lindlar's catalyst/hydrogen, or the like;

a method of functionalizing amine with butyryl group can be carried out by using (R)-3-O-$PG^8$-butyric anhydride (as shown in FIG. 8) as a raw material with or without base treatment, wherein base can be pyridine, triethylamine or the like;

the method of functionalizing amine with butyryl group can be carried out by using (R)-3-O-$PG^8$-butyryl halide (acyl chloride, acyl bromide or acyl fluoride) (as shown in FIG. 8) as a raw material under base treatment, wherein base can be pyridine, triethylamine, sodium carbonate, sodium bicarbonate, potassium carbonate or the like;

the method of functionalizing amine with butyryl group can be (R)-3-O-$PG^8$-butyric acid (as shown in FIG. 8) as a raw material, and a condensation condition can be dicyclohexylcarbodiimide (DCC)/4-N,N-dimethylpyridine (DMAP), dicyclohexylcarbodiimide (DCC)/1-hydroxybenzotriazole (HOBt), diisopropylcarbodiimide (DIC)/4-N,N-dimethylpyridine (DMAP), diisopropylcarbodiimide (DIC)/

1-hydroxybenzotriazole (HOBt), 1-(3-dimethylaminopropyl)-3-ethylcarbodiimide (EDCI)/4-N,N-dimethylpyridine (DMAP), 1-(3-dimethylaminopropyl)-3-ethylcarbodiimide (EDCI)/1-hydroxybenzotriazole (HOBt), 2-(7-azabenzotriazol)-N,N,N',N'-tetramethyluronium hexafluorophosphate (HATU), O-benzotriazol-tetramethyluronium hexafluorophosphate (HBTU), 6-chlorobenzotriazole-1,1,3,3-tetramethyluronium hexafluorophosphate (HCTU), diphenylphosphoryl chloride (DPP-Cl) or diethyl cyanophosphonate (DECP).

The hydroxyl protecting group $PG^8$ in (R)-3-hydroxybutyryl can be benzyl (Bn).

8) Reaction Module H: Removal of Troc and Introduction of Acetamidine

A removal method of Troc can be zinc powder/acetic acid, the content of acetic acid is 50% to 100%, and the reaction temperature is room temperature to 65° C.;

a method of modifying amino group to acetamidino group can be carried out by using aryl thioacetimidate halate or alkyl thioacetimidate halate (as shown in FIG. 9) under basic condition, aryl can be benzyl or naphthylmethyl, alkyl can be methyl or ethyl, the halogen acid can be hydrochloric acid or hydrobromic acid, and base can be pyridine, triethylamine, diisopropylethylamine, 1,8-diazabicyclo[5.4.0]undec-7-ene (DBU), potassium carbonate or sodium carbonate; and the method of modifying amino group to acetamidino group can be carried out by using alkyl acetimidate halate (as shown in FIG. 10) under basic condition, alkyl can be ethyl, trifluoroethyl or trichloroethyl, halogen acid can be hydrochloric acid or hydrobromic acid, and base can be pyridine, triethylamine, diisopropylethylamine, 1,8-diazabicyclo[5.4.0]undec-7-ene (DBU), potassium carbonate or sodium carbonate.

9) Reaction Module I: Hydrogenation for Global Deprotection

The hydrogenation for global deprotection can be achieved by carrying out a reaction at room temperature under catalytic conditions by introducing hydrogen. A catalyst used for the hydrogenation can be a 10% palladium on carbon catalyst or palladium hydroxide, and a solvent used for the reaction can be water/methanol/dichloromethane/acetic acid mixture or water/tert-butanol/dichloromethane mixture.

10) Reaction Module J: Monosaccharide Building Block 3 (D-Glucuronic Acid) 4-Position Deprotection When the hydroxyl protecting group is 2-naphthylmethyl (Nap) or p-methoxybenzyl (PMB), a deprotection method is a 2,3-dichloro-5,6-dicyano-1,4-p-benzoquinone (DDQ)/water method; and when the hydroxyl protecting group is levulinyl (Lev), the deprotection method is hydrazine acetate/pyridine.

11) Reaction Module K: Azido Reduction and Introduction of Acetamidine

The method of reducing azide to amine can be trimethylphosphine ($PMe_3$)/water, triphenylphosphine ($PPh_3$)/water, 1,3-propanedithiol/triethylamine, sodium borohydride ($NaBH_4$)/nickel dichloride ($NiCl_2$), tin dichloride ($SnCl_2$)/thiophenol (PhSH)/triethylamine, zinc/copper/acetic acid or Lindlar's catalyst/hydrogen;

the method of modifying amino group to acetamidino group can be carried out by using aryl thioacetimidate halate or alkyl thioacetimidate halate (as shown in FIG. 9) under basic condition, aryl can be benzyl or naphthylmethyl or the like, alkyl can be methyl or ethyl, halogen acid can be hydrochloric acid or hydrobromic acid, and base can be pyridine, triethylamine, diisopropylethylamine, 1,8-diazabicyclo[5.4.0]undec-7-ene (DBU), potassium carbonate or sodium carbonate; and the method of modifying amino group to acetamidino group can be carried out by using aryl acetimidate halide (as shown in FIG. 10) under basic condition, aryl can be ethyl, trifluoroethyl or trichloroethyl, halogen acid can be hydrochloric acid, or hydrobromic acid, and base can be pyridine, triethylamine, diisopropylethylamine, 1,8-diazabicyclo[5.4.0]undec-7-ene (DBU), potassium carbonate or sodium carbonate.

The chemical synthesis method of *Plesiomonas shigelloides* O51 oligosaccharide provided by the present disclosure is characterized by including the following reaction steps:

1) When n is 1 and V*— is H—, the synthesis steps of II-a include (as shown in FIG. 11): a monosaccharide building block 1 is subjected to glycosylation reaction to assemble a linker, followed by the reaction modules B and C to obtain a monosaccharide acceptor 5. Then glycosylation reaction is carried out with monosaccharide acceptor 5 and the monosaccharide building block 2 to obtain a disaccharide 6. The disaccharide 6 is subjected to the reaction modules D and E to obtain a disaccharide acceptor 7, and then glycosylation reaction is carried out with a monosaccharide building block 3 to obtain a trisaccharide 8. The trisaccharide 8 is subjected to the reaction module F to achieve acetylation, and then the reaction modules G and H are carried out to achieve the amino functional group assembly so as to obtain a trisaccharide 11. Then the hydrogenation of the reaction module I is carried out with the trisaccharide 11 to obtain a trisaccharide II-a.

2) When n is 1 and V*— is H—, the synthesis steps of II-b include (as shown in FIG. 12): the monosaccharide building block 3 is subjected to glycosylation to assemble the linker, obtaining monosaccharide 12. The monosaccharide 12 is subjected to the reaction modules G and J to obtain a monosaccharide acceptor 13. The monosaccharide acceptor 13 is subjected to glycosylation reaction with the monosaccharide building block 1 to obtain a disaccharide 14, and then the disaccharide 14 is subjected to the reaction modules B and C to obtain a disaccharide acceptor 15. The disaccharide acceptor 15 is subjected to glycosylation reaction with the monosaccharide building block 2 to obtain a trisaccharide 16, and then the trisaccharide 16 is subjected to the reaction module K to achieve the acetamidino assembly to obtain a trisaccharide 17. Then the trisaccharide II-b is obtained by further hydrogenation of the reaction module I of the trisaccharide 17.

3) When n is 1 and V*— is H—, the synthesis steps of II-c include (as shown in FIG. 13): the monosaccharide building block 2 is subjected to glycosylation reaction to assemble the linker, obtaining compound 18. Then the obtained compound 18 is reacted by the reaction modules D and E to produce the monosaccharide acceptor 19. The glycosylation reaction is carried out with the monosaccharide acceptor 19 and the monosaccharide building block 3 to obtain a disaccharide. Then the reaction modules F, G and J are carried out with the disaccharide to obtain a disaccharide acceptor 21. Then the trisaccharide 22 is synthesized by glycosylation reaction of the disaccharide acceptor 21 and the monosaccharide building block 1. The reaction modules B and H is carried out with the trisaccharide 22 to achieve the amino functional group assembly so as to obtain a trisaccharide 24. Then the trisaccharide II-c is prepared by the hydrogenation of the reaction module I of trisaccharide 24.

4) When n is 1 and V*— is H—, the synthesis steps of III-a include (as shown in FIG. 14): the trisaccharide 16 is subjected to the reaction modules D and E to obtain a trisaccharide acceptor 25. The trisaccharide acceptor 25 is subjected to glycosylation reaction with the monosaccharide building block 3 to obtain a tetrasaccharide 26. Then the tetrasaccharide 29 is synthesized by reaction module F to achieve the fucose acetylation, and the reaction modules G and H to achieve the amino functional group assembly, based on the tetrasaccharide 26. The hydrogenation of the reaction module I is carried out of the tetrasaccharide 29 to obtain the tetrasaccharide III-a.

5) When n is 1 and V*— is H—, the synthesis steps of III-b include (as shown in FIG. 15): the trisaccharide 23 is subjected to deprotection of the reaction module C to obtain a trisaccharide acceptor 30. The trisaccharide acceptor 30 is subjected to glycosylation reaction with the monosaccharide building block 2 to obtain the tetrasaccharide 31, followed by the reaction modules D and H to achieve the acetamidino assembly to prepare the tetrasaccharide 32. Then the tetrasaccharide III-b is prepared by the hydrogenation of the reaction module I of the tetrasaccharide 32.

6) When n is 1 and V*— is H—, the synthesis steps of III-c include (as shown in FIG. 16): the trisaccharide 10 is subjected to deprotection of the reaction module J to obtain a trisaccharide acceptor 33. The trisaccharide acceptor 33 is subjected to glycosylation reaction with the monosaccharide building block 1 to obtain the tetrasaccharide 34, followed by the reaction modules B and H to achieve the amino functional group assembly to obtain the tetrasaccharide 36. Then the tetrasaccharide III-c is prepared by the hydrogenation of the reaction module I of the tetrasaccharide 36.

7) When n is 1 and V*— is H—, the synthesis steps of IV-a include (as shown in FIG. 17): the tetrasaccharide 31 is subjected to the reaction modules D and E to obtain a tetrasaccharide acceptor 37, followed by the glycosylation reaction further carried out with the monosaccharide building block 3 to obtain a pentasaccharide 38. The pentasaccharide 38 is subjected to the reaction module F to achieve the fucose acetylation and the reaction modules G and H are carried out to achieve the amino functional group assembly, to obtain the pentasaccharide 41. Then the pentasaccharide IV-a is produced by the hydrogenation of the reaction module I of the pentasaccharide 41.

8) When n is 1 and V*— is H—, the synthesis steps of IV-b include (as shown in FIG. 18): the tetrasaccharide 35 is subjected to deprotection of the reaction module C to obtain a tetrasaccharide acceptor 42, followed by the glycosylation reaction further carried out with the monosaccharide building block 2 to obtain the pentasaccharide 43. The pentasaccharide 43 is subjected to the reaction modules D and H to achieve the acetamidino modification to obtain the pentasaccharide 44. Then the pentasaccharide IV-b is obtained by the hydrogenation of the reaction module I of the pentasaccharide 44.

9) When n is 1 and V*— is H—, the synthesis steps of IV-c include (as shown in FIG. 19): the tetrasaccharide 28 is subjected to deprotection of the reaction module J to obtain a tetrasaccharide acceptor 45, followed by the glycosylation reaction further carried out with the monosaccharide building block 1 to obtain the pentasaccharide 46. The pentasaccharide 46 is subjected to the reaction modules B and H to achieve the amino functional group assembly to obtain the pentasaccharide 48. Then the pentasaccharide IV-c is synthesized by the hydrogenation of the reaction module I of the pentasaccharide 48.

According to the chemical synthesis method of *Plesiomonas shigelloides* O51 oligosaccharide provided by the present disclosure, when the saccharide building block 1 (quinovose) is used as a glycosyl donor, the 2-position amino group can be masked by an azido group, which is beneficial to the generation of 1,2-cis-α-glycosidic bond.

According to the chemical synthesis method of *Plesiomonas shigelloides* O51 oligosaccharide provided by the present disclosure, when the saccharide building block 2 (fucose) is used as a glycosyl donor, the 2-position amino group can be masked by an azido group, which is beneficial to the generation of 1,2-cis-α-glycosidic bond.

According to the chemical synthesis method of *Plesiomonas shigelloides* O51 oligosaccharide provided by the present disclosure, when the 4-position hydroxyl group of the saccharide building block 2 (fucose) is used as a glycosylation reaction acceptor, in order to increase the nucleophilicity of the 4-position hydroxyl group, the 2-position amino group of the saccharide building block 2 (fucose) can be protected by Troc, and the 3-position hydroxyl group can be protected by naphthylmethyl.

According to the chemical synthesis method of *Plesiomonas shigelloides* O51 oligosaccharide provided by the present disclosure, when the saccharide building block 3 (glucuronic acid) is used as a glycosyl donor, the 3-position amino group in its structure can use azido group as a protecting group, thereby avoiding hindrance to the glycosylation reaction by the amide protecting group.

According to the chemical synthesis method of *Plesiomonas shigelloides* O51 oligosaccharide provided by the present disclosure, when the saccharide building block 3 (glucuronic acid) is used as a glycosyl donor, the 2-position amino group in its structure can be protected by trichloroacetyl, which is beneficial to the generation of the β-configuration glycosidic bond, and the amino group can be converted into acetamido group through hydrogenation.

According to the chemical synthesis method of *Plesiomonas shigelloides* O51 oligosaccharide provided by the present disclosure, the 2-position acetamido group in the structure of the saccharide building block 1 (quinovose) can be introduced immediately after the glycosylation reaction of the saccharide building block 1 (quinovose) is completed, thereby avoiding hindering the introduction of the saccharide building block thereafter.

According to the chemical synthesis method of *Plesiomonas shigelloides* O51 oligosaccharide provided by the present disclosure, the 3-position naphthylmethyl of the saccharide building block 2 (fucose) can be subjected to acetylation immediately after the 4-position glycosylation reaction is completed, thereby avoiding hindering the introduction of the saccharide building block thereafter.

According to the chemical synthesis method of *Plesiomonas shigelloides* O51 oligosaccharide provided by the present disclosure, the assembly of the 3-position butyrylamido in the structure of the saccharide building block 3 (glucuronic acid) should be completed before the 4-position deprotection of glucuronic acid, thereby avoiding hindering the introduction of the saccharide building block thereafter.

The present disclosure further provides three orthogonal protective intermediates for preparing hetero-modified polyaminosaccharides, which are compounds of the general Formula 8, the general Formula 16 and the general Formula 22. The three compounds can achieve the assembly of different amino functional groups, and can also be further used for the extension of oligosaccharide chains.

The present disclosure is the first to achieve the chemical synthesis of the *Plesiomonas shigelloides* serotype O51

O-antigen saccharide structure. In addition, the introduction of the corresponding linker to the reducing end of the saccharide structure provides the basis for the synthetic oligosaccharide structure to be coupled to the carrier molecule or immobilized to a corresponding substrate, which will contribute to the research of the biological activity of the *Plesiomonas shigelloides* serotype O51 O0-antigen saccharide structure, the development of saccharide vaccines and the like.

DETAILED DESCRIPTION

Commercially available reagents used in experiments were directly used without any treatment. The anhydrous solvents used in reaction were prepared by an MBraun MB-SPS 800 solvent drying system. Solvents used in silica gel column chromatography were all analytically pure and used after distillation under reduced pressure. A silica gel plate used for thin layer chromatography (TLC) was a glass-based or aluminum foil-based silica gel plate prepared from 60-F254 silica gel. A thin layer chromatography stain was a sugar stain (0.1% (v/v) 3-methoxyphenol, 2.5% (v/v) sulfuric acid ethanol solution), or a CAM stain (5% (w/v) ammonium molybdate, 1% (w/v) cerium sulfate (II) and 10% (v/v) sulfuric acid aqueous solution), or a ninhydrin stain (1.5% (w/v) ninhydrin and 3% (v/v) acetic acid n-butanol solution). Silica gel used for normal-phase silica gel column chromatography was 200-300-mesh silica gel. A column used in the molecular exclusion chromatography was Sephadex® LH-20 (GE Healthcare).

The yield of each reaction step was calculated separately, and the yield was calculated according to: (amount of target product/amount of raw materials)×100%. The structure of the product was identified by nuclear magnetic spectroscopy, infrared spectroscopy, optical rotation and high-resolution mass spectrometry. The purity of the product was analyzed by nuclear magnetic spectroscopy and high performance liquid chromatography. The $^1$H, $^{13}$C and two-dimensional nuclear magnetic spectrum were measured by a Bruker Ascend 400 MHz nuclear magnetic resonance spectrometer, or a Bruker Ultrashield Plus 400 MHz nuclear magnetic resonance apparatus, or a Bruker AVIII 700 MHz nuclear magnetic resonance spectrometer at 25° C. The high resolution mass spectrum was measured by an Agilent 6220 electrospray ionization time-of-flight mass spectrometer. The optical rotation was measured by the Schmidt & Haensch UniPol L 1000 automatic polarimeter at 589 nm, and the concentration (c) unit was g/100 mL. The infrared spectrum was measured by the Thermo Fisher Scientific Nicolet iS5 infrared meter. The analytical high performance liquid chromatography was performed by an Agilent 1200 series liquid chromatograph-quadrupole electrospray mass spectrometer 6130 using the Thermo Scientific Hypercarb column (150×4.6 mm) as an analytical column. The preparative high performance liquid chromatography was performed by an Agilent 1200 series liquid-phase chromatograph-quadrupole electrospray mass spectrometer 6130 using the Thermo Scientific Hypercarb column (150×10 mm) as the semi-preparative column.

Embodiment 1

Synthesis of allyl 3,4,6-tri-O-acetyl-2-deoxy-2-trichloroacetamido-α-D-glucopyranose (1*)

Figure 1:
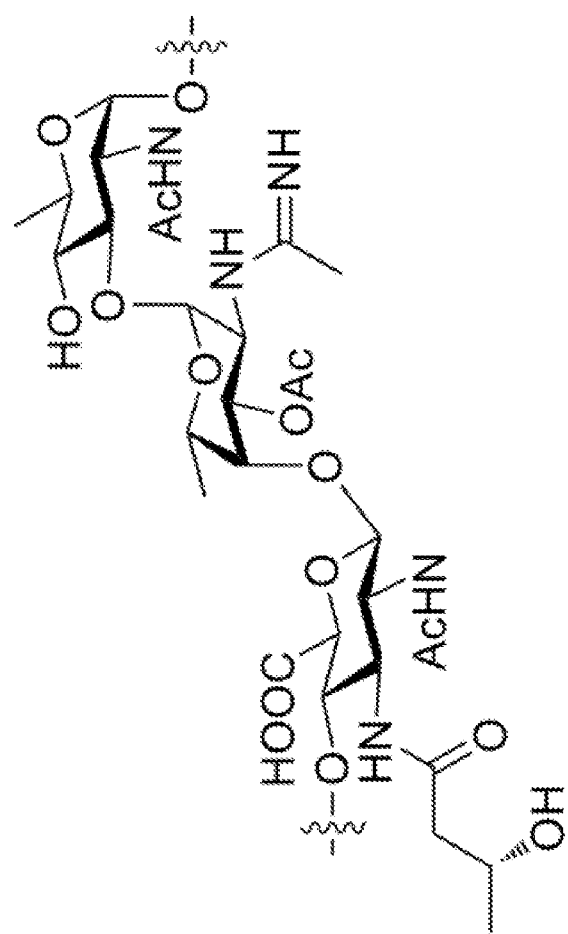
FIG. 1: *Plesiomonas shigelloides* serotype O51 O-antigen trisaccharide repeat unit.
Figure 2:
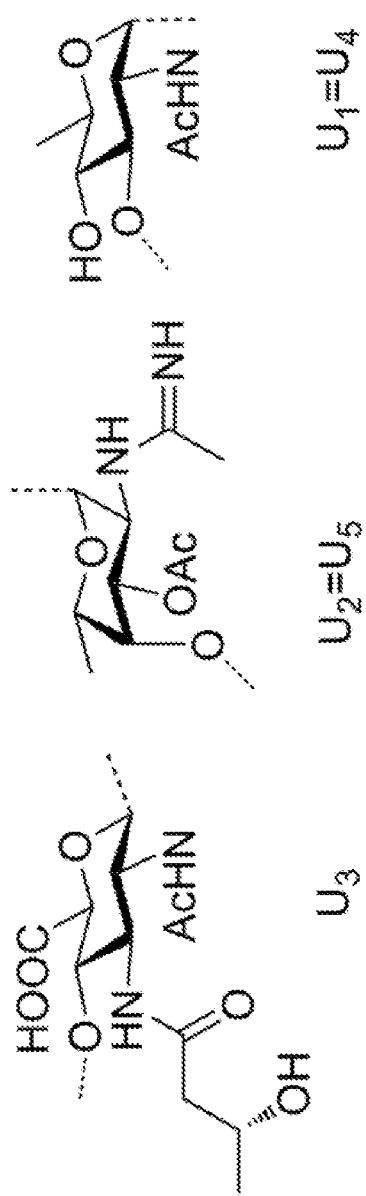
FIG. 2: Compounds of $U_x$, $U_{x+1}$ and $U_{x+2}$ in the general Formula I of the linkered oligosaccharide chain fragment of the *Plesiomonas shigelloides* serotype O51 O-antigen polysaccharide, where x=1, 2, 3.
Figure 3:
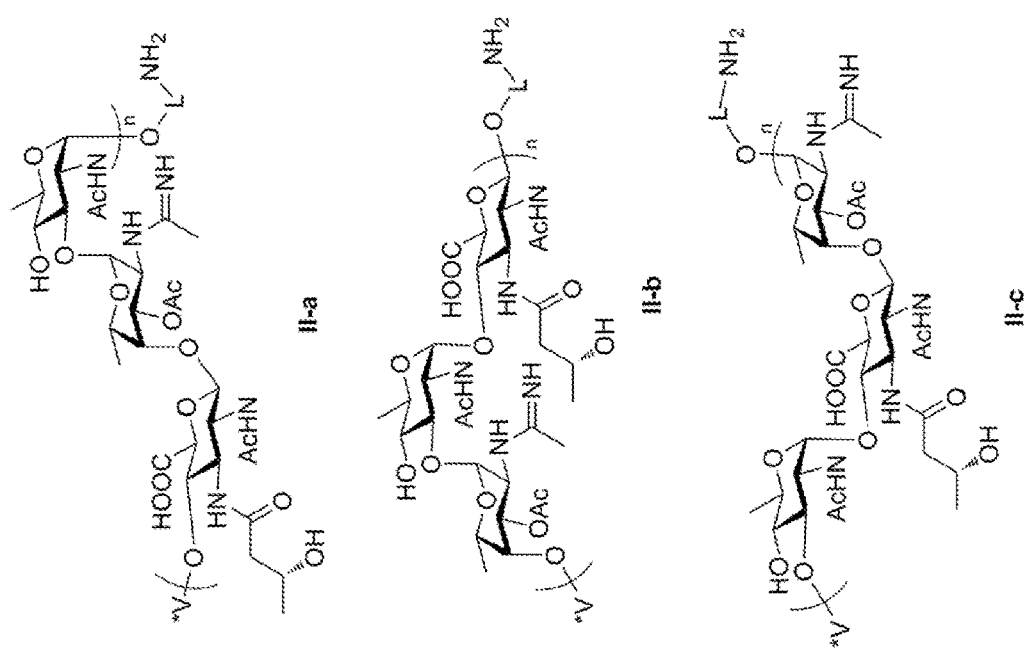
FIG. 3: Compounds of general Formulae II-a, II-b and II-c of the linkered oligosaccharide chain fragment of the *Plesiomonas shigelloides* serotype O51 O-antigen polysaccharide, where II-a is V*—[$U_3$—$U_2$—$U_1$]$_n$—O-L-NH$_2$; II-b is V*—[$U_5$—$U_4$—$U_3$]$_n$—O-L-NH$_2$; II-C is V*—[$U_4$—$U_3$—$U_2$]$_n$—O-L-NH$_2$.
Figure 4:
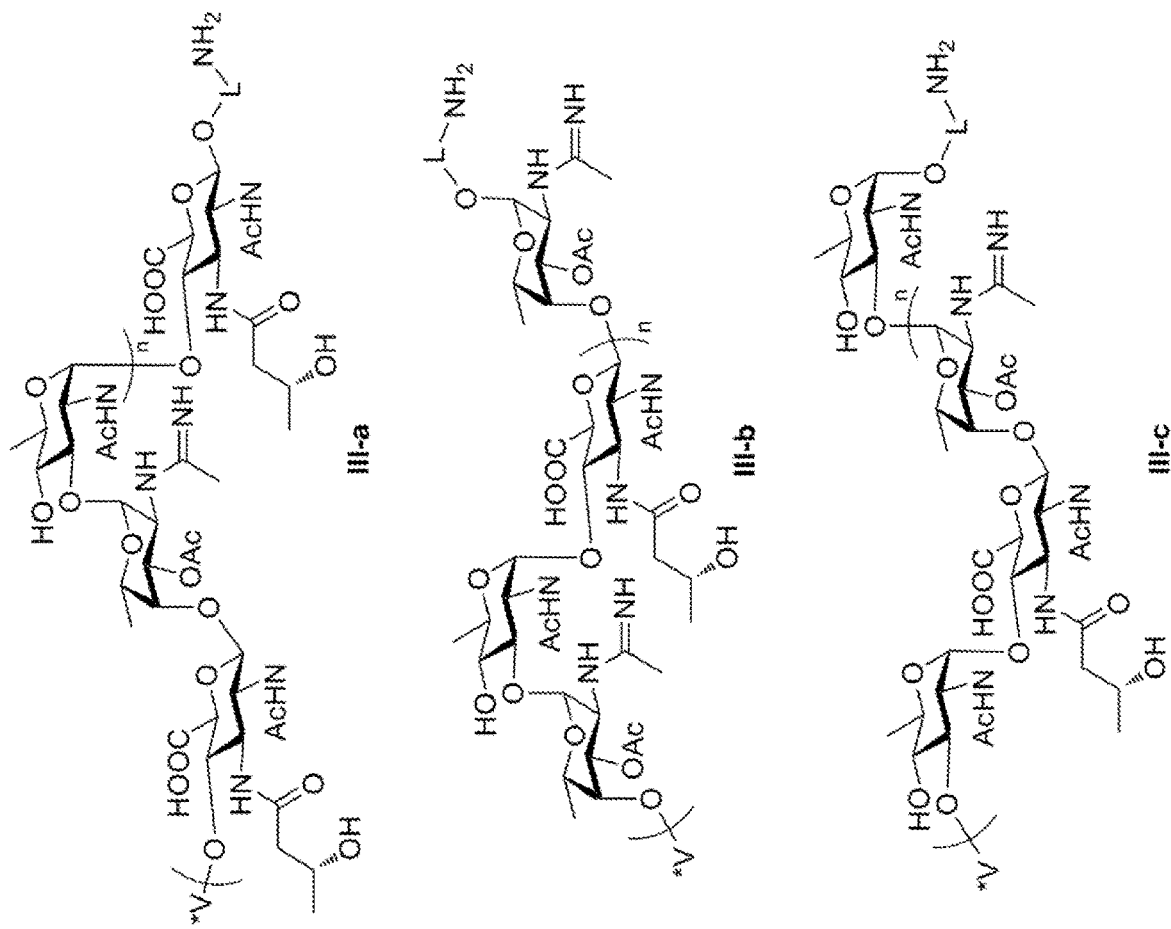
FIG. 4: Compounds of general Formulae III-a, III-b and III-c of the linkered oligosaccharide chain fragment of the *Plesiomonas shigelloides* serotype O51 O-antigen polysaccharide, where III-a is V*—[$U_3$—$U_2$—$U_1$]$_n$—$U_3$—O-L-NH$_2$; III-b is V*—[$U_5$—$U_4$—$U_3$]$_n$—$U_5$—O-L-NH$_2$; III-c is V*—[$U_4$—$U_3$—$U_2$]$_n$—$U_4$—O-L-NH$_2$.
Figure 5:
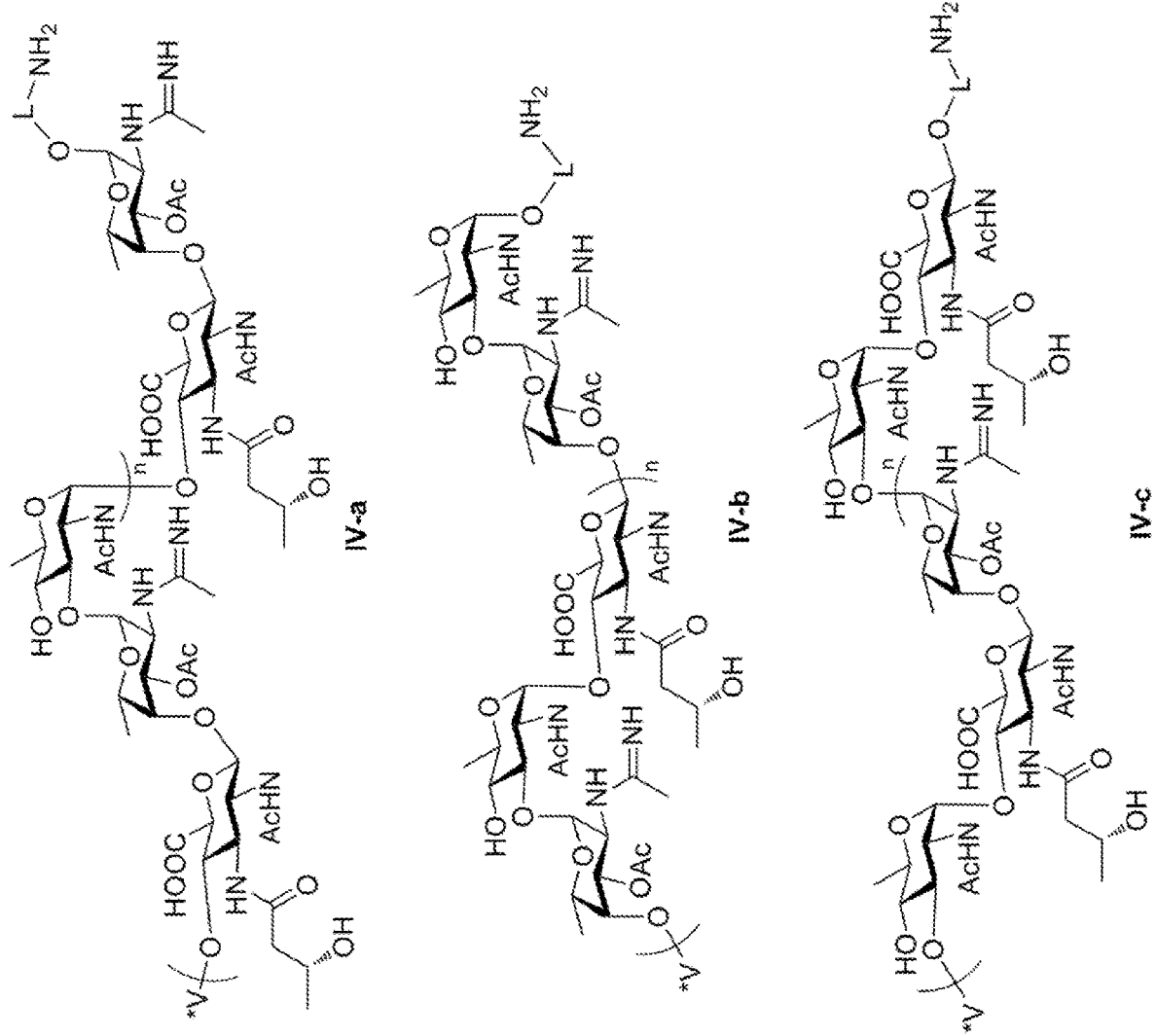
FIG. 5: Compounds of general Formulae IV-a, IV-b and IV-c of the linkered oligosaccharide chain fragment of the *Plesiomonas shigelloides* serotype O51 O-antigen polysaccharide, where IV-a is V*—[$U_3$—$U_2$—$U_1$]$_n$—$U_3$—$U_2$—O-L-NH$_2$; IV-b is V*—[$U_5$—$U_4$—$U_3$]$_n$—$U_5$—$U_4$—O-L-NH$_2$; IV-c is V*—[$U_4$—$U_3$—$U_2$]$_n$—$U_4$—$U_3$—O-L-NH$_2$.
Figure 6:
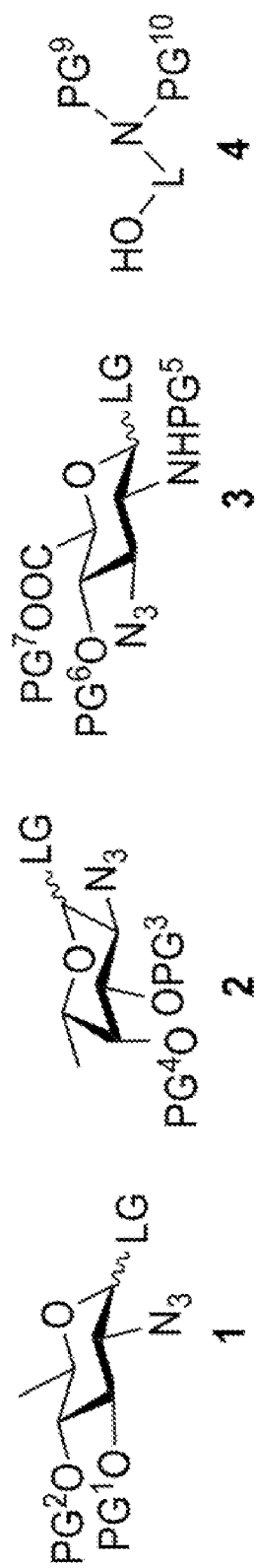
FIG. 6: Compounds of monosaccharide building blocks 1, 2 and 3 and the linker 4, wherein monosaccharide building block 1, $PG^1$ is a hydroxyl protecting group, $PG^2$ is a hydroxyl protecting group; in monosaccharide building block 2, $PG^3$, $PG^4$ are hydroxyl protecting groups; in monosaccharide building block 3, $PG^5$ is an amino protecting group, $PG^6$ is a hydroxyl protecting group, $PG^7$ is a carboxyl protecting group; in monosaccharide building block 4, $PG^9$ and $PG^{10}$ are amino protecting groups; LG is a leaving group for a glycosylation reaction monosaccharide building blocks 1, 2 and 3.
Figure 7:
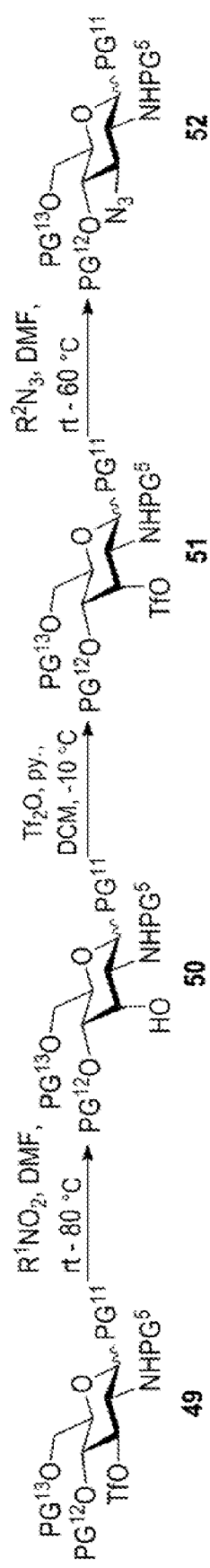
FIG. 7: Synthesis of 2,3-diglucosamine 52.
Figure 8:
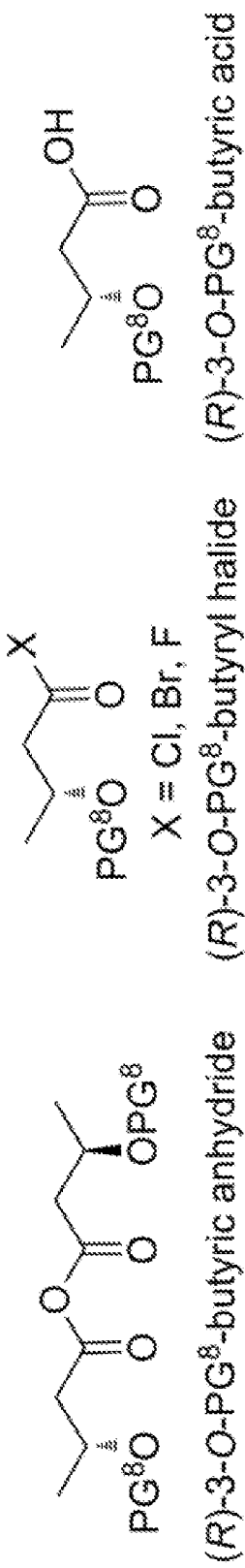
FIG. 8: Butyryl compounds used by amino butyrylation modification, where from left to right is (R)-3-O-$PG^8$-butyric anhydride, (R)-3-O-$PG^8$-butyryl halide and (R)-3-O-$PG^8$-butyric acid.
Figure 9:
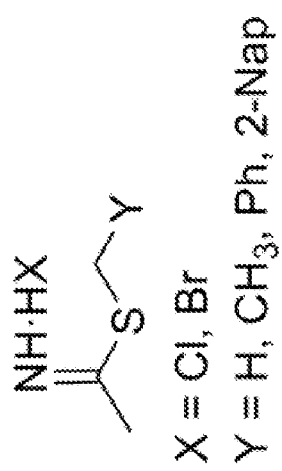
FIG. 9: Aryl (alkyl) thioacetimidate halate.
Figure 10:
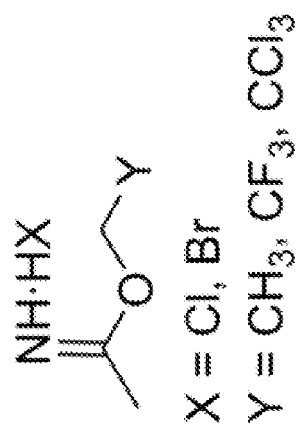
FIG. 10: Alkyl acetimidate halate.
Figure 11:
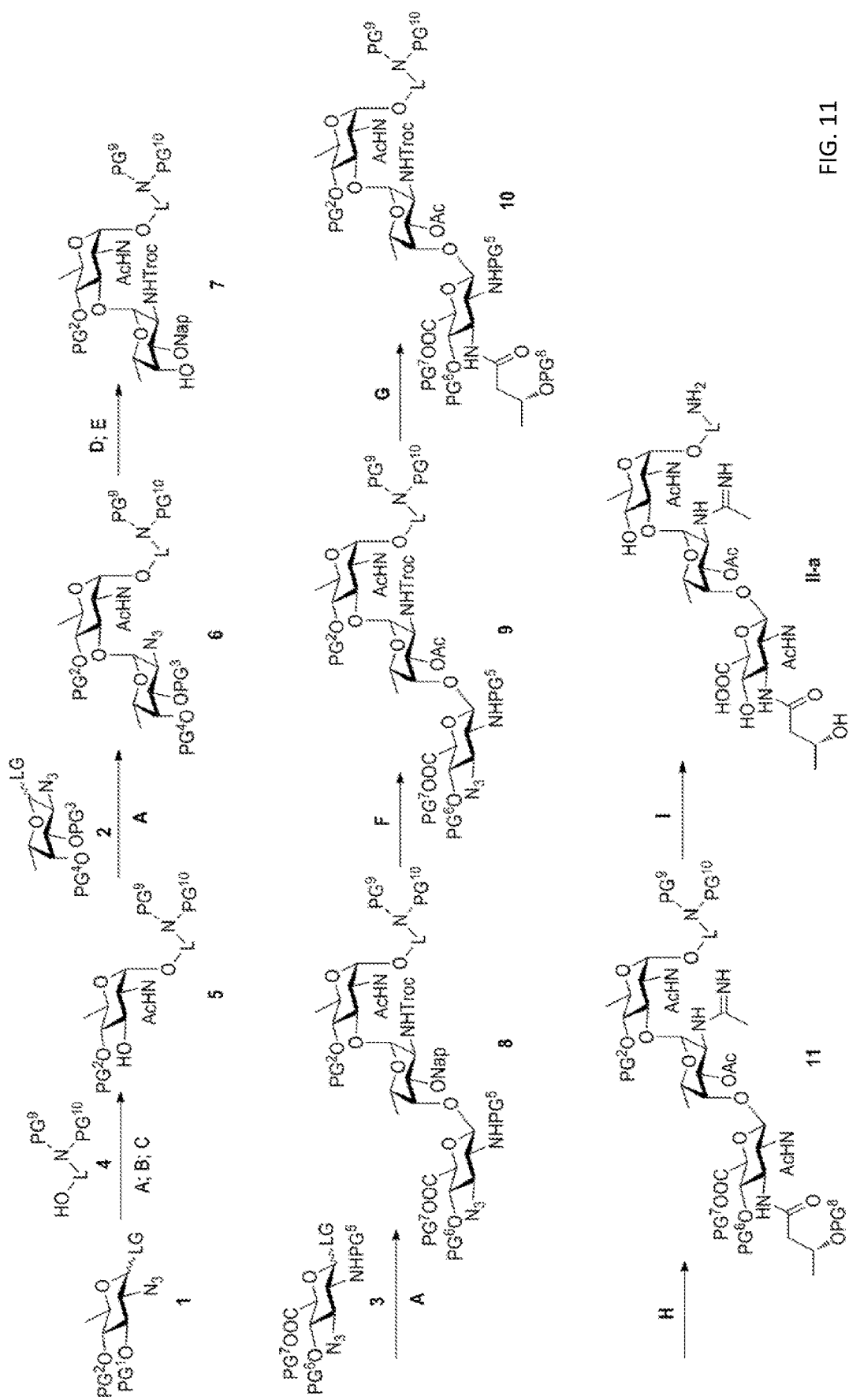
FIG. 11: Synthesis of *Plesiomonas shigelloides* O51 trisaccharide II-a.
Figure 12:
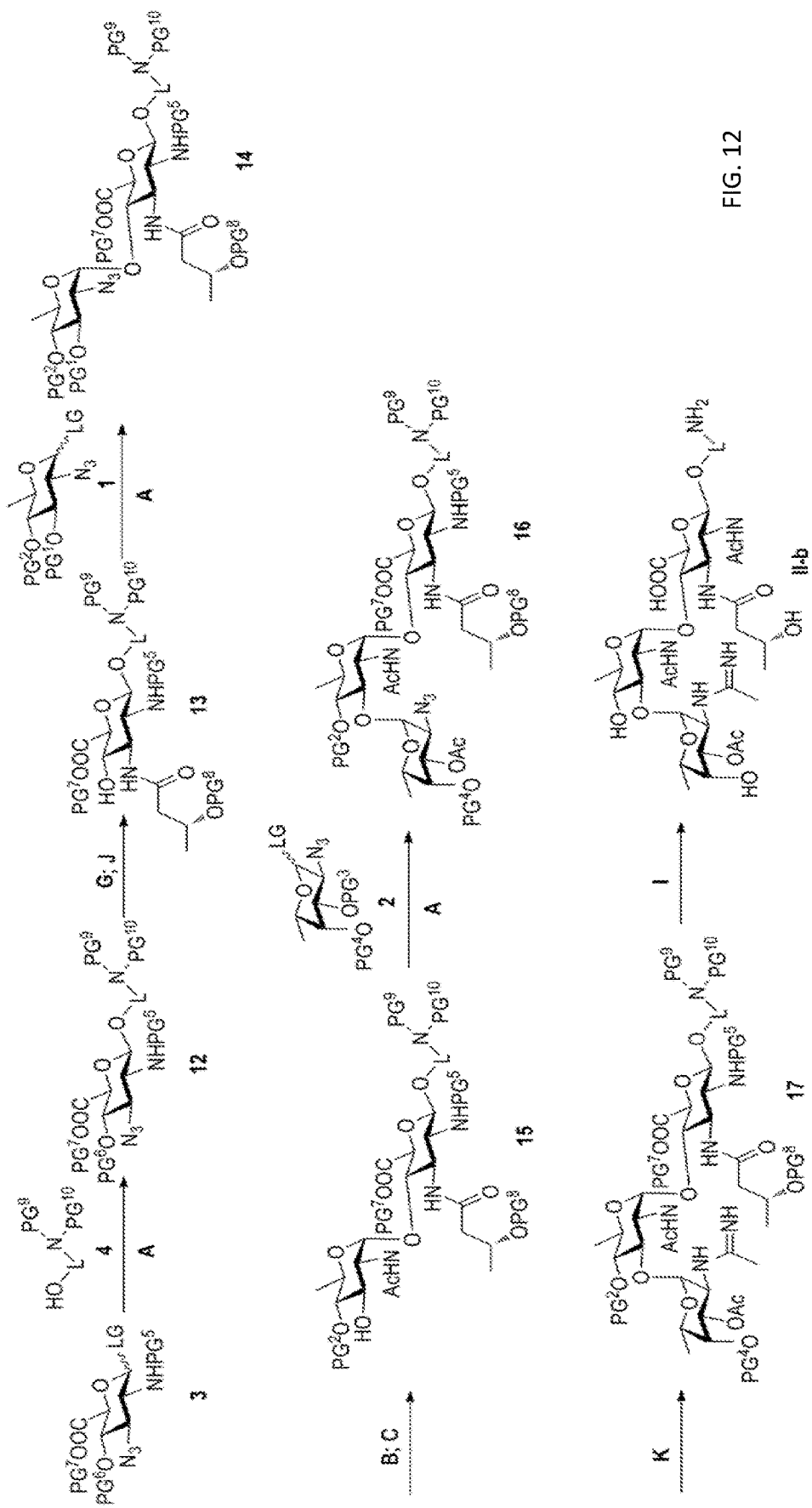
FIG. 12: Synthesis of *Plesiomonas shigelloides* O51 trisaccharide II-b.
Figure 13:
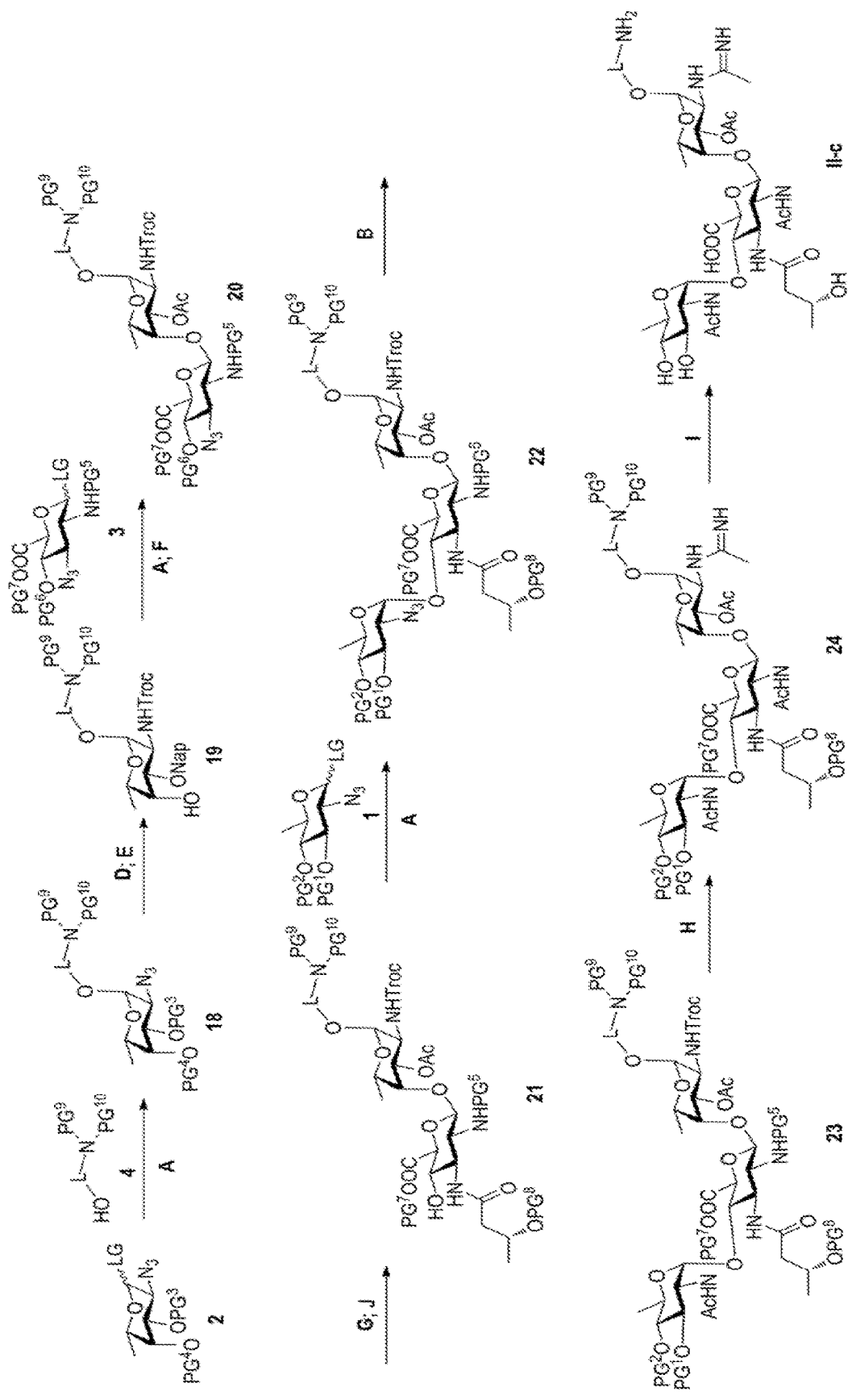
FIG. 13: Synthesis of *Plesiomonas shigelloides* O51 trisaccharide II-c.
Figure 14:
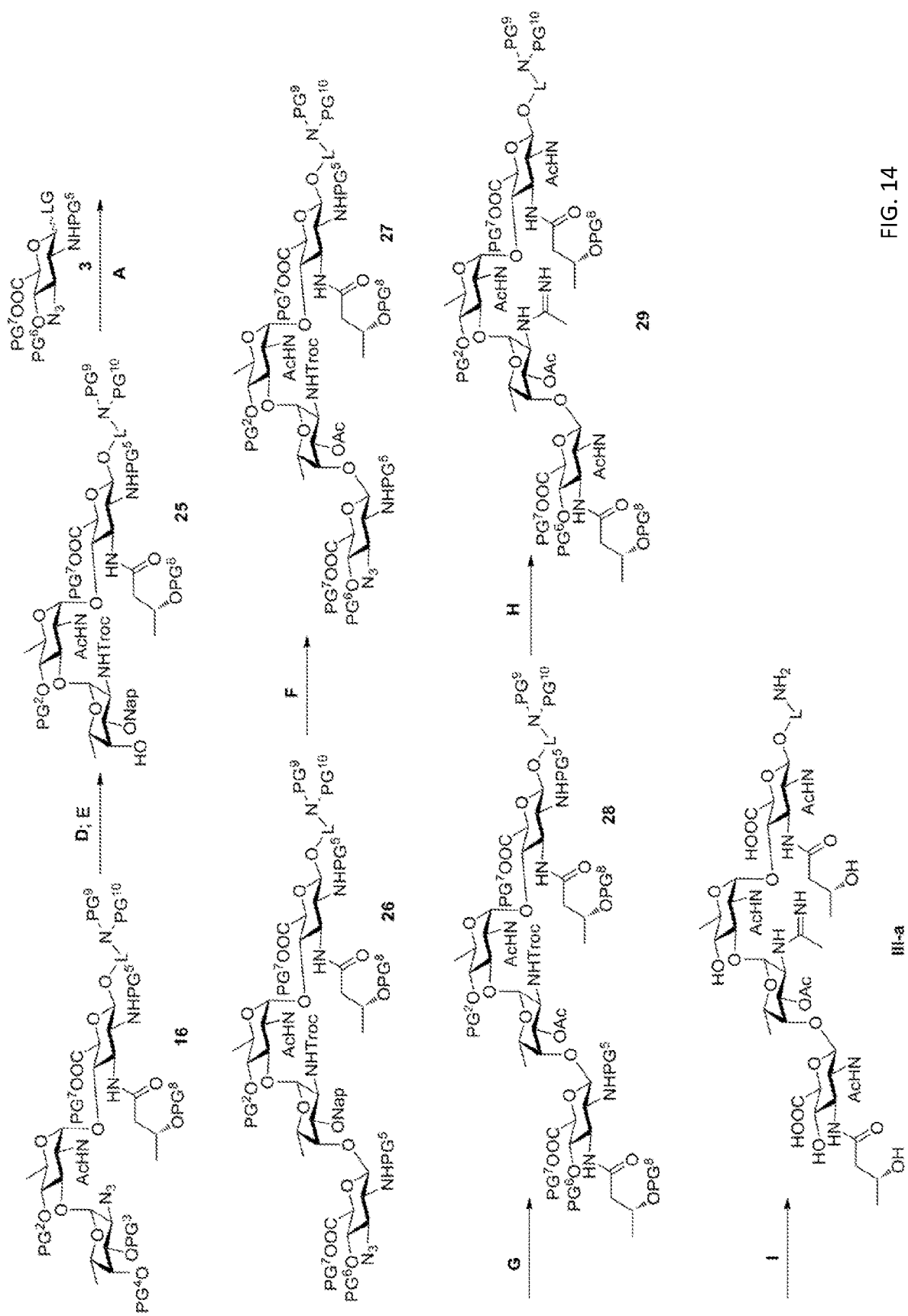
FIG. 14: Synthesis of *Plesiomonas shigelloides* O51 tetrasaccharide III-a.
Figure 15:
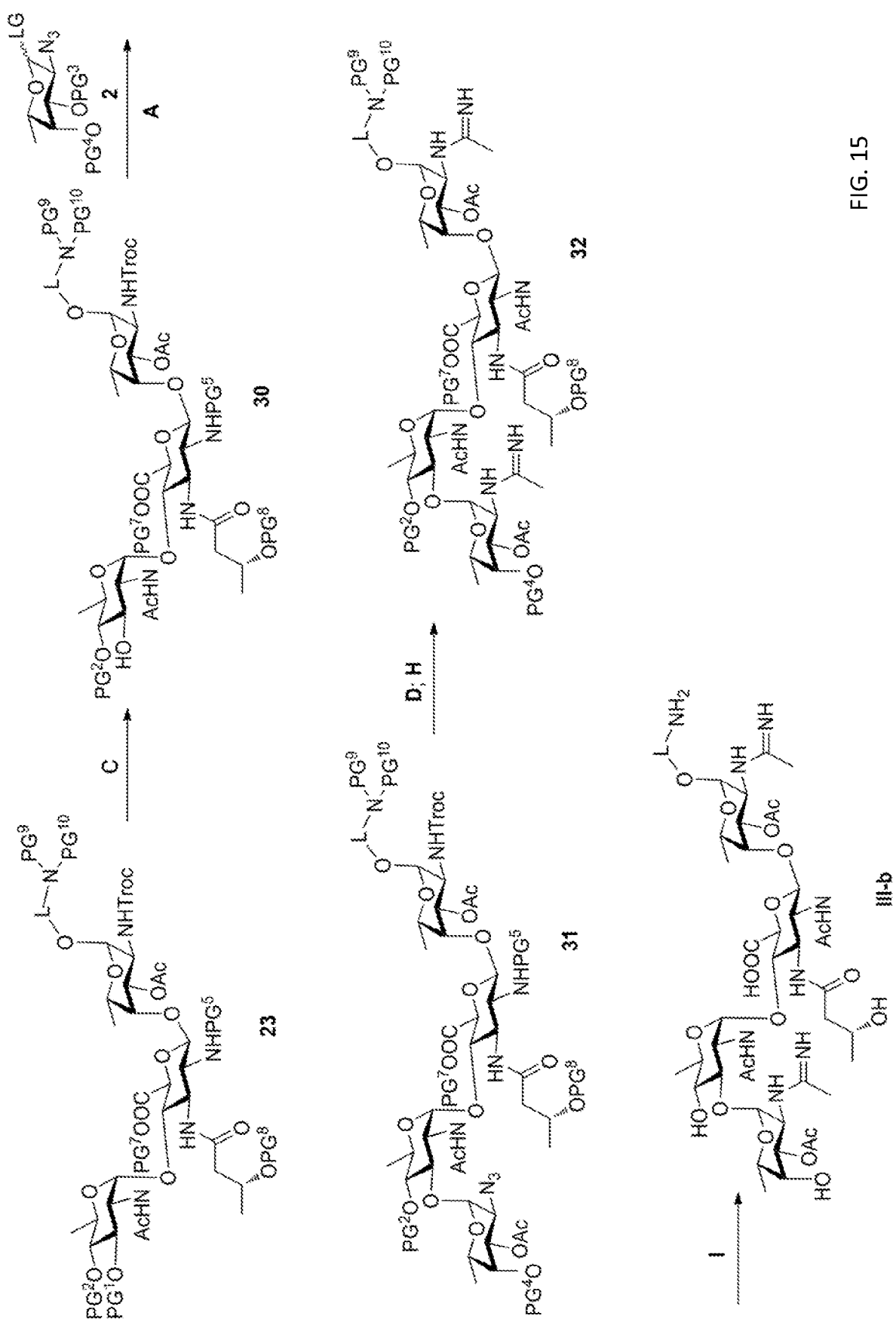
FIG. 15: Synthesis of *Plesiomonas shigelloides* O51 tetrasaccharide III-b.
Figure 16:
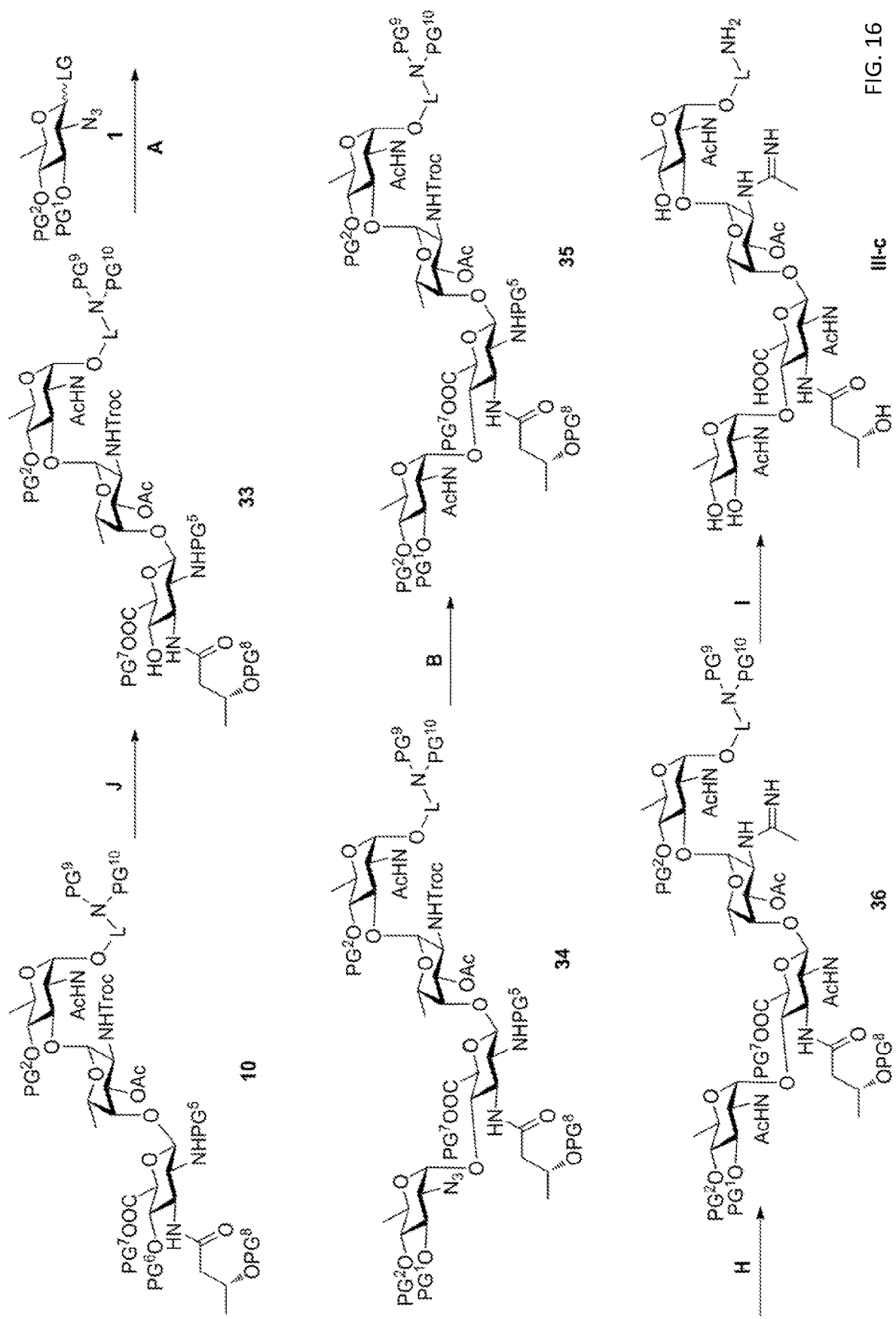
FIG. 16: Synthesis of *Plesiomonas shigelloides* O51 tetrasaccharide III-c.
Figure 17:
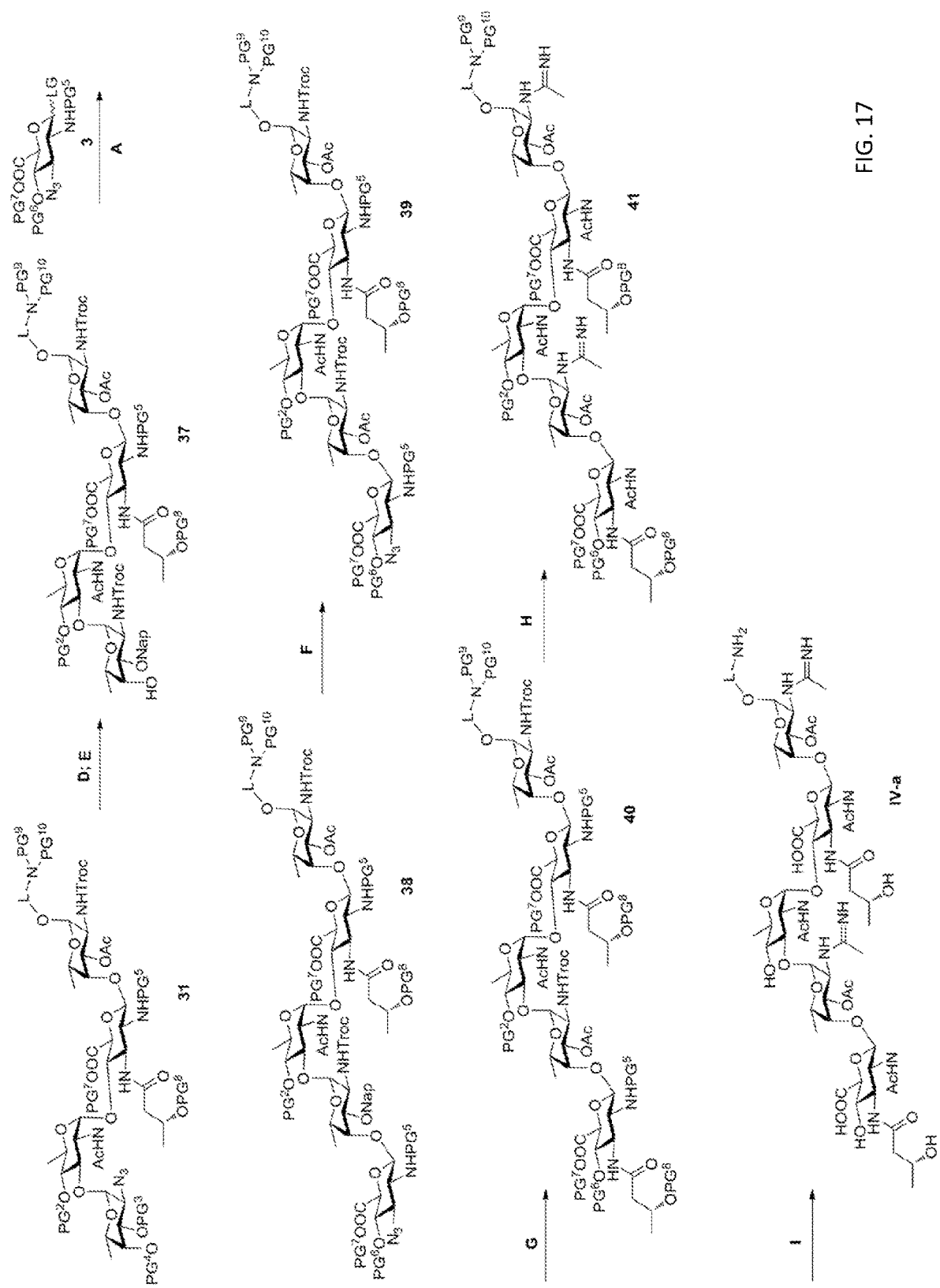
FIG. 17: Synthesis of *Plesiomonas shigelloides* O51 pentasaccharide IV-a.
Figure 18:
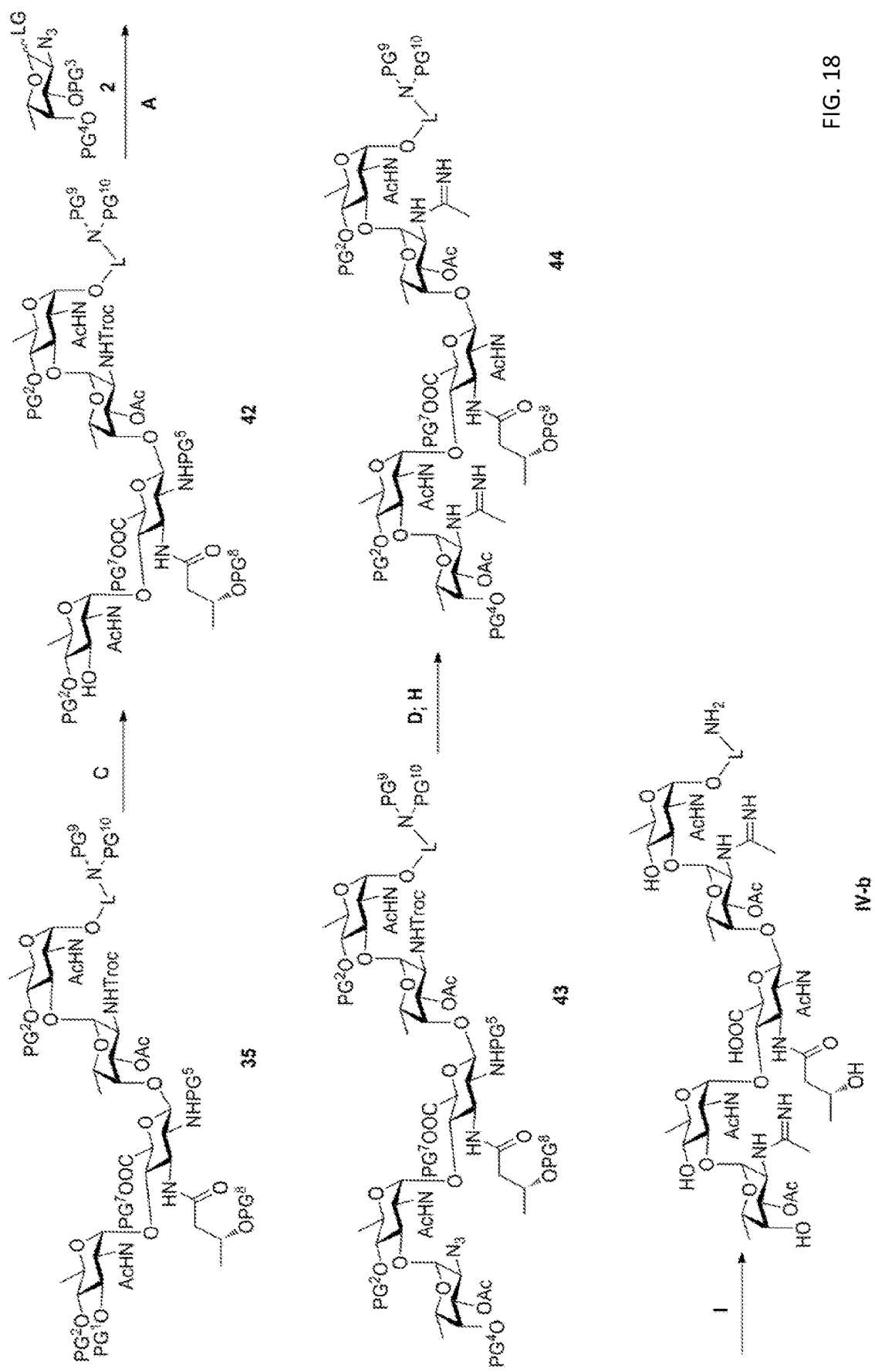
FIG. 18: Synthesis of *Plesiomonas shigelloides* O51 pentasaccharide IV-b.
Figure 19:
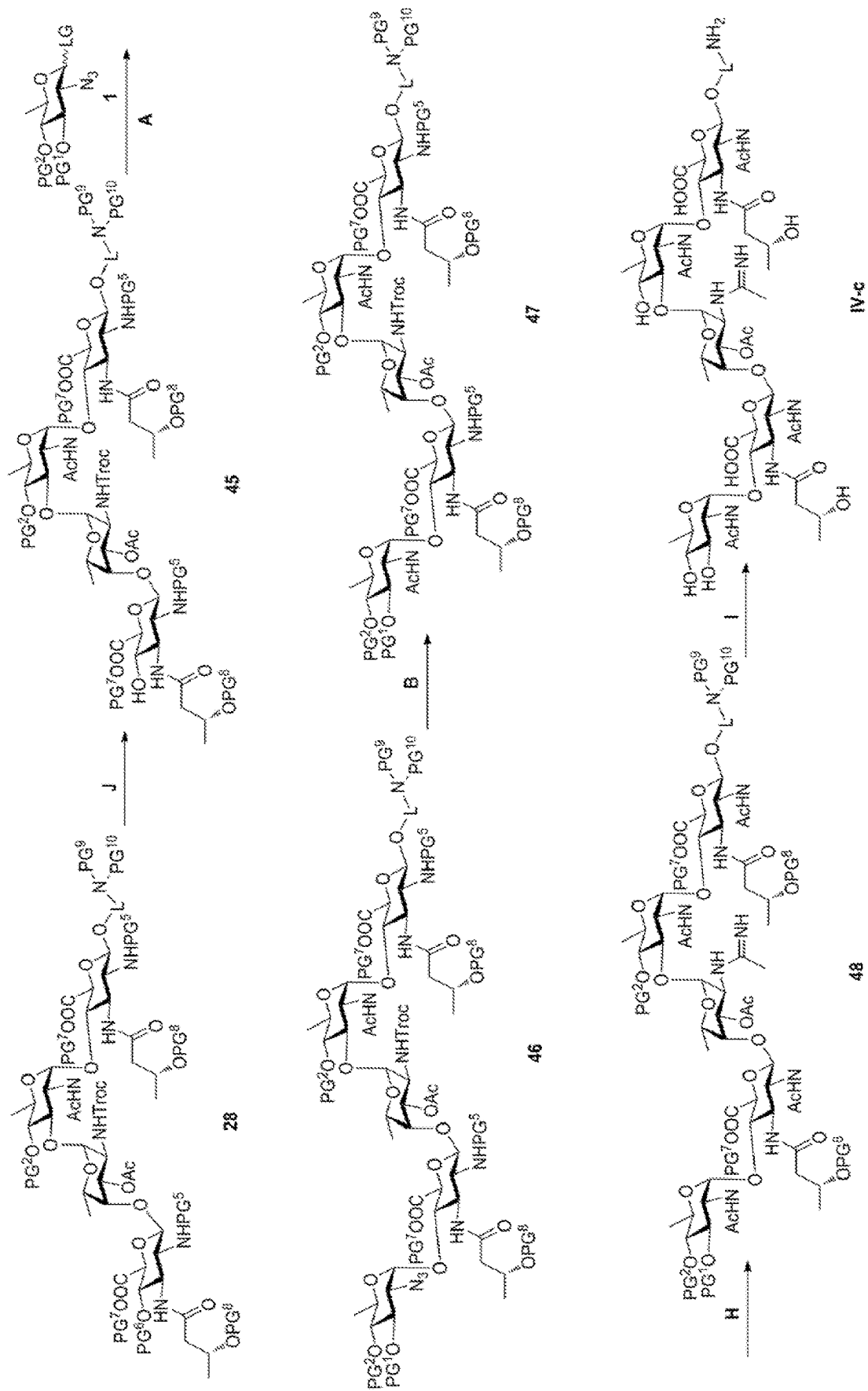
FIG. 19: Synthesis of *Plesiomonas shigelloides* O51 pentasaccharide IV-c.
Figure 20:
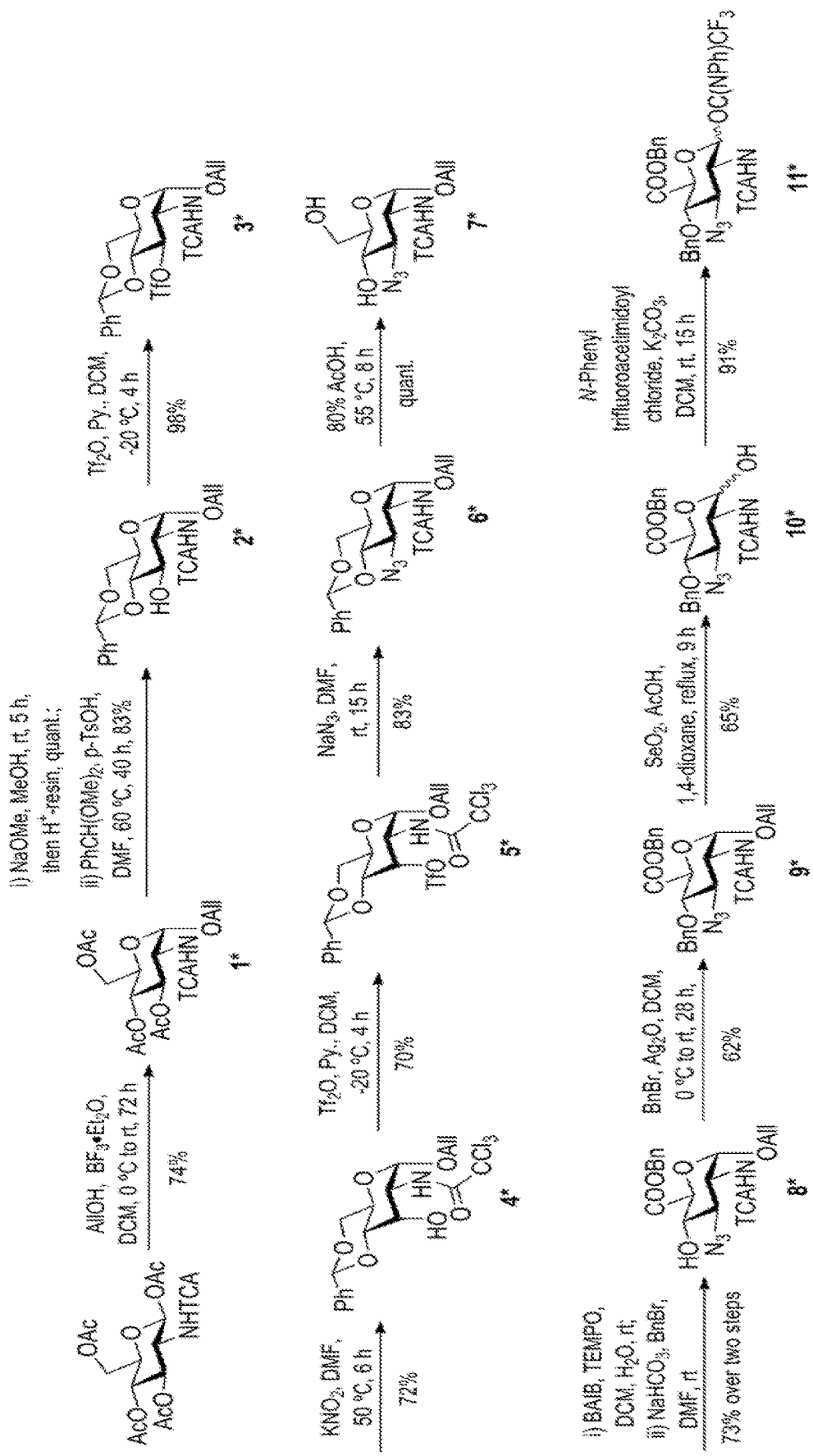
FIG. 20: Chemical synthesis of compound 11*.

A reaction equation is as shown in FIG. 20.

Under argon protection, 1,3,4,6-tetra-O-acetyl-2-deoxy-2-trichloroacetamido-β-D-glucopyranose (M. Virlouvet et al., *Adv. Synth. Catal.* 2010, 352, 2657-2662) (27 g, 0.055 mol) was dissolved in anhydrous dichloromethane (130 mL), and an activated 4 Å molecular sieve and allyl alcohol (18.7 mL, 0.274 mol) were added. After cooling to −5° C., boron trifluoride diethyl ether complex (70 mL, 0.548 mol) was added dropwise. The reaction solution was stirred at 0° C. for 30 min, and then was heated to room temperature to reaction for 71 hours. After the completion of the reaction, the reaction solution was poured onto 200 g of crushed ice, an organic phase obtained by filtration through celite was respectively extracted with water, the saturated sodium bicarbonate solution and the saturated saline solution, and the resulting organic phase was dried with sodium sulfate and then concentrated. The resulting crude product was purified by silica gel column chromatography (petroleum ether/ethyl acetate, 5:1, v/v) to obtain the yellow syrup-like pure product 1* (19.9 g, 0.041 mol, 74%). $[α]_D^{20}$=+87.8° (c=1.20, CHCl$_3$); IR $v_{max}$ (film) 3429, 2960, 1749, 1722, 1517, 1368, 1229, 1048, 822, 682 cm$^{-1}$; $^1$H NMR (400 MHz, CDCl$_3$) δ=6.93 (d, J=9.1 Hz, 1H, NH), 5.88 (dddd, J=17.0, 10.3, 6.5, 5.4 Hz, 1H, CH=C), 5.41-5.23 (m, 3H, 4-H, C=CH$_2$), 5.16 (dd, J=9.8, 9.8 Hz, 1H, 3-H), 5.01 (d, J=3.7 Hz, 1H, 1-H), 4.34-4.19 (m, 3H, 6-CH$_2$, OCH$_a$), 4.11 (dd, J=12.4, 2.4 Hz, 1H, OCH$_b$), 4.09-3.98 (m, 2H, 2-H, 5-H), 2.11 (s, 3H, CH$_3$CO), 2.05 (s, 3H, CH$_3$CO), 2.02 (s, 3H, CH$_3$CO); $^{13}$C NMR (100 MHz, CDCl$_3$) δ=171.1, 170.6, 169.3, 161.9, 132.6, 119.1, 95.5, 92.1, 77.3, 70.7, 69.0, 68.1, 67.8, 61.8, 53.9, 20.7, 20.63, 20.59; HR-ESI-MS (m/z): calcd for C$_{17}$H$_{22}$Cl$_3$NO$_9$Na$^+$ (M+Na$^+$): 512.0258, found: 512.0254.

Embodiment 2

Synthesis of allyl 4,6-O-benzylidene-2-deoxy-2-trichloroacetamido-α-D-glucopyranose (2*)

A reaction equation is as shown in FIG. 20.

Compound 1* (50 g, 0.102 mol) was dissolved in methanol (800 mL), sodium methoxide (2.8 g, 0.051 mol) was added. And then the mixture was stirred at room temperature for 5 hours. After completion of the reaction, the reaction solution was neutralized with an Amberlite IR 120 cation exchange resin, filtered, and concentrated to give desired white solid-like 3,4,6-trihydroxy saccharide (37.1 g, 0.102 mol, quant.).

The trihydroxy saccharide (71 g, 0.195 mol) was further dissolved in 300 mL of anhydrous DMF, and benzaldehyde dimethyl acetal (35 mL, 0.234 mol) and p-toluenesulfonic acid (4.45 g, 0.023 mol) were added. After the reaction solution reacted at 60° C. for 24 hours, methanol generated in the reaction was distilled off under reduced pressure by the rotary evaporator, and the reaction was further carried out at 60° C. This operation was repeated, and DMF was distilled off under reduced pressure after the reaction was completed. The resulting crude product was dissolved in ethyl acetate, extracted with the saturated sodium bicarbonate solution, water and the saturated saline solution, dried with anhydrous sodium sulfate and evaporated to obtain the crude product. The crude product was purified by silica gel column chromatography (petroleum ether:ethyl acetate, 10:1, v/v) to obtain the white solid-like product 2* (73.6 g, 0.163 mol, 83%). $[α]_D^{20}$=+68.6° (c=1.00, CHCl$_3$); IR $v_{max}$ (film) 3339, 2919, 1695, 1530, 1451, 1372, 1085, 1027, 989, 748, 697 cm$^{-1}$; $^1$H NMR (400 MHz, CDCl$_3$) δ=7.55-7.34 (m, 5H, Ph), 6.96 (d, J=8.8 Hz, 1H, NH), 5.86 (dddd, J=16.9, 10.3, 6.4, 5.3 Hz, 1H, CH=C), 5.53 (s, 1H, PhCH), 5.35-5.20 (m, 2H, C=CH$_2$), 4.97 (d, J=3.8 Hz, 1H, 1-H), 4.27 (dd, J=10.2, 4.8 Hz, 1H, 4-H), 4.24-4.11 (m, 2H, 2-H, OCH$_a$), 4.06-3.94 (m, 2H, OCH$_b$, 5-H), 3.86 (dddd, J=9.9, 9.8, 4.7 Hz, 1H, 6-CHa), 3.74 (t, J=10.3 Hz, 1H, 6-CH$_b$), 3.56 (t, J=9.3 Hz, 1H, 3-H), 2.78 (br, 1H, 3-OH); $^{13}$C NMR (100 MHz, CDCl$_3$) δ=162.3, 137.0, 132.9, 129.3, 128.3, 126.3, 118.7, 101.9, 96.3, 92.4, 81.5, 69.7, 68.8, 68.6, 62.8, 55.4; HR-ESI-MS (m/z): calcd for C$_{18}$H$_{20}$Cl$_3$NO$_6$Na$^+$ (M+Na$^+$): 474.0254, found: 474.0245.

Embodiment 3

Synthesis of allyl 4,6-O-benzylidene-3-O-trifluoromethanesulfonyl-2-trichloroacetamido-2-deoxy-α-D-glucopyranose (3*)

A reaction equation is as shown in FIG. 20.

Compound 2* (53.1 g, 0.117 mol) was dissolved in an anhydrous dichloromethane/pyridine mixture (660 mL, 7:1, v/v), cooled to −20° C., followed by dropwise addition of the dichloromethane solution (150 mL) of trifluoromethanesulfonic anhydride (40 mL, 0.234 mol) with stirring, and gradually warmed to 10° C. within 2 hours. After completion of the reaction, the reaction solution was diluted with dichloromethane, and sequentially extracted with 1 M HCl solution, saturated sodium bicarbonate, water and the saturated saline solution. An organic phase was dried with anhydrous sodium sulfate and subjected to reduced pressure distillation at low temperature to remove the solvent. The resulting crude product was purified by silica gel column chromatography (ethyl ether:ethyl acetate, 5:1 to 2:1, v/v) to obtain the yellow syrup-like product 3* (66.5 g, 0.114 mol, 98%). $[α]_D^{20}$=+35.3° (c=1.00, CHCl$_3$); IR $v_{max}$ (film) 3348, 1698, 1529, 1414, 1373, 1203, 1146, 1122, 959, 836, 753, 628 cm$^{-1}$; $^1$H NMR (400 MHz, CDCl$_3$) δ=7.52-7.33 (m, 5H, Ph), 7.06 (d, J=9.6 Hz, 1H, NH), 5.87 (dddd, J=17.0, 10.2, 6.8, 5.4 Hz, 1H, CH=C), 5.62 (s, 1H, PhCH), 5.37-5.27 (m, 2H, C=CH$_2$), 5.13 (dd, J=10.3, 9.1 Hz, 1H, 3-H), 5.03 (d, J=3.7 Hz, 1H, 1-H), 4.50 (ddd, J=10.0, 10.0, 3.8 Hz, 1H, 2-H), 4.36 (dd, J=10.4, 4.5 Hz, 1H, 6-CHa), 4.25 (ddt, J=12.7, 5.5, 1.3 Hz, 1H, OCH$_a$), 4.06 (ddt, J=12.7, 6.8, 1.2 Hz, 1H, OCH$_b$), 3.98 (td, J=9.6, 4.6 Hz, 1H, 5-H), 3.92 (dd, J=9.2 Hz, 1H, 6-CH$_b$), 3.84 (dd, J=10.1, 10.1 Hz, 1H, 4-H); $^{13}$C NMR (100 MHz, CDCl$_3$) δ=162.2, 136.2, 132.2, 129.2, 128.2, 125.9, 119.9, 116.8, 101.6, 96.4, 91.8, 83.1, 78.2, 69.3, 68.4, 63.3, 53.8; HR-ESI-MS (m/z): calcd for C$_{19}$H$_{19}$Cl$_3$F$_3$NO$_8$SNa$^+$ (M+Na$^+$): 605.9747, found: 605.9760.

Embodiment 4

Synthesis of allyl 4,6-O-benzylidene-2-trichloroacetamido-2-deoxy-α-D-allopyranose (4*)

A reaction equation is as shown in FIG. 20.

Compound 3* (0.5 g, 0.855 mmol) was dissolved in anhydrous DMF (10 mL), potassium nitrite (364 mg, 4.275 mmol) was added, and the reaction solution was stirred at 50° C. for 6 hours. After the reaction was completed, the reaction solution was diluted by adding dichloromethane, and extracted with the saturated saline solution. And the resulting organic phase was dried with anhydrous sodium sulfate and concentrated under reduced pressure. The crude product was subjected to silica gel column chromatography (petroleum ether:ethyl acetate, 8:1, v/v) to give the white solid-like 3-position inversion product 4* (278 mg, 0.614 mmol, 72%). $[\alpha]_D^{20}=+74.0°$ (c=1.00, CHCl$_3$); IR $v_{max}$ (film) 3419, 1711, 1507, 1378, 1218, 1102, 1065, 1023, 820, 756, 699 cm$^{-1}$; $^1$H NMR (400 MHz, CDCl$_3$) δ=7.57-7.33 (m, 6H, NH, Ph), 5.88 (dddd, J=16.9, 10.3, 6.4, 5.2 Hz, 1H, CH=C), 5.63 (s, 1H, PhCH), 5.37-5.20 (m, 2H, C=CH$_2$), 5.00 (d, J=4.2 Hz, 1H, 1-H), 4.38 (dd, J=10.3, 5.1 Hz, 1H, 6-CH$_b$), 4.27 (m, 2H, 3-H, OCH$_a$), 4.24-4.16 (m, 2H, 2-H, 5-H), 4.05 (ddt, J=13.0, 6.5, 1.3 Hz, 1H, OCH$_b$), 3.80 (t, J=10.3 Hz, 1H, 6-CHa), 3.67 (dd, J=9.7, 2.8 Hz, 1H, 4-H), 2.66 (br, 1H, 3-OH); $^{13}$C NMR (100 MHz, CDCl$_3$) δ=161.7, 136.9, 132.9, 129.3, 128.4, 126.2, 118.8, 101.9, 96.0, 92.3, 78.1, 77.2, 69.5, 69.0, 67.3, 57.6, 51.2; HR-ESI-MS (m/z): calcd for C$_{18}$H$_{20}$Cl$_3$NO$_6$Na$^+$ (M+Na$^+$): 474.0254, found: 474.0245.

Embodiment 5

Synthesis of allyl 4,6-O-benzylidene-3-O-trifluoromethanesulfonyl-2-trichloroacetamido-2-deoxy-α-D-allopyranose (5*)

A reaction equation is as shown in FIG. 20.

Pyridine (273 μL, 3.380 mmol) was added to an anhydrous dichloromethane (3.93 mL) solution of compound 4* (178 mg, 0.393 mmol) at −20° C., trifluoromethanesulfonic anhydride (133 μL, 0.786 mmol) was further added dropwise, and the reaction temperature was gradually increased to 10° C. during 2 hours of stirring. After the reaction was completed, the reaction solution was diluted with dichloromethane, and the resulting organic phase was extracted with a 1 M HCl solution, the saturated sodium bicarbonate solution, water and the saturated saline solution. The resulting organic phase was dried with anhydrous sodium sulfate and subjected to reduced pressure distillation at low temperature to remove the solvent. The resulting crude product was purified by the silica gel column (petroleum ether:ethyl acetate, 10:1-5:1-2:1, v/v) to give the yellow syrup-like product 5* (160 mg, 0.275 mmol, 70%). $[\alpha]_D^{20}=+40.4°$ (c=1.00, CHCl$_3$); IR $v_{max}$ (film) 2923, 2853, 1750, 1497, 1416, 1211, 1028, 821, 617 cm$^{-1}$; $^1$H NMR (400 MHz, CDCl$_3$) δ=7.53-7.35 (m, 5H, Ph), 7.33 (d, J=8.5 Hz, 1H, NH), 5.89 (dddd, J=16.8, 10.6, 6.0, 4.7 Hz, 1H, CH=C), 5.61 (s, 1H, PhCH), 5.44 (t, J=2.9 Hz, 1H, 3-H), 5.37 (dq, J=17.3, 1.6 Hz, 1H, C=CHa), 5.28 (dq, J=10.5, 1.4 Hz, 1H, C=CH$_b$), 4.96 (d, J=4.3 Hz, 1H, 1-H), 4.44 (ddd, J=8.0, 4.3, 3.2 Hz, 1H, 2-H), 4.41-4.31 (m, 2H, 6-Ha, OCH$_a$), 4.26 (td, J=9.9, 5.2 Hz, 1H, 5-H), 4.05 (ddt, J=13.3, 6.0, 1.4 Hz, 1H, OCH$_b$), 3.87 (dd, J=9.7, 2.5 Hz, 1H, 4-H), 3.78 (t, J=10.4 Hz, 1H, 6-Hb); $^{13}$C NMR (100 MHz, CDCl$_3$) δ=162.0, 136.3, 132.4, 129.4, 128.3, 126.2, 118.1, 102.4, 94.9, 91.5, 80.7, 74.9, 69.0, 68.8, 58.1, 50.2; HR-ESI-MS (m/z): calcd for C$_{19}$H$_{19}$Cl$_3$F$_3$NO$_8$SNa$^+$ (M+Na$^+$): 605.9747, found: 605.9753.

Embodiment 6

Synthesis of allyl 4,6-O-benzylidene-3-azido-2-trichloroacetamido-2,3-dideoxy-α-D-glucopyranose (6*)

A reaction equation is as shown in FIG. 20.

Compound 5* (65 mg, 0.111 mmol) was dissolved in anhydrous DMF, and sodium azide (36 mg, 0.555 mmol) was added and stirred at room temperature overnight. After the completion of the reaction, the reaction solution was diluted with ethyl acetate and extracted with water and the saturated saline solution. The resulting organic phase was dried with anhydrous sodium sulfate and concentrated. The resulting crude product was purified by silica gel column chromatography (petroleum ether:ethyl acetate, 20:1-8:1, v/v) to obtain the white solid-like product 6* (44.2 mg, 0.093 mmol, 83%). $[\alpha]_D^{20}=+39.7°$ (c=1.00, CHCl$_3$); IR $v_{max}$ (film) 3120, 2917, 2849, 2110, 1692, 1528, 1372, 1258, 1124, 1080, 1055, 1016, 836, 750, 697 cm$^{-1}$; $^1$H NMR (400 MHz, CDCl$_3$) δ=7.55-7.33 (m, 5H, Ph), 6.88 (d, J=9.5 Hz, 1H, NH), 5.94-5.80 (m, 1H, CH=C), 5.63 (s, 1H, PhCH), 5.36-5.23 (m, 2H, C=CH$_2$), 4.92 (d, J=3.6 Hz, 1H, 1-H), 4.32 (dd, J=10.4, 4.9 Hz, 1H, 6-CHa), 4.24 (ddt, J=12.7, 5.5, 1.4 Hz, 1H, OCH$_a$), 4.13 (ddd, J=11.2, 9.7, 3.7 Hz, 1H, 2-H), 4.05 (ddt, J=12.8, 6.6, 1.4 Hz, 1H, OCH$_b$), 3.99-3.88 (m, 2H, 3-H, 5-H), 3.79 (t, J=10.3 Hz, 1H, 6-CH$_b$), 3.70 (t, J=9.6 Hz, 1H, 4-H); $^{13}$C NMR (100 MHz, CDCl$_3$) δ=161.9, 136.7, 132.6, 129.1, 128.3, 125.9, 119.2, 101.5, 95.9, 92.3, 80.3, 77.2, 68.9, 68.7, 63.3, 61.2, 53.5; HR-ESI-MS (m/z): calcd for C$_{18}$H$_{19}$Cl$_3$N$_4$O$_5$Na$^+$ (M+Na$^+$): 499.0319, found: 499.0311.

Embodiment 7

Synthesis of allyl 3-azido-2-trichloroacetamido-2,3-dideoxy-α-D-glucopyranose (7*)

A reaction equation is as shown in FIG. 20.

Compound 6* (20 mg, 0.042 mmol) was added to an 80% acetic acid aqueous solution (0.9 mL), heated to 55° C., and stirred until the reaction was completed. The reaction solution was subjected to reduced pressure distillation to remove the solvent, and purified by silica gel column chromatography (dichloromethane:methanol, 60:1-40:1-30:1, v/v) to obtain white solid-like 4,6-dihydroxy saccharide 7* (16.3 mg, 0.042 mmol, quant.). $[\alpha]_D^{20}=+16.9°$ (c=0.35, CHCl$_3$); IR $v_{max}$ (film) 3411, 2924, 2108, 1712, 1517, 1262, 1049, 822, 680 cm$^{-1}$; $^1$H NMR (400 MHz, CD$_3$OD) δ=5.98 (dddd, J=17.0, 10.4, 6.4, 5.1 Hz, 1H, CH=C), 5.38 (dq, J=17.3, 1.7 Hz, 1H, C=CHa), 5.24 (dq, J=10.4, 1.4 Hz, 1H, C=CH$_b$), 4.94 (d, J=3.6 Hz, 1H, 1-H), 4.29 (ddt, J=13.2, 5.2, 1.5 Hz, 1H, OCH$_a$), 4.10 (ddt, J=13.1, 6.4, 1.4 Hz, 1H, OCH$_b$), 3.99 (dd, J=11.5, 9.2 Hz, 1H, 3-H), 3.93-3.81 (m, 2H, 2-H, 6-Ha), 3.81-3.68 (m, 2H, 5-H, 6-Hb), 3.52 (t, J=9.3 Hz, 1H, 4-H); $^{13}$C NMR (100 MHz, CD$_3$OD) δ=166.7, 137.6, 120.8, 98.9, 76.5, 73.7, 72.0, 67.5, 64.8, 58.1; HR-ESI-MS (m/z): calcd for C$_{11}$H$_{15}$Cl$_3$N$_4$O$_5$Na$^+$ (M+Na$^+$): 411.0006, found: 411.0001.

Embodiment 8

Synthesis of benzyl (allyl 3-azido-2,3-dideoxy-2-trichloroacetamido-α-D-glucopyranosid) uronate (8*)

A reaction equation is as shown in FIG. 20.

At 0° C., water (1.4 L), 2,2,6,6-tetramethylpiperidine 1-oxyl (TEMPO) (4.4 g, 0.028 mol) and diacetoxyliodo benzene (BAIB) (45.5 g, 0.141 mol) were added to the dichloromethane (2.8 L) solution of compound 7* (22 g, 0.056 mol). After the reaction solution was stirred at room temperature for 4 hours. After that, the reaction mixture was passed through a pad of silica gel, concentrated and dried under high vacuum. The crude acid was used in the next step without further purification.

The crude carboxylic acid compound was dissolved in anhydrous DMF (2.8 L), sodium bicarbonate (21.4 g, 0.255 mol) and benzyl bromide (50.4 mL, 0.424 mol) were sequentially added, and the resulting reaction solution was stirred at room temperature. After the completion of the reaction, the solvent was distilled off under reduced pressure, and the resulting crude product was purified by silica gel column chromatography (petroleum ether:ethyl acetate, 10:1, v/v) to give the yellow syrup-like benzylglucuronate 8* (20.4 g, 0.041 mol, yield of 73% in two-step reaction). $[?]_D^{20}$=+54.5° (c=1.00, CHCl$_3$); IR v$_{max}$ (film) 3412, 2930, 2110, 1717, 1514, 1264, 1057, 909, 820, 733, 698 cm$^{-1}$; $^1$H NMR (400 MHz, CDCl$_3$) δ=7.43-7.33 (m, 5H, Ph), 6.79 (d, J=9.4 Hz, 1H, NH), 5.86 (dddd, J=17.0, 10.3, 6.6, 5.4 Hz, 1H, CH═C), 5.37-5.20 (m, 4H, PhCH$_2$, C═CH$_2$), 4.97 (d, J=3.6 Hz, 1H, 1-H), 4.31-4.20 (m, 2H, 5-H, OCH$_a$), 4.13-4.00 (m, 2H, 2-H, OCH$_b$), 3.91 (t, J=9.5 Hz, 1H, 4-H), 3.75 (dd, J=11.1, 9.3 Hz, 1H, 3-H), 3.31 (br, 1H, 4-OH); $^{13}$C NMR (100 MHz, CDCl$_3$) δ=169.5, 161.9, 134.8, 132.4, 128.77, 128.75, 128.3, 119.4, 95.6, 92.2, 77.2, 71.2, 70.5, 69.3, 67.8, 63.6, 52.7; HR-ESI-MS (m/z): calcd for C$_{18}$H$_{19}$Cl$_3$N$_4$O$_6$Na$^+$ (M+Na$^+$): 515.0268, found: 515.0264.

Embodiment 9

Synthesis of benzyl (allyl 3-azido-4-O-benzyl-2,3-dideoxy-2-trichloroacetamido-α-D-glucopyranosid) uronate (9*)

A reaction equation is as shown in FIG. 20.

Compound 8* (20.3 g, 0.041 mol) was dissolved in anhydrous dichloromethane (400 mL), and benzyl bromide (49 mL, 0.411 mol) and silver oxide (28.6 g, 0.123 mol) were added sequentially at 0° C. The resulting reaction solution was stirred at 0° C. for 5 hours, and then warmed to room temperature, stirred for 28 hours. After the completion of the reaction was confirmed, the mixture was filtered through celite and then concentrated. The resulting crude product was subjected to silica gel column chromatography (petroleum ether:ethyl acetate, 40:1-10:1, v/v) to obtain the white solid-like product 9* (14.7 g, 0.025 mol, 62%). $[?]_D^{20}$=+66.3° (c=1.00, CHCl$_3$); IR v$_{max}$ (film) 3357, 2935, 2108, 1743, 1713, 1514, 1253, 1185, 1111, 1063, 1028, 820, 750, 697 cm$^{-1}$; $^1$H NMR (400 MHz, CDCl$_3$) δ=7.43-7.10 (m, 10H, 2Ph), 6.81 (d, J=9.6 Hz, 1H, NH), 5.84 (dddd, J=17.0, 10.3, 6.6, 5.4 Hz, 1H, CH═C), 5.32-5.22 (m, 2H, C═CH$_2$), 5.21 (s, 2H, COOCH$_2$Ph), 4.95 (d, J=3.5 Hz, 1H, 1-H), 4.69 (d, J=10.5 Hz, 1H, PhCH$_2$), 4.49 (d, J=10.5 Hz, 1H, PhCH$_2$), 4.35-4.27 (m, 1H, 5-H), 4.24 (ddt, J=12.8, 5.4, 1.4 Hz, 1H, OCH$_a$), 4.17-4.08 (m, 1H, 2-H), 4.04 (ddt, J=12.8, 6.6, 1.2 Hz, 1H, OCH$_b$), 3.83-3.74 (m, 2H, 3-H, 4-H); $^{13}$C NMR (100 MHz, CDCl$_3$) δ=168.4, 161.8, 136.9, 134.9, 132.4, 128.7, 128.59, 128.56, 128.5, 128.4, 128.24, 128.21, 128.14, 128.12, 119.44, 119.39, 95.5, 92.3, 78.2, 75.1, 71.0, 69.1, 67.6, 64.3, 53.0; HR-ESI-MS (m/z): calcd for C$_{25}$H$_{25}$Cl$_3$N$_4$O$_6$Na$^+$ (M+Na$^+$): 605.0737, found: 605.0731.

Embodiment 10

Synthesis of benzyl 3-azido-4-O-benzyl-2,3-dideoxy-2-trichloroacetamido-D-glucopyranosyl uronate (10*)

A reaction equation is as shown in FIG. 20.

Compound 9* (95.8 mg, 0.164 mmol) and acetic acid (28 µL, 0.492 mmol) were dissolved in 1,4-dioxane (2 mL), and then selenium dioxide (91 mg, 0.820 mmol) was added and heated to reflux temperature. After the reaction was completed, the mixture was cooled to room temperature, and triethylamine was added dropwise to quench the reaction. The crude product obtained by concentration was purified by silica gel column chromatography (petroleum ether:ethyl acetate, 8:1-4:1, v/v) to obtain the light yellow solid-like hemiacetal product 10* (58.0 mg, 0.107 mmol, 65%). $[?]_D^{20}$=+33.2° (c=1.00, CHCl$_3$); IR v$_{max}$ (film) 3410, 2944, 2113, 1712, 1518, 1457, 1357, 1264, 1187, 1113, 1068, 822, 752, 698 cm$^{-1}$; $^1$H NMR (400 MHz, CDCl$_3$) δ=7.47-7.06 (m, 10H, 2Ph), 6.92 (d, J=9.5 Hz, 1H, NH), 5.29 (t, J=3.5 Hz, 1H, 1-H), 5.21 (d, J=12.1 Hz, 1H, PhCH$_{a1}$), 5.17 (d, J=12.1 Hz, 1H, PhCH$_{a2}$), 4.70 (d, J=10.5 Hz, 1H, PhCH$_{b1}$), 4.56-4.44 (m, 2H, PhCHb$_2$, 5-H), 4.11 (td, J=9.7, 3.4 Hz, 1H, 2-H), 3.81 (m, 2H, 3-H, 4-H), 3.57 (d, J=3.7 Hz, 1H, 1-OH); $^{13}$C NMR (100 MHz, CDCl$_3$) δ=168.6, 162.1, 136.8, 134.7, 128.8, 128.7, 128.5, 128.3, 128.2, 92.2, 90.9, 78.0, 75.0, 70.8, 67.8, 63.7, 53.1; HR-ESI-MS (m/z): calcd for C$_{22}$H$_{21}$Cl$_3$N$_4$O$_6$Na$^+$ (M+Na$^+$): 567.0395, found: 567.0414.

Embodiment 11

Synthesis of benzyl (3-azido-4-O-benzyl-2,3-dideoxy-2-trichloroacetamido-D-glucopyranosyl 1-(N-phenyl)-2,2,2-trifluoroacetimidate-) uronate (11*)

A reaction equation is as shown in FIG. 20.

Potassium carbonate (12 mg, 0.084 mmol) and N-phenyl trifluoroacetimidoyl chloride (13 µL, 0.084 mmol) were added to an anhydrous dichloromethane (0.4 mL) solution of compound 10* (22.7 mg, 0.042 mmol), and the resulting reaction solution was stirred at room temperature overnight. After the reaction was completed, the organic phase was obtained by filtration, and the crude product obtained after concentration was purified by silica gel column chromatography (n-hexane:ethyl acetate, 18:1, v/v) to give the colorless syrup-like product 11* (27.4 mg, 0.038 mmol, 91%). IR v$_{max}$ (film) 3346, 2112, 1723, 1524, 1317, 1213, 1166, 1090, 823, 752, 697 cm$^{-1}$; $^1$H NMR (400 MHz, CDCl$_3$) δ=7.44 (s, 1H), 7.35-7.11 (m, 20H), 7.03 (q, J=7.5 Hz, 2H), 6.80 (d, J=8.8 Hz, 1H), 6.73 (d, J=7.8 Hz, 2H), 6.68 (d, J=7.8 Hz, 2H), 6.38 (s, 1H), 6.12 (s, 1H), 5.30-5.02 (m, 3H), 4.61 (d, J=10.5 Hz, 1H), 4.56 (d, J=10.6 Hz, 1H), 4.52-4.44 (m, 2H), 4.37 (d, J=7.6 Hz, 1H), 4.24 (s, 1H), 4.07 (dt, J=14.0, 7.2 Hz, 1H), 3.92 (s, 1H), 3.85 (dd, J=13.4, 7.8 Hz, 2H); $^{13}$C NMR (100 MHz, CDCl$_3$) δ=167.4, 167.2, 162.0, 142.5, 136.2, 136.1, 134.7, 134.5, 128.83, 128.77, 128.69, 128.67, 128.64, 128.58, 128.56, 128.5, 128.41, 128.37, 124.8, 124.5, 119.3, 119.1, 75.0, 74.3, 73.8, 72.7, 67.9, 67.8, 62.5, 51.7; HR-ESI-MS (m/z): calcd for $C_{30}H_{25}Cl_3F_3N_5O_6Na^+$ (M+Na$^+$): 738.0691, found: 738.0722.

Embodiment 12

Synthesis of ethyl 2-azido-3,4-di-O-acetyl-2-deoxy-1-thio-L-fucopyranoside (12*)

Figure 21:
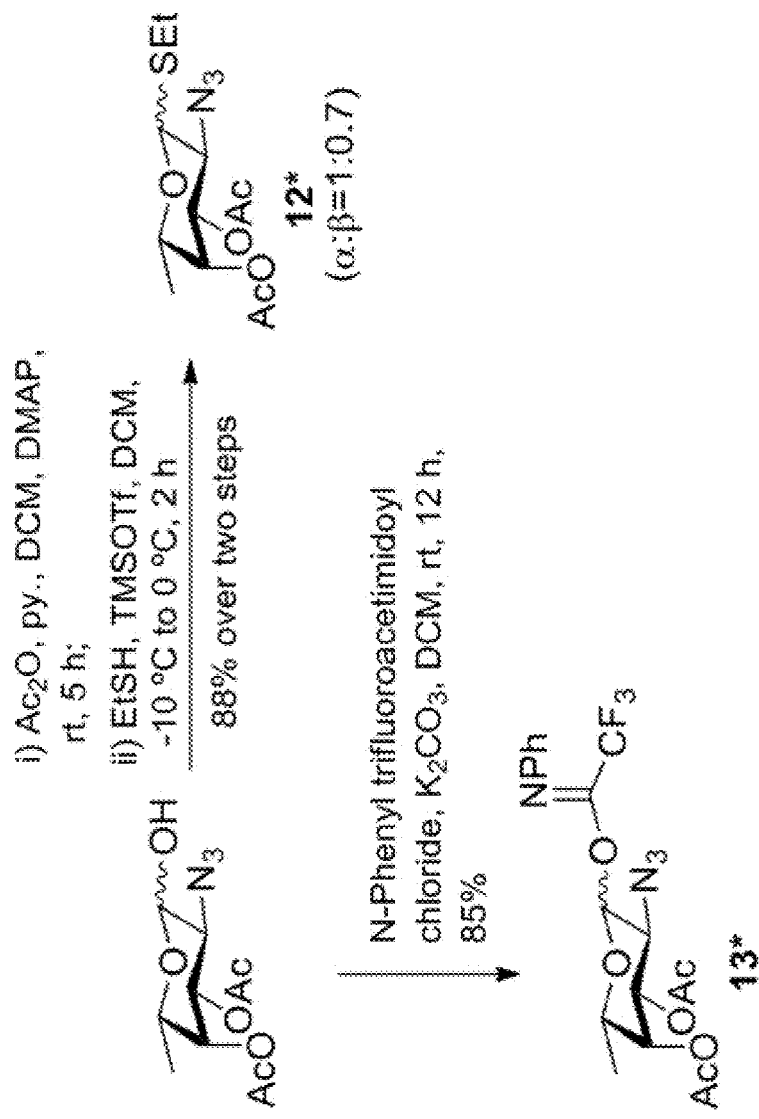
FIG. 21: Chemical synthesis of compounds 12* and 13*.

A reaction equation is as shown in FIG. 21.

2-azido-3,4-di-O-acetyl-2-deoxy-L-fucopyra nose (C. L. Pereira et al., *Angew. Chem. Int. Ed.* 2015, 54, 10016-10019) (44.4 mg, 0.16 mmol) was dissolved in an anhydrous dichloromethane/pyridine mixture (1.6 mL, 4:1, v/v). After cooling to 0° C., acetic anhydride (150 μL, 1.6 mmol) was added dropwise. After the catalytic amount of dimethylaminopyridine was added, the reaction solution was stirred at room temperature. After the completion of the reaction was confirmed, the reaction solution was extracted with the saturated sodium bicarbonate solution, and the resulting organic phase was dried with anhydrous sodium sulfate and concentrated. The resulting crude product was purified by silica gel column chromatography (petroleum ether:ethyl acetate, 10:1, v/v) to obtain 1-O-acetyl saccharide (50.5 mg, 0.16 mmol, quant.).

1-O-acetyl fucose (50.5 mg, 0.16 mmol) and ethanethiol (18 μL, 0.242 mmol) were dissolved in anhydrous dichloromethane (1.6 mL), and an activated 4 Å molecular sieve was added and stirred for 30 minutes. After cooling to −10° C., trimethylsilyl trifluoromethanesulfonate (35 μL, 0.193 mmol) was added, and the resulting reaction solution was stirred at 0° C. After the completion of the reaction was confirmed, the reaction was quenched by the addition of triethylamine, and the solvent is removed by reduced pressure distillation, and the resulting crude product was purified by silica gel column chromatography (petroleum ether:ethyl acetate, 10:1, v/v) to obtain the product 12* (44.0 mg, 0.14 mmol, 88%, ?:?=1:0.7). $^1$H NMR (400 MHz, CDCl$_3$) δ=5.45 (d, J=5.6 Hz, 1H, 1?-H), 5.28 (dd, J=3.4, 1.2 Hz, 1H, 4?-H), 5.26-5.21 (m, 1H, 4β-H), 5.13 (dd, J=11.0, 3.3 Hz, 1H, 3?-H), 4.88 (dd, J=10.2, 3.3 Hz, 1H, 3?-H), 4.49 (qd, J=6.5, 1.3 Hz, 1H, 5?-H), 4.37 (d, J=10.2 Hz, 1H, 1β-H), 4.22 (dd, J=11.0, 5.5 Hz, 1H, 2?-H), 3.82-3.72 (m, 1H, 5β-H), 3.67 (t, J=10.2 Hz, 1H, 2β-H), 2.87-2.71 (m, 2H, ?β-SCH$_2$CH$_3$), 2.61 (dddd, J=20.3, 12.9, 7.4, 5.4 Hz, 2H, ?-SCH$_2$CH$_3$), 2.18 (s, 5H, 2CH$_3$CO), 2.05 (s, 6H, 2CH$_3$CO), 1.34 (t, J=7.4 Hz, 2H, ?β-SCH$_2$CH$_3$), 1.31 (t, J=6.4 Hz, 3H, 1-SCH$_2$CH$_3$), 1.21 (d, J=6.5 Hz, 2H, 6β-CH$_3$), 1.16 (d, J=6.5 Hz, 3H, 6α-CH$_3$).

Embodiment 13

Synthesis of 2-azido-3,4-di-O-acetyl-2-deoxy-L-fucopyranosyl 1-(N-phenyl)-2,2,2-trifluoroacetimidate (13*)

A reaction equation is as shown in FIG. 21.

2-azido-3,4-di-O-acetyl-2-deoxy-L-fucopyra nose (C. L. Pereira et al., *Angew. Chem. Int. Ed.* 2015, 54, 10016-10019) (70 mg, 0.256 mmol) was dissolved in anhydrous dichloromethane (2.6 mL), and potassium carbonate (71 mg, 0.512 mmol) and N-phenyl trifluoroacetimidoyl chloride (77 μL, 0.512 mmol) were added, and stirred at room temperature overnight. After the completion of the reaction, solids were removed by filtration, dichloromethane was used for washing, and the crude product obtained by concentration was purified by silica gel column chromatography (n-hexane: ethyl acetate, 10:1, v/v) to obtain the product 13* (96.7 mg, 0.218 mmol, 85%). $^1$H NMR (400 MHz, CDCl$_3$) δ=7.40-6.75 (m, 5H, Ph), 5.58 (m, 1H, 1-H), 5.20 (m, 1H, 4-H), 4.84 (m, 1H, 3-H), 3.90 (t, J=9.3 Hz, 1H, 2-H), 3.74 (m, 1H, 5-H), 2.20 (s, 3H, CH$_3$CO), 2.07 (s, 3H, CH$_3$CO), 1.21 (d, J=6.4 Hz, 3H, 6-CH$_3$); $^{13}$C NMR (100 MHz, CDCl$_3$) δ=170.3, 169.7, 143.0, 128.8, 124.6, 119.2, 95.7, 71.5, 70.4, 69.1, 59.9, 20.6, 15.9.

Embodiment 14

Synthesis of phenyl 2-azido-3-O-acetyl-4-O-benzyl-2-deoxy-1-seleno-α-D-glucopyranoside (14*)

Figure 22:
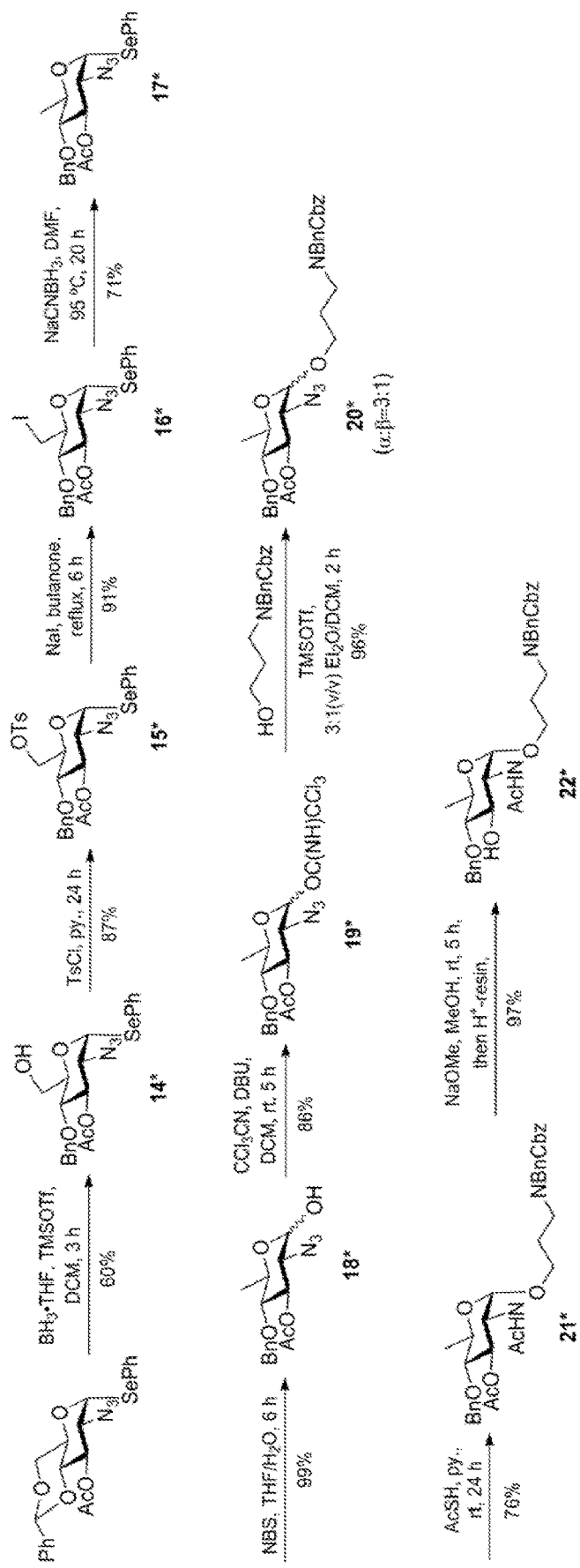
FIG. 22: Chemical synthesis of compound 22*.

A reaction equation is as shown in FIG. 22.

Phenyl 2-azido-3-O-acetyl-4,6-O-benzylidene-2-deoxy-1-seleno-α-D-glucopyranoside (F. Santoyo-Gonzalez et al., *Synlett*, 1994, 6, 454-456) (1 g, 2.1 mmol) and toluene were subjected to azeotropy for three times and dissolved in 18 mL of anhydrous dichloromethane under argon protection. The 1 M borane tetrahydrofuran solution (12.4 mL, 12.4 mmol) was added to the reaction, and after cooling to 0° C., trimethylsilyl trifluoromethanesulfonate (190 μL, 1.05 mmol) was added. The resulting reaction solution was stirred at room temperature. After the completion of the reaction was confirmed by TLC, the reaction solution was diluted with dichloromethane and extracted with the saturated sodium bicarbonate solution. The organic phase was dried with anhydrous sodium sulfate and subjected to reduced pressure distillation and concentration, and the resulting crude product was purified by silica gel column chromatography (n-hexane:ethyl acetate, 4:1, v/v) to obtain the yellow syrup-like compound 14* (148.9 mg, 0.313 mmol). $[?]_D^{20}$=+159.5° (c=1.00, CHCl$_3$); IR $v_{max}$ (film) 3459, 2924, 2106, 1748, 1364, 1228, 1088, 737, 694 cm$^{-1}$; $^1$H NMR (400 MHz, CDCl$_3$) δ=7.70-7.14 (m, 10H, 2Ph), 5.87 (d, J=5.4 Hz, 1H, 1-H), 5.38 (t, J=9.8 Hz, 1H, 3-H), 4.74-4.54 (m, 2H, PhCH$_2$), 4.19 (dt, J=9.9, 2.9 Hz, 1H, 6-CHa), 3.90 (dd, J=10.3, 5.4 Hz, 1H, 2-H), 3.72 (m, 3H, 4-H, 5-H, 6-CH$_b$), 2.04 (s, 3H, CH$_3$CO), 1.64 (dd, J=7.7, 5.2 Hz, 1H, 6-OH); $^{13}$C NMR (100 MHz, CDCl$_3$) δ=169.7, 137.4, 134.9, 129.2, 128.6, 128.2, 128.1, 128.0, 127.9, 84.0, 75.4, 74.7, 74.2, 73.8, 63.0, 61.1, 20.9; HR-ESI-MS (m/z): calcd for $C_{21}H_{23}N_3O_5SeNa^+$ (M+Na$^+$): 500.0701, found: 500.0682.

Embodiment 15

Synthesis of phenyl 2-azido-3-O-acetyl-4-O-benzyl-2-deoxy-6-O-(p-toluenesulfonyl)-1-seleno-α-D-glucopyranoside (15*)

A reaction equation is as shown in FIG. 22.

Compound 14* (7.9 g, 16.6 mmol) was dissolved in anhydrous pyridine (110 mL), and after p-toluensulfonyl chloride (8.0 g, 42 mmol) was added, the reaction solution was stirred at room temperature overnight. After TLC showed that the starting material had been completely converted, the reaction solution was subjected to reduced pressure distillation and concentrated, diluted with dichloromethane, and then extracted with the saturated sodium bicarbonate solution and water. After dehydration with anhydrous sodium sulfate and reduced pressure distillation to remove the solvent, the resulting crude product was purified by silica gel column chromatography (petroleum ether:ethyl acetate, 5:1, v/v) to obtain the yellow syrup-like product 15* (9.06 g, 14.37 mmol, 87%). $[\alpha]_D^{20}$=+123.2° (c=1.00, CHCl$_3$); IR $v_{max}$ (film) 2107, 1749, 1363, 1214, 1176, 1094, 977, 939, 815, 738, 681 cm$^{-1}$; $^1$H NMR (400 MHz, CDCl$_3$) δ=7.83-7.14 (m, 15H, 3Ph), 5.76 (d, J=5.4 Hz, 1H, 1-H), 5.38-5.22 (m, 1H, 3-H), 4.53 (s, 2H, PhCH$_2$), 4.38-4.21 (m, 2H, 5-H, 6-CHa), 4.09-3.97 (m, 1H, 6-CH$_b$), 3.85 (dd, J=10.3, 5.4 Hz, 1H, 2-H), 3.65 (t, J=9.1 Hz, 1H, 4-H), 2.42 (s, 3H, PhCH$_3$), 2.05 (s, 3H, CH$_3$CO); $^{13}$C NMR (100 MHz, CDCl$_3$) δ=169.5, 145.0, 137.0, 134.5, 132.6, 129.8, 129.2, 128.6, 128.2, 128.12, 128.05, 128.0, 127.9, 84.1, 75.3, 74.9, 74.1, 71.3, 67.8, 62.7, 21.7, 20.8; HR-ESI-MS (m/z): calcd for C$_{28}$H$_{29}$N$_3$O$_7$SSeNa$^+$ (M+Na$^+$): 654.0789, found: 654.0795.

Embodiment 16

Synthesis of phenyl 2-azido-3-O-acetyl-4-O-benzyl-2,6-dideoxy-6-iodo-1-seleno-α-D-glucopyranoside (16*)

A reaction equation is as shown in FIG. 22.

Compound 15* (400 mg, 0.64 mmol) and sodium iodide (480 mg, 3.2 mmol) were added to n-butanone (8 mL) and refluxed at 80° C. for 6 hours. After cooling to room temperature, ethyl acetate was added, the mixture was extracted with the 1 M sodium thiosulfate solution and water, and the resulting organic phase was dried with anhydrous sodium sulfate. The crude product obtained by solvent removal by reduced pressure distillation was purified by silica gel column chromatography (n-hexane:ethyl acetate, 10:1, v/v) to obtain the yellow syrup-like product 16* (340 mg, 0.58 mmol, 91%). $[\alpha]_D^{20}$=+170.3° (c=1.20, CHCl$_3$); IR $v_{max}$ (film) 2928, 2108, 1746, 1367, 1226, 1091, 1044, 739, 694 cm$^{-1}$; $^1$H NMR (400 MHz, CDCl$_3$) δ=7.40 (m, 10H, 2Ph), 5.89 (d, J=5.3 Hz, 1H, 1-H), 5.41 (t, J=9.7 Hz, 1H, 3-H), 4.71 (q, J=11.0 Hz, 2H, PhCH$_2$), 3.94 (dd, J=10.3, 5.4 Hz, 1H, 2-H), 3.87 (dt, J=9.1, 3.2 Hz, 1H, 5-H), 3.59 (t, J=9.2 Hz, 1H, 4-H), 3.48 (dd, J=11.1, 3.9 Hz, 1H, 6-CHa), 3.32 (dd, J=11.1, 2.8 Hz, 1H, 6-CH$_b$), 2.06 (s, 3H, CH$_3$CO); $^{13}$C NMR (100 MHz, CDCl$_3$) δ=169.6, 137.2, 134.6, 129.3, 128.7, 128.2, 128.1, 128.0, 127.9, 84.0, 79.9, 75.1, 73.8, 71.3, 62.9, 20.9, 7.3; HR-ESI-MS (m/z): calcd for C$_{21}$H$_{22}$IN$_3$O$_4$SeNa$^+$ (M+Na$^+$): 609.9718, found: 609.9698.

Embodiment 17

Synthesis of phenyl 2-azido-3-O-acetyl-4-O-benzyl-2-deoxy-1-seleno-α-D-quinovopyranoside (17*)

A reaction equation is as shown in FIG. 22.

Compound 16* (150 mg, 0.26 mmol) was dissolved in anhydrous DMF (3.5 mL), and after the addition of sodium cyanoborohydride (82 mg, 1.30 mmol), the reaction solution was heated to 95° C. and stirred overnight. After the reaction was completed, the reaction solution was cooled to room temperature, poured into water and extracted twice with ethyl acetate. An organic phase was washed with water and then dried with anhydrous sodium sulfate, and a crude product obtained by concentration was purified by silica gel column chromatography (toluene) to obtain the white solid-like product 17* (84.4 mg, 0.18 mmol, 71%). $[\alpha]_D^{20}$=+201.3° (c=1.00, CHCl$_3$); IR $v_{max}$ (film) 2925, 2108, 1752, 1367, 1223, 1083, 735, 692 cm$^{-1}$; $^1$H NMR (400 MHz, CDCl$_3$) δ=7.63-7.22 (m, 10H, 2Ph), 5.81 (d, J=5.4 Hz, 1H, 1-H), 5.34 (dd, J=10.3, 9.1 Hz, 1H, 3-H), 4.71-4.51 (m, 2H, PhCH$_2$), 4.26 (dq, J=9.6, 6.2 Hz, 1H, 5-H), 3.91 (dd, J=10.3, 5.4 Hz, 1H, 2-H), 3.26 (t, J=9.4 Hz, 1H, 4-H), 2.04 (s, 3H, CH$_3$CO), 1.26 (d, J=6.2 Hz, 3H, 6-CH$_3$); $^{13}$C NMR (100 MHz, CDCl$_3$) δ=169.6, 137.5, 134.7, 129.1, 128.5, 128.4, 128.03, 127.97, 127.9, 84.1, 81.8, 74.8, 74.1, 69.9, 63.3, 20.9, 17.6; HR-ESI-MS (m/z): calcd for C$_{21}$H$_{23}$N$_3$O$_4$SeNa$^+$ (M+Na$^+$): 484.0751, found: 484.0755.

Embodiment 18

Synthesis of 2-azido-3-O-acetyl-4-O-benzyl-2-deoxy-D-quinovopyranose (18*)

A reaction equation is as shown in FIG. 22.

Compound 17* (4.81 g, 10.5 mmol) was dissolved in the THF/water mixture (25 mL, 1:1, v/v), bromosuccinimide (4.45 g, 25.0 mmol) was added, and the reaction solution was stirred at room temperature for 6 hours. After the reaction was completed, the reaction solution was diluted with dichloromethane, and an organic phase was extracted with the 10% Na$_2$S$_2$O$_3$/1 M NaHCO$_3$ mixture (1:1, v/v). After the solvent was distilled off under reduced pressure, the crude product was purified by silica gel column chromatography (n-hexane:ethyl acetate, 5:1, v/v) to obtain the colorless syrup-like product 18* (3.31 g, 10.0 mmol, 99%). $[\alpha]_D^{20}$=+33.90 (c=1.00, CHCl$_3$); IR $v_{max}$ (film) 3402, 2934, 2111, 1751, 1363, 1227, 1077, 752, 700 cm$^{-1}$; $^1$H NMR (400 MHz, CDCl$_3$) δ=7.40-7.18 (m, 10H, Ph), 5.57 (dd, J=10.3, 9.4 Hz, 1H, 3-H), 5.30 (d, J=3.3 Hz, 1H, 1-H), 5.06 (dd, J=10.2, 9.4 Hz, 1H, 3-H), 4.69 (d, J=8.0 Hz, 1H, 1-H), 4.66-4.54 (m, 4H, PhCH$_2$), 4.13 (dq, J=12.5, 6.2 Hz, 1H, 5'-H), 3.76 (s, 1H, 1-OH), 3.52 (dq, J=12.4, 6.2 Hz, 1H, 5-H), 3.35 (dd, J=10.3, 8.0 Hz, 1H, 2-H), 3.30-3.05 (m, 4H, 2-H, 4-H, 4'-H, 1-OH), 2.05 (s, 6H, CH$_3$CO), 1.34 (d, J=6.2 Hz, 3H, 6-CH$_3$), 1.29 (d, J=6.3 Hz, 3H, 6'-CH$_3$); $^{13}$C NMR (100 MHz, CDCl$_3$) δ=170.01, 169.95, 137.6, 137.4, 128.52, 128.49, 128.0, 127.93, 127.88, 127.8, 95.8, 92.2, 82.1, 81.4, 75.0, 74.8, 73.9, 71.8, 71.6, 66.9, 65.6, 62.3, 20.9, 17.8; HR-ESI-MS (m/z): calcd for C$_{15}$H$_{19}$N$_3$O$_5$Na$^+$ (M+Na$^+$): 344.1222, found: 344.1224.

Embodiment 19

Synthesis of 2-azido-3-O-acetyl-4-O-benzyl-2-deoxy-D-quinovopyranosyl trichloroacetimidate (19*)

A reaction equation is as shown in FIG. 22.

Under nitrogen protection, trichloroacetonitrile (34 μL, 0.34 mmol) and 1,8-diazabicyclo[5.4.0]undec-7-ene (DBU) (0.6 μL, 0.004 mmol) were added into an anhydrous dichloromethane (0.4 mL) solution of compound 18* (11 mg, 0.034 mmol). The resulting reaction solution was stirred at room temperature for 5 hours. After the reaction was completed, the solvent was distilled off under reduced pressure at low temperature, and a resulting crude product was purified by silica gel column chromatography (n-hexane:ethyl acetate, 7:3, v/v, containing 0.5% of triethylamine) to obtain the product 19* (13.6 mg, 0.029 mmol, 86%). $^1$H NMR (400 MHz, CDCl$_3$) δ=9.49 (s, 1H, NH), 7.46-7.23 (m, 5H, Ph), 6.48 (d, J=3.5 Hz, 1H, 1-H), 5.62-5.42 (m, 1H, 3-H), 4.72 (s, 2H, PhCH2), 4.04 (dq, J=12.5, 6.2 Hz, 1H, 5-H), 3.93 (dd, J=10.7, 3.5 Hz, 1H, 2-H), 3.49 (t, J=9.5 Hz, 1H, 4-H), 2.08 (s, 3H, CH$_3$CO), 1.29 (d, J=6.2 Hz, 3H, 6-CH$_3$).

Embodiment 20

Synthesis of N-benzyl-N-benzyloxycarbonyl-3-aminopropyl 2-azido-3-O-acetyl-4-O-benzyl-2-deoxy-D-quinovopyranoside (20*)

A reaction equation is as shown in FIG. 22.

Under nitrogen protection, the trichloroacetimidate saccharide donor 19* (2.48 g, 5.325 mmol) and N-benzyl-N-benzyloxycarbonyl-3-aminopropan-1-ol (H. Ishida et al., *Org. Biomol. Chem.* 2015, 13, 7762-7771) (1.91 g, 6.390 mmol) were dissolved in an anhydrous diethyl ether/anhydrous dichloromethane mixture (130 mL, 3:1, v/v), and an activated molecular sieve (Aw-300) was added and stirred for 30 minutes. After the reaction solution was cooled to −40° C., trimethylsilyl trifluoromethanesulfonate (1.16 mL, 6.390 mmol) was added slowly and dropwise, and the reaction solution was stirred at this temperature until the reaction was completed. After the completion of the reaction, triethylamine was added dropwise to quench the reaction, and after the molecular sieve was removed by filtration, the solvent was distilled off under reduced pressure. A resulting crude product was purified by silica gel column chromatography (petroleum ether:ethyl acetate, 15:1, v/v) to obtain the product 20* (3.1 g, 5.14 mmol, 96%, α:β=3:1). IR ν$_{max}$ (film) 2919, 2107, 1749, 1696, 1454, 1421, 1361, 1222, 1044, 735, 697 cm$^{-1}$; $^1$H NMR (400 MHz, CDCl$_3$) δ=7.44-7.13 (m, 20H, α-3Ph, 6-3Ph), 5.49 (dd, J=10.6, 9.0 Hz, 1H, α3-H), 5.18 (d, J=8.7 Hz, 2.6H, α-PhCH$_2$, 6-PhCH$_2$), 4.98 (s, 0.3H, β3-H), 4.82 (s, 1H, α1-H), 4.61 (m, 2.6H, α-PhCH$_2$, β-PhCH$_2$), 4.57-4.43 (m, 2.6H, α-PhCH$_2$, β-PhCH$_2$), 4.29 (d, J=8.2 Hz, 0.3H, 6l-H), 3.98-3.52 (m, 2.4H, linker-OCH$_a$, α5-H), 3.50-3.26 (m, 4.7H, linker-NCH$_2$, linker-OCH$_b$, β5-H, β2-H), 3.20 (t, J=9.3 Hz, 1.3H, α4-H, β4-H), 3.06 (d, J=10.4 Hz, 1H, α2-H), 2.05 (s, 3H, α-CH$_3$CO), 2.04 (s, 1H, β-CH$_3$CO), 1.86 (d, J=27.9 Hz, 2.7H, linker-CH$_2$), 1.30 (d, J=6.2 Hz, 1H, β6-CH$_3$), 1.26 (d, J=6.1 Hz, 3H, α6-CH$_3$); $^{13}$C NMR (100 MHz, CDCl$_3$) δ=169.9, 169.8, 163.5, 156.7, 156.2, 137.9, 137.8, 137.7, 137.5, 136.8, 128.6, 128.54, 128.52, 128.49, 128.0, 127.93, 127.9, 127.8, 127.4, 101.6, 97.9, 91.9, 82.3, 81.6, 77.2, 74.9, 73.9, 72.0, 71.4, 67.3, 66.9, 66.0, 65.8, 64.6, 61.6, 50.8, 44.8, 43.9, 28.3, 27.9, 20.9, 17.8; HR-ESI-MS (m/z): calcd for C$_{33}$H$_{38}$N$_4$O$_7$Na$^+$ (M+Na$^+$): 625.2638, found: 625.2629.

Embodiment 21

Synthesis of N-benzyl-N-benzyloxycarbonyl-3-aminopropyl 2-acetamido-3-O-acetyl-4-O-benzyl-2-deoxy-α-D-quinovopyranoside (21*)

A reaction equation is as shown in FIG. 22.

Thioacetic acid (0.42 mL) was added to an anhydrous pyridine (0.42 mL) solution of compound 20* (15.0 mg, 0.025 mmol) at 0° C., and the reaction solution was stirred at room temperature overnight. After the reaction was completed, the reaction solution and toluene were subjected to azeotropy to remove the solvent. Then the resulting crude product was purified by silica gel column chromatography (petroleum ether:acetone, 6:1, v/v) to obtain the colorless syrup-like product 21* (11.8 mg, 0.019 mmol, 76%). [α]$_D^{20}$=+53.1° (c=1.00, CHCl$_3$); IR ν$_{max}$ (film) 3343, 2936, 1745, 1696, 1455, 1423, 1366, 1233, 1120, 1048, 737, 700 cm$^{-1}$; $^1$H NMR (400 MHz, CDCl$_3$) δ=7.48-7.01 (m, 15H, 3Ph), 6.51 (d, J=8.9 Hz, 1H, NH), 5.37-5.01 (m, 3H, 3-H, PhCH$_2$), 4.80-4.31 (m, 5H, 1-H, 2PhCH$_2$), 4.24 (m, 1H, 2-H), 3.85-3.51 (m, 3H, 5-H, linker-2H), 3.43-3.13 (m, 3H, 4-H, linker-2H), 1.99 (s, 3H, CH$_3$CO), 1.96 (s, 3H, CH$_3$CO), 1.75 (m, 2H, linker-CH$_2$), 1.27 (d, J=6.2 Hz, 3H, 6-CH$_3$); $^{13}$C NMR (100 MHz, CDCl$_3$) δ=171.1, 156.3, 137.9, 137.6, 136.6, 128.7, 128.5, 128.1, 127.9, 127.8, 127.5, 127.3, 97.2, 81.9, 75.1, 74.0, 67.4, 67.1, 64.1, 52.3, 49.9, 43.2, 27.3, 23.1, 21.0, 17.9; HR-ESI-MS (m/z): calcd for C$_{35}$H$_{42}$N$_2$O$_8$Na$^+$ (M+Na$^+$): 641.2839, found: 641.2828.

Embodiment 22

Synthesis of N-benzyl-N-benzyloxycarbonyl-3-aminopropyl 2-acetamido-4-O-benzyl-2-deoxy-α-D-quinovopyranoside (22*)

A reaction equation is as shown in FIG. 22.

Sodium methoxide (0.3 mg, 0.006 mmol) was added to the methanol (0.5 mL) solution of compound 21* (7 mg, 0.012 mmol), and the resulting reaction solution was stirred at room temperature. After the reaction was completed, the reaction solution was neutralized with an Amberlite IR 120 cation exchange resin, and the organic phase obtained by filtration was distilled off under reduced pressure. The resulting crude product was purified by silica gel column chromatography (petroleum ether:acetone, 4:1, v/v) to obtain the colorless syrup-like product 22* (6.7 mg, 0.0116 mmol, 97%). [α]$_D^{20}$=+27.9° (c=1.10, CHCl$_3$); IR ν$_{max}$ (film) 3325, 2938, 1695, 1544, 1424, 1369, 1235, 1120, 1070, 736, 699 cm$^{-1}$; $^1$H NMR (400 MHz, CDCl$_3$) δ=7.51 (d, J=6.9 Hz, 1H, NH), 7.44-7.12 (m, 15H, 3Ph), 5.22-5.10 (m, 2H, PhCH$_2$), 5.02 (d, J=11.0 Hz, 1H, PhCH$_{a1}$), 4.78-4.63 (m, 2H, PhCH$_{b1}$, PhCH$_{a2}$), 4.50 (d, J=3.6 Hz, 1H, 1-H), 4.26 (d, J=15.9 Hz, 1H, PhCHb$_2$), 4.21 (s, 1H, 3-OH), 4.00 (m, 2H, 2-H, linker-1H), 3.91 (t, J=9.4 Hz, 1H, 3-H), 3.67 (m, 2H, 5-H, linker-1H), 3.21-3.07 (m, 2H, 4-H, linker-1H), 3.00 (dt, J=14.2, 4.5 Hz, 1H, linker-1H), 2.12 (s, 3H, CH$_3$CO), 1.70 (dq, J=9.6, 5.4 Hz, 2H, linker-CH$_2$), 1.25 (d, J=6.2 Hz, 3H, 6-CH$_3$); $^{13}$C NMR (100 MHz, CDCl$_3$) δ=174.1, 156.7, 138.7, 137.3, 136.5, 128.7, 128.5, 128.4, 128.3, 128.2, 127.7, 127.6, 127.3, 96.9, 84.7, 77.3, 76.0, 75.1, 67.5, 66.5, 62.9, 55.3, 49.4, 42.3, 26.9, 22.6, 17.9; HR-ESI-MS (m/z): calcd for C$_{33}$H$_{40}$N$_2$O$_7$Na$^+$ (M+Na$^+$): 599.2733, found: 599.2750.

Embodiment 23

Synthesis of N-benzyl-N-benzyloxycarbonyl-3-aminopropyl 4-O-benzyl-2-acetamido-3-O-(3,4-di-O-acetyl-2-azido-2-deoxy-L-fucopyranosyl)-2-deoxy-α-D-quinovopyranoside (23*)

Figure 23:
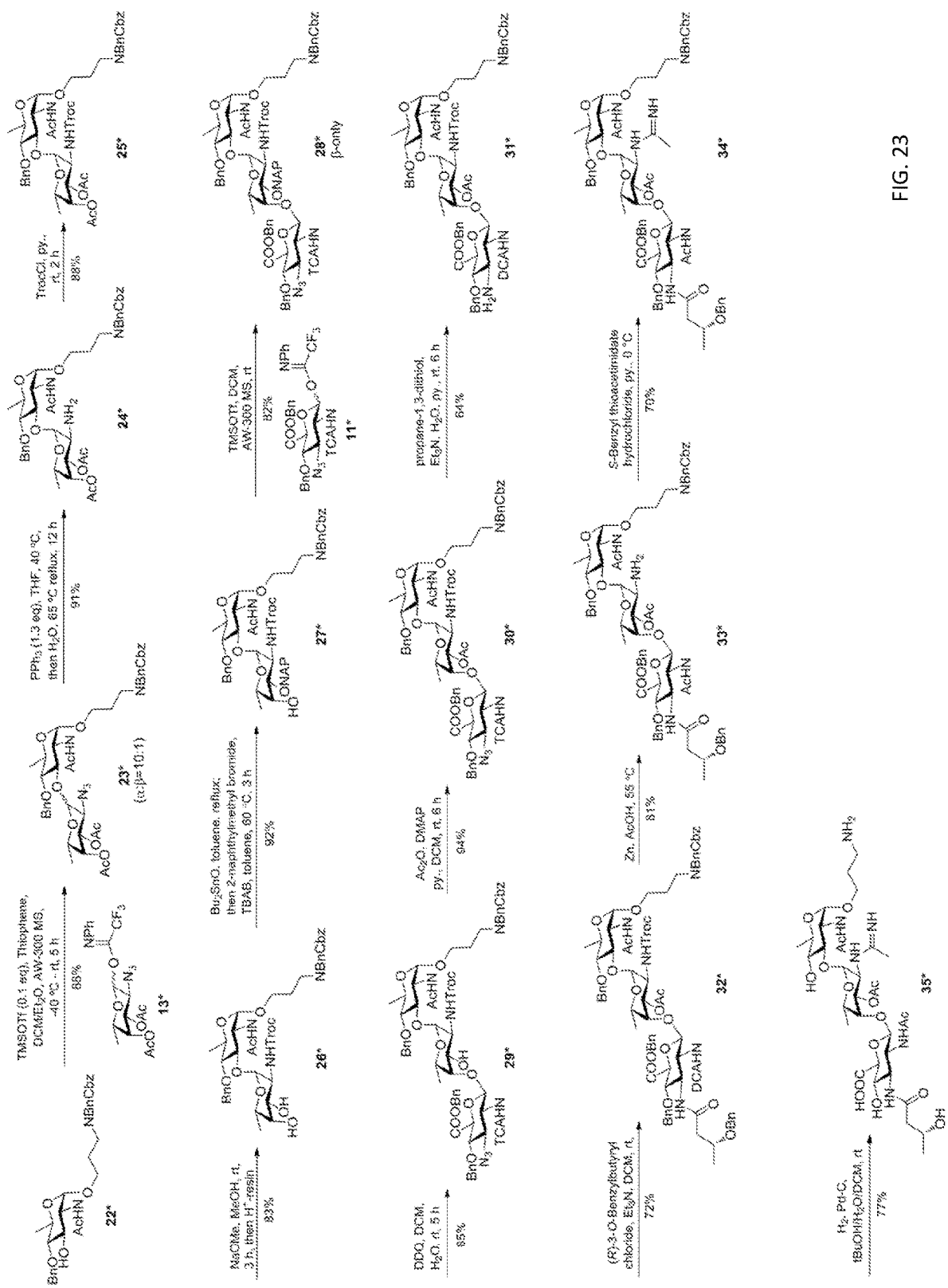
FIG. 23: Chemical synthesis of compound 35*.

A reaction equation is as shown in FIG. 23.

Under nitrogen protection, the trifluoroimidate saccharide donor 13* (159 mg, 0.358 mmol) and the acceptor 22* (207 mg, 0.358 mmol) were dissolved in an anhydrous dichloromethane/anhydrous diethyl ether mixture (12 mL, 1/3, v/v). After thiophene (344 μL, 4.296 mmol) and an activated molecular sieve (AW-300) were added, the resulting reaction solution was stirred at room temperature for 30 minutes. After cooling to −40° C., trimethylsilyl trifluoromethanesulfonate (6.5 μL, 0.036 mmol) was added, and the reaction temperature was gradually increased to room temperature. After the completion of the reaction was confirmed by TLC, triethylamine was added dropwise at 0° C. to quench the reaction, and then the molecular sieve was removed by filtration with celite. After the organic phase was extracted with the saturated sodium bicarbonate solution, the crude product obtained by concentration was purified by silica gel column chromatography (petroleum ether:acetone, 6:1-3:1, v/v) to obtain the desired disaccharide 23* (262 mg, 0.315 mmol, 88%, ?:?=10:1). $[?]_D^{20}$=−178.6° (c=0.90, CHCl$_3$); IR v$_{max}$ (film) 3337, 2936, 2112, 1749, 1680, 1371, 1233, 1044, 975, 751, 700 cm$^{-1}$; $^1$H NMR (400 MHz, CDCl$_3$) δ=7.48-7.08 (m, 15H, 3Ph), 6.79 (d, J=9.3 Hz, 1H, NH), 5.40-5.30 (m, 2H, 1'-H, 3'-H), 5.14 (s, 2H, PhCH$_2$), 5.01 (s, 1H, 4'-H), 4.80-4.69 (m, 2H, PhCH$_2$), 4.60 (m, 2H, 1-H, NCH$_a$Ph), 4.40 (m, 2H, NCH$_b$Ph, 2-H), 4.30-4.18 (m, 1H, 5'-H), 3.96 (dd, J=19.8, 9.9 Hz, 1H, 3-H), 3.80 (dd, J=9.1, 6.3 Hz, 1H, 5-H), 3.70-3.62 (m, 2H, OCH$_a$CCH$_a$N), 3.58 (dd, J=11.4, 2.9 Hz, 1H, 2'-H), 3.29 (dd, J=10.3, 4.7 Hz, 2H, OCH$_b$CCH$_b$N), 3.21 (t, J=9.3 Hz, 1H, 4-H), 2.11 (s, 3H, CH$_3$CO), 2.06 (s, 3H, CH$_3$CO), 2.03 (s, 3H, CH$_3$CO), 1.74 (s, 2H, OCCH$_2$CN), 1.34 (d, J=6.2 Hz, 3H, 6-CH$_3$), 0.71 (d, J=6.4 Hz, 3H, 6'-CH$_3$); $^{13}$C NMR (100 MHz, CDCl$_3$) δ=170.4, 169.8, 156.4, 137.7, 137.5, 136.5, 128.7, 128.6, 128.5, 128.1, 128.0, 127.8, 127.7, 127.5, 127.2, 97.8, 97.5, 83.6, 75.7, 75.5, 70.7, 68.4, 67.6, 67.4, 64.9, 63.9, 57.8, 53.4, 49.8, 43.0, 27.3, 23.1, 20.8, 20.7, 18.2, 15.5; HR-ESI-MS (m/z): calcd for C$_{43}$H$_{53}$N$_5$O$_{12}$Na$^+$ (M+Na$^+$): 854.3588, found: 854.3582.

Embodiment 24

Synthesis of N-benzyl-N-benzyloxycarbonyl-3-aminopropyl 2-acetamido-4-O-benzyl-3-O-(2-amino-3,4-di-O-acetyl-2-deoxy-α-L-fucopyranosyl)-2-deoxy-α-D-quinovopyranoside (24*)

A reaction equation is as shown in FIG. 23.

Compound 23* (253 mg, 0.304 mmol) and triphenylphosphine (104 mg, 0.395 mmol) were dissolved in 5 mL of tetrahydrofuran, and the reaction solution was stirred at 40° C. After the complete reaction of the materials was confirmed by TLC, water (66 μL, 3.65 mmol) was added to the reaction solution. The reaction was heated to reflux at 65° C. After the reaction was completed, the solvent was distilled off under reduced pressure, and the resulting crude product was purified by silica gel column chromatography (dichloromethane:methanol, 40:1, v/v) to obtain the colorless syrup-like amino compound 24* (224 mg, 0.278 mmol, 91%). $[?]_D^{20}$=−55.0° (c=1.10, CHCl$_3$); IR v$_{max}$ (film) 3332, 2937, 1744, 1676, 1424, 1369, 1225, 1132, 1072, 1029, 972, 750, 699 cm$^{-1}$; $^1$H NMR (400 MHz, CDCl$_3$) δ=7.49-7.12 (m, 15H, 3Ph), 7.08 (d, J=9.1 Hz, 1H, NH), 5.25-5.07 (m, 3H, 1'-H, PhCH$_2$), 4.99 (dd, J=11.0, 3.0 Hz, 1H, 3'-H), 4.93 (s, 1H, 4'-H), 4.83-4.66 (m, 2H, PhCH$_2$), 4.60 (d, J=15.8 Hz, 1H, NCH$_a$Ph), 4.53 (d, J=2.9 Hz, 1H, 1-H), 4.49-4.28 (m, 2H, NCH$_b$Ph, 2-H), 4.27-4.10 (m, 1H, 5'-H), 4.00 (t, J=9.7 Hz, 1H, 3-H), 3.82 (dd, J=9.0, 6.3 Hz, 1H, 5-H), 3.68 (ddd, J=15.0, 12.0, 6.1 Hz, 2H, OCH$_a$CCH$_a$N), 3.30 (d, J=7.7 Hz, 2H, OCH$_b$CCH$_b$N), 3.23-3.09 (m, 2H, 4-H, 2'-H), 2.07 (s, 3H, CH$_3$CO), 2.03 (s, 6H, 2CH$_3$CO), 1.74 (s, 2H, OCCH$_2$CN), 1.59 (s, 2H, NH$_2$), 1.35 (d, J=6.1 Hz, 3H, 6-CH$_3$), 0.61 (d, J=6.3 Hz, 3H, 6'-CH$_3$); $^{13}$C NMR (100 MHz, CDCl$_3$) δ=170.5, 137.7, 137.4, 128.6, 128.5, 128.0, 127.8, 127.7, 127.5, 127.2, 99.6, 97.6, 83.3, 77.2, 75.6, 75.0, 71.8, 70.7, 67.7, 67.4, 64.4, 63.6, 53.7, 49.7, 49.2, 42.9, 27.2, 23.3, 20.9, 20.6, 18.2, 15.6; HR-ESI-MS (m/z): calcd for C$_{43}$H$_{55}$N$_3$O$_{12}$Na$^+$ (M+Na$^+$): 828.3683, found: 828.3733.

Embodiment 25

Synthesis of N-benzyl-N-benzyloxycarbonyl-3-aminopropyl 2-acetamido-4-O-benzyl-3-O-(3,4-di-O-acetyl-2-(2,2,2-trichloroethoxycarbonyl)amino-2-deoxy-α-L-fucopyranosyl)-2-deoxy-α-D-quinovopyranoside (25*)

A reaction equation is as shown in FIG. 23.

Compound 24* (224 mg, 0.278 mmol) was dissolved in anhydrous pyridine (7 mL), and 2,2,2-trichloroethoxycarbonyl chloride (96 μL, 0.695 mmol) was added slowly and dropwise at 0° C. The reaction solution was stirred at room temperature, and after the reaction was completed, the reaction was quenched by adding 3.5 mL of methanol. The solvent was distilled off under reduced pressure, the resulting crude product was dissolved in dichloromethane and extracted with water, and the organic phase was dried with anhydrous sodium sulfate and concentrated. The crude product was purified by silica gel column chromatography (petroleum ether:acetone, 7:1, v/v) to obtain the colorless syrup-like product 25* (239 mg, 0.244 mmol, 88%). $[?]_D^{20}$=−34.1° (c=1.00, CHCl$_3$); IR v$_{max}$ (film) 3322, 2938, 1744, 1679, 1522, 1425, 1369, 1225, 1077, 1045, 740, 700 cm$^{-1}$; $^1$H NMR (400 MHz, CDCl$_3$) δ=7.48-7.07 (m, 15H, 3Ph), 6.89 (d, J=8.9 Hz, 1H, NH), 5.45 (d, J=9.2 Hz, 1H, N'H), 5.21 (d, J=2.8 Hz, 1H, 1'-H), 5.13 (m, 3H, 3'-H, PhCH$_2$), 5.00 (d, J=11.9 Hz, 1H, Troc-CHa), 4.81 (m, 2H, 4'-H, PhCH$_a$), 4.59 (m, 3H, PhCH$_a$, PhCH$_b$, Troc-CH$_b$), 4.45 (s, 1H, 1-H), 4.43-4.28 (m, 2H, 2-H, PhCH$_b$), 4.27-4.07 (m, 2H, 2'-H, 5'-H), 3.96 (t, J=9.5 Hz, 1H, 3-H), 3.87-3.68 (m, 2H, 5-H, OCCCH$_a$N), 3.69-3.54 (m, 1H, OCH$_a$CCN), 3.19 (m, 3H, OCH$_b$CCH$_b$N, 4-H), 2.09 (s, 3H, CH$_3$CO), 1.96 (s, 6H, 2CH$_3$CO), 1.72 (m, 2H, OCCH$_2$CN), 1.35 (d, J=6.1 Hz, 3H, 6-CH$_3$), 0.58 (d, J=6.3 Hz, 3H, 6'-CH$_3$); $^{13}$C NMR (100 MHz, CDCl$_3$) δ=171.0, 170.5, 156.4, 154.9, 137.5, 137.4, 136.4, 128.7, 128.53, 128.46, 128.1, 128.0, 127.7, 127.4, 127.2, 97.7, 97.2, 83.3, 77.2, 75.8, 74.7, 74.5, 70.5, 68.9, 67.8, 67.4, 64.9, 63.5, 53.3, 49.7, 49.4, 42.8, 27.1, 23.0, 20.73, 20.65, 18.2, 15.4; HR-ESI-MS (m/z): calcd for C$_{46}$H$_{56}$Cl$_3$N$_3$O$_{14}$Na$^+$ (M+Na$^+$): 1002.2726, found: 1002.2787.

Embodiment 26

Synthesis of N-benzyl-N-benzyloxycarbonyl-3-aminopropyl 2-acetamido-4-O-benzyl-3-O-(2-(2,2,2-trichloroethoxycarbonyl)amino-2-deoxy-α-L-fucopyranosyl)-2-deoxy-α-D-quinovopyranoside (26*)

A reaction equation is as shown in FIG. 23.

Sodium methoxide (6.6 mg, 0.122 mmol) was added to the methanol (8 mL) solution of compound 25* (239 mg, 0.244 mmol), and stirred at room temperature until the reaction was completed. The reaction solution was neutralized with an Amberlite IR 120 cation exchange resin, and the resulting crude product was purified by silica gel column chromatography (petroleum ether:acetone, 4:1, v/v) to obtain the white solid-like product 26* (181 mg, 0.202 mmol, 83%). $[?]_D^{20}$=+6.4° (c=1.00, CHCl$_3$); IR v$_{max}$ (film) 3331, 2934, 1679, 1533, 1456, 1225, 1042, 818, 737, 699 cm$^{-1}$; $^1$H NMR (400 MHz, CDCl$_3$) δ=7.40-7.14 (m, 15H, 3Ph), 7.12 (d, J=9.1 Hz, 1H, NH), 6.19 (d, J=6.7 Hz, 1H, N'H), 5.13 (m, 3H, 1'-H, PhCH$_2$), 4.77 (m, 3H, Troc-CH$_2$, PhCH$_a$), 4.60 (m, 2H, PhCH$_a$, PhCH$_b$), 4.44 (s, 1H, 1-H), 4.35 (m, 2H, 2-H, PhCH$_b$), 4.15-4.01 (m, 2H, 5'-H, 3'-OH), 3.96 (m, 2H, 3-H, 2'-H), 3.83 (m, 3H, OCCCH$_a$N, 5-H, 3'-H), 3.69-3.55 (m, 1H, OCH$_a$CCN), 3.36 (s, 1H, 4'-H), 3.33-3.05 (m, 3H, OCH$_b$CCH$_b$N, 4-H), 2.60 (s, 1H, 4'-OH), 2.00 (s, 3H, CH$_3$CO), 1.72 (m, 2H, OCCH$_2$CN), 1.32 (d, J=6.1 Hz, 3H, 6-CH$_3$), 0.82 (d, J=6.4 Hz, 3H, 6'-CH$_3$); $^{13}$C NMR (100 MHz, CDCl$_3$) δ=172.0, 157.5, 156.5, 137.7, 137.3, 136.4, 128.7, 128.5, 128.4, 128.1, 127.8, 127.7, 127.5, 127.2, 127.1, 97.7, 96.9, 95.5, 83.2, 77.2, 75.4, 74.8, 74.7, 71.5, 71.0, 67.8, 67.4, 65.6, 63.3, 53.6, 51.8, 49.6, 42.6, 27.0, 23.0, 18.1, 15.7; HR-ESI-MS (m/z): calcd for C$_{42}$H$_{52}$Cl$_3$N$_3$O$_{12}$Na$^+$ (M+Na$^+$): 918.2514, found: 918.2558.

Embodiment 27

Synthesis of N-benzyl-N-benzyloxycarbonyl-3-aminopropyl 2-acetamido-4-O-benzyl-3-O-(3-O-(2-naphthyl)methyl-2-(2,2,2-trichloroethoxycarbonyl)amino-2-deoxy-α-L-fucopyranosyl)-2-deoxy-α-D-quinovopyranoside (27*)

A reaction equation is as shown in FIG. 23.

Compound 26* (200 mg, 0.223 mmol) and toluene were subjected to azeotropy to remove water and then were vacuumized for half an hour. Under the protection of nitrogen, the mixture was dissolved in 3.2 mL of anhydrous toluene, and dibutyltin oxide (83 mg, 0.335 mmol) and an activated 4 Å molecular sieve were added. The reaction solution was heated to reflux for 1 hour and cooled to room temperature, naphthylmethylene bromine (148 mg, 0.669 mmol) and tetrabutylammonium bromide (108 mg, 0.335 mmol) were added, and the reaction solution was heated to 60° C. and stirred for 3 hours. After the reaction was completed, the reaction solution was filtered and concentrated, and the resulting crude product was purified by silica gel column chromatography (petroleum ether:acetone, 7:1, v/v) to obtain the white solid-like product 27* (212 mg, 0.204 mmol, 92%). [?]$_D^{20}$=–14.2° (c=1.00, CHCl$_3$); IR ν$_{max}$ (film) 3013, 2932, 1735, 1670, 1515, 1454, 1215, 1091, 1053 cm$^{-1}$; $^1$H NMR (400 MHz, CDCl$_3$) δ=7.93-6.95 (m, 22H, Ar-22H), 6.88 (d, J=9.5 Hz, 1H, 2-NH), 5.43 (d, J=9.7 Hz, 1H, 2'-NH), 5.27-5.09 (m, 3H, 1'-H, CH$_2$), 5.05 (d, J=12.1 Hz, 1H, CH$_2$-1H), 4.86-4.69 (m, 2H, CH$_2$), 4.65-4.51 (m, 3H, NCH$_a$Ph, CH$_2$), 4.45 (d, J=3.5 Hz, 1H, 1-H), 4.34 (m, 3H, NCH$_b$Ph, CH$_2$-1H, 2-H), 4.20 (ddd, J=10.2, 10.2, 3.6 Hz, 1H, 2'-H), 4.01-3.84 (m, 2H, 5'-H, 3-H), 3.83-3.70 (m, 2H, 5-H, linker-1H), 3.69-3.60 (m, 1H, linker-1H), 3.57 (dd, J=10.7, 3.0 Hz, 1H, 3'-H), 3.43 (s, 1H, 4'-H), 3.26 (d, J=9.1 Hz, 1H, linker-1H), 3.20-3.10 (m, 1H, linker-1H), 3.04 (t, J=9.2 Hz, 1H, 4-H), 2.38 (s, 1H, 4'-OH), 1.91 (s, 3H, CH$_3$CO), 1.71 (t, J=6.2 Hz, 2H, linker-CH$_2$), 1.27 (d, J=6.9 Hz, 3H, 6-CH$_3$), 0.85 (d, J=6.5 Hz, 3H, 6'-CH$_3$); $^{13}$C NMR (100 MHz, CDCl$_3$) δ=171.2, 156.4, 155.0, 137.6, 137.4, 136.4, 135.1, 133.1, 128.7, 128.5, 128.3, 128.1, 127.9, 127.8, 127.7, 127.5, 127.2, 127.0, 126.7, 126.4, 126.2, 125.7, 97.9, 97.7, 95.8, 83.4, 77.2, 76.1, 75.2, 75.0, 74.6, 71.8, 68.8, 67.7, 67.4, 65.7, 63.5, 53.4, 50.1, 49.7, 42.7, 27.1, 23.1, 18.1, 15.8; HR-ESI-MS (m/z): calcd for C$_{53}$H$_{60}$Cl$_3$N$_3$O$_{12}$Na$^+$ (M+Na$^+$): 1058.3140, found: 1058.3133.

Embodiment 28

Synthesis of N-benzyl-N-benzyloxycarbonyl-3-aminopropyl 2-acetamido-4-O-benzyl-3-O-(4-O-[benzyl 3-azido-4-O-benzyl-2,3-dideoxy-2-trichloroacetamido-6-D-glucopyranosyl uronate]-3-O-(2-naphthyl)methyl-2-(2,2,2-trichloroethoxycarbonyl)amino-2-deoxy-α-L-fucopyranosyl)-2-deoxy-α-D-quinovopyranoside (28*)

A reaction equation is as shown in FIG. 23.

Under the protection of nitrogen, the trifluoroacetimidate saccharide donor 11* (69 mg, 0.096 mmol) and the disaccharide receptor 27* (20 mg, 0.019 mmol) were dissolved in 3.2 mL of anhydrous dichloromethane, and the activated molecular sieve (Aw-300) was added and stirred at room temperature for 30 minutes. After trimethylsilyl trifluoromethanesulfonate (1.8 μL, 0.01 mmol) was added at room temperature, the reaction solution was continuously stirred at room temperature. After the completion of the reaction, the reaction was quenched by the addition of 4 drops of pyridine at 0° C., and the organic phase obtained by filtration was extracted with the saturated sodium bicarbonate solution and subjected to reduced pressure distillation to remove the solvent. The crude product was purified by silica gel column chromatography (petroleum ether: acetone, 6:1, v/v) to obtain the desired white solid-like trisaccharide 28* (24.6 mg, 0.016 mmol, 82%, 0-only). [?]$_D^{20}$=–22.9° (c=1.00, CHCl$_3$); IR ν$_{max}$ (film) 3016, 2107, 1743, 1676, 1516, 1454, 1265, 1216, 1092, 1047, 752, 699 cm$^{-1}$; $^1$H NMR (400 MHz, CDCl$_3$) δ=7.91-7.07 (m, 33H, 2''-NH, Ar-32H), 6.81 (d, J=9.4 Hz, 1H, 2-NH), 5.37 (d, J=9.9 Hz, 1H, 2'-NH), 5.22-5.05 (m, 6H, 2CH$_2$, 1'-H, 1''-H), 5.01 (d, J=12.0 Hz, 1H, CH$_2$-1H), 4.78 (d, J=11.2 Hz, 1H, CH$_2$-1H), 4.70-4.52 (m, 6H, 5CH$_2$-1H, 3''-H), 4.51-4.40 (m, 3H, 2CH$_2$-1H, 1-H), 4.40-4.26 (m, 2H, CH$_2$-1H, 2-H), 4.20 (ddd, J=10.9, 10.6, 3.5 Hz, 1H, 2'-H), 4.04 (d, J=9.7 Hz, 1H, 5''-H), 3.97 (t, J=6.2 Hz, 1H, 5'-H), 3.88 (t, J=9.7 Hz, 1H, 3-H), 3.80 (s, 1H, 4'-H), 3.78-3.67 (m, 2H, linker-1H, 5-H), 3.66-3.54 (m, 2H, linker-1H, 3'-H), 3.50 (t, J=9.4 Hz, 1H, 4''-H), 3.34-3.11 (m, 3H, linker-2H, 2''-H), 3.06 (t, J=9.3 Hz, 1H, 4-H), 1.98 (s, 3H, CH$_3$CO), 1.74 (s, 2H, linker-CH$_2$), 1.30-1.18 (d, J=5.3 Hz, 3H, 6-CH$_3$), 0.80 (d, J=6.6 Hz, 3H, 6'-CH$_3$); $^{13}$C NMR (100 MHz, CDCl$_3$) δ=171.2, 167.7, 162.4, 156.4, 154.6, 137.7, 137.4, 137.2, 136.4, 134.8, 134.3, 133.3, 133.2, 128.8, 128.7, 128.64, 128.62, 128.5, 128.47, 128.4, 128.1, 128.0, 127.8, 127.51, 127.46, 127.3, 127.2, 126.32, 126.27, 126.2, 100.0, 97.8, 97.6, 97.0, 95.9, 91.9, 83.7, 78.7, 77.2, 75.6, 75.2, 74.7, 74.6, 73.1, 72.5, 67.6, 67.49, 67.45, 66.8, 63.6, 61.9, 57.8, 53.3, 50.9, 49.8, 42.9, 27.2, 23.2, 18.2, 16.6; HR-ESI-MS (m/z): calcd for C$_{75}$H$_{79}$Cl$_6$N$_7$O$_{17}$Na$^+$ (M+Na$^+$): 1584.3532, found: 1584.3595.

Embodiment 29

Synthesis of N-Benzyl-N-benzyloxycarbonyl-3-aminopropyl 2-acetamido-4-O-benzyl-3-O-(4-O-[benzyl 3-azido-4-O-benzyl-2,3-dideoxy-2-trichloroacetamido-6-D-glucopyranosyl uronate]-2-(2,2,2-trichloroethoxycarbonyl)amino-2-deoxy-α-L-fucopyranosyl)-2-deoxy-α-D-quinovopyranoside (29*)

A reaction equation is as shown in FIG. 23.

Compound 28* (1.15 g, 0.734 mmol) was dissolved in the mixture of dichloromethane (6.6 mL) and water (2.6 mL), and then 2,3-dichloro-5,6-dicyano-1,4-benzoquinone (DDQ) (246 mg, 1.101 mmol) was added. The reaction solution was stirred at room temperature for 5 hours. The organic phase obtained by separation was extracted with the 5% sodium thiosulfate solution, and the crude product obtained by concentration was purified by silica gel column chromatography (petroleum ether:acetone, 7:1-6:1, v/v) to obtain the compound 29* (0.89 g, 0.625 mmol, 85%). $[\alpha]_D^{20}$=−6.5° (c=1.00, CHCl$_3$); IR v$_{max}$ (film) 3317, 2934, 2107, 1704, 1517, 1216, 1039, 826, 751, 697 cm$^{-1}$; $^1$H NMR (400 MHz, CDCl$_3$) δ=7.44-7.12 (m, 26H, 5Ph, 2″-NH), 6.90 (d, J=9.4 Hz, 1H, 2-NH), 5.69 (d, J=8.6 Hz, 1H, 2′-NH), 5.23 (q, J=12.2 Hz, 2H, CH$_2$), 5.18-5.03 (m, 4H, CH$_2$, 1′-H, 1″-H), 4.80-4.65 (m, 3H, CH$_2$, CH$_{a1}$), 4.67-4.50 (m, 4H, CH$_2$, CH$_{a2}$, CH$_{b1}$), 4.46 (d, J=3.5 Hz, 1H, 1-H), 4.41-4.29 (m, 3H, CH$_{b2}$, 3″-H, 2-H), 4.09 (d, J=9.6 Hz, 1H, 5″-H), 4.06 (d, J=6.8 Hz, 1H, 5′-H), 4.01-3.84 (m, 2H, 2′-H, 3-H), 3.83-3.57 (m, 5H, 5-H, 3′-H, linker-2H, 4″-H), 3.47 (s, 1H, 3′-OH), 3.41 (s, 1H, 4′-H), 3.23 (m, 3H, linker-H, 2″-H), 3.12 (t, J=9.3 Hz, 1H, 4-H), 2.00 (s, 3H, CH$_3$CO), 1.73 (s, 2H, linker-CH$_2$), 1.31 (d, J=6.2 Hz, 3H, 6-CH$_3$), 0.70 (d, J=6.4 Hz, 3H, 6′-CH$_3$); $^{13}$C NMR (100 MHz, CDCl$_3$) δ=171.5, 167.1, 162.0, 156.4, 155.8, 137.7, 137.4, 136.9, 136.4, 134.8, 128.71, 128.67, 128.6, 128.53, 128.47, 128.4, 128.2, 128.1, 127.9, 127.8, 127.5, 127.2, 127.1, 99.6, 97.7, 95.7, 91.8, 83.4, 83.0, 78.5, 77.3, 75.4, 75.1, 74.9, 74.7, 74.6, 69.4, 67.9, 67.5, 66.5, 63.6, 62.7, 58.1, 53.4, 52.2, 49.7, 42.8, 27.1, 23.1, 18.2, 16.1; HR-ESI-MS (m/z): calcd for C$_{64}$H$_{71}$Cl$_6$N$_7$O$_{17}$Na$^+$ (M+Na$^+$): 1444.2906, found: 1444.2916.

Embodiment 30

Synthesis of N-benzyl-N-benzyloxycarbonyl-3-aminopropyl 2-acetamido-4-O-benzyl-3-O-(4-O-[benzyl 3-azido-4-O-benzyl-2,3-dideoxy-2-trichloroacetamido-6-D-glucopyranosyl uronate]-3-O-acetyl-2-(2,2,2-trichloroethoxycarbonyl)amino-2-deoxy-α-L-fucopyranosyl)-2-deoxy-α-D-quinovopyranoside (30*)

A reaction equation is as shown in FIG. 23.

Compound 29* (828 mg, 0.582 mmol) was dissolved in the anhydrous dichloromethane/pyridine mixture (30 mL, 4:1, v/v). After cooling to 0° C., acetic anhydride (550 μL, 5.821 mmol) was added dropwise. After dimethylaminopyridine (1.4 mg, 0.012 mmol) was added, the reaction solution was stirred at room temperature. After the reaction was completed, the reaction solution was extracted with the saturated sodium bicarbonate solution, and the organic phase was dried with anhydrous sodium sulfate and distilled off the solvent under reduced pressure. The crude product was purified by silica gel column chromatography (petroleum ether:acetone, 6:1, v/v) to obtain the white solid-like compound 30* (798 mg, 0.544 mmol, 94%). $[\alpha]_D^{20}$=−37.00 (c=1.00, CHCl$_3$); IR v$_{max}$ (film) 3337, 2964, 2108, 1744, 1521, 1456, 1367, 1260, 1074, 1021, 800, 752, 697 cm$^{-1}$; $^1$H NMR (400 MHz, CDCl$_3$) δ=7.42-7.11 (m, 26H, 5Ph, 2″-NH), 6.78 (d, J=9.5 Hz, 1H, 2-NH), 5.43 (d, J=9.9 Hz, 1H, 2′-NH), 5.23-5.07 (m, 5H, 1′-H, PhCH$_2$-4H), 5.01 (d, J=12.0 Hz, 1H, CH$_2$-1H), 4.94 (dd, J=11.8, 2.7 Hz, 1H, 3′-H), 4.89 (d, J=8.1 Hz, 1H, 1″-H), 4.78 (d, J=10.8 Hz, 1H, PhCH$_2$), 4.68 (d, J=10.7 Hz, 1H, CH$_2$-1H), 4.64-4.48 (m, 4H, CH$_2$-4H), 4.47-4.42 (m, 2H, 1-H, 3″-H), 4.37 (m, 2H, 2-H, NCH$_2$Ph), 4.21 (ddd, J=11.4, 9.8, 3.5 Hz, 1H, 2′-H), 4.04 (t, J=6.5 Hz, 1H, 5′-H), 3.92 (m, 2H, 3-H, 5″-H), 3.83-3.54 (m, 5H, 5-H, 4″-H, 4′-H, linker-2H), 3.34-3.08 (m, 4H, 4-H, 2″-H, linker-2H), 1.97 (s, 3H, CH$_3$CO), 1.96 (s, 3H, CH$_3$CO), 1.73 (m, 2H, linker-2H), 1.33 (d, J=6.2 Hz, 3H, 6-CH$_3$), 0.61 (d, J=6.7 Hz, 3H, 6′-CH$_3$); $^{13}$C NMR (100 MHz, CDCl$_3$) δ=170.9, 167.6, 162.0, 156.4, 154.8, 137.7, 137.4, 137.0, 136.4, 134.7, 128.8, 128.7, 128.53, 128.46, 128.4, 128.0, 127.9, 127.8, 127.5, 127.3, 98.7, 97.6, 97.4, 95.8, 91.9, 83.4, 79.0, 77.2, 75.6, 75.0, 74.9, 74.5, 67.8, 67.76, 67.5, 65.7, 62.3, 58.4, 53.4, 49.8, 49.2, 42.9, 27.1, 23.1, 20.9, 18.2, 15.8; HR-ESI-MS (m/z): calcd for C$_{66}$H$_{74}$Cl$_6$N$_7$O$_{18}$$^+$ (M+H$^+$): 1464.3192, found: 1464.3281.

Embodiment 31

Synthesis of N-benzyl-N-benzyloxycarbonyl-3-aminopropyl 2-acetamido-4-O-benzyl-3-O-(4-O-[benzyl 3-amino-4-O-benzyl-2-dichloroacetamido-2,3-dideoxy-6-D-glucopyranosyl uronate]-3-O-acetyl-2-(2,2,2-trichloroethoxycarbonyl)amino-2-deoxy-α-L-fucopyranosyl)-2-deoxy-α-D-quinovopyranoside (31*)

A reaction equation is as shown in FIG. 23.

Compound 30* (745 mg, 0.509 mmol) was dissolved in pyridine (51 mL), and then water (4.76 mL, 265 mmol), triethylamine (1.06 mL, 7.632 mmol) and 1,3-propanedithiol (1 mL, 10.176 mmol) were added. The reaction solution was stirred at room temperature for 6 hours. The crude product obtained by concentration of the reaction solution mixture was purified by silica gel column chromatography (petroleum ether:acetone, 5:1-3:1, v/v) to obtain the colorless syrup-like compound 31* (460 mg, 0.327 mmol, 64%). $[\alpha]_D^{20}$=−63.1° (c=1.00, CHCl$_3$); IR v$_{max}$ (film) 3322, 2940, 1746, 1682, 1526, 1454, 1363, 1242, 1074, 738, 699 cm$^{-1}$; $^1$H NMR (400 MHz, CDCl$_3$) δ=7.51-7.09 (m, 25H, 5Ph), 6.81 (d, J=9.3 Hz, 1H, 2-NH), 5.90 (s, 1H, CHCl$_2$), 5.47 (s, 1H, 2′-NH), 5.30-5.05 (m, 5H, 2CH$_2$, 1′-H), 4.98 (m, 2H, 3′-H, CH$_2$-1H), 4.77 (d, J=10.9 Hz, 1H, CH$_2$-1H), 4.71 (s, 1H, 1″-H), 4.67-4.49 (m, 5H, NCH$_a$Ph, CH$_2$, 2CH$_2$-1H), 4.45 (d, J=4.0 Hz, 1H, 1-H), 4.41-4.30 (m, 2H, NCH$_b$Ph, 2-H), 4.29-4.16 (m, 1H, 2′-H), 4.14-3.98 (m, 1H, 5′-H), 3.91 (m, 2H, 5″-H, 3-H), 3.78 (q, J=7.5, 7.0 Hz, 1H, 5-H), 3.83-3.56 (m, 4H, 4′-H, 4″-H, linker-2H), 3.47 (s, 1H, 2″-H), 3.36-3.06 (m, 3H, linker-2H, 4-H), 1.96 (s, 6H, 2CH$_3$CO), 1.73 (m, 2H, linker-CH$_2$), 1.33 (d, J=6.1 Hz, 3H, 6-CH$_3$), 0.63 (d, J=6.5 Hz, 3H, 6′-CH$_3$); $^{13}$C NMR (100 MHz, CDCl$_3$) δ=171.1, 168.3, 156.4, 137.9, 137.5, 137.4, 136.5, 134.8, 128.74, 128.68, 128.5, 128.4, 128.1, 127.9, 127.8, 127.5, 127.3, 100.2, 97.6, 95.8, 83.3, 77.2, 75.6, 74.5, 74.4, 69.9, 67.8, 67.6, 67.5, 66.5, 66.0, 63.7, 54.2, 53.4, 49.8, 49.1, 27.2, 23.1, 20.9, 18.2, 15.9; HR-ESI-MS (m/z): calcd for C$_{66}$H$_{77}$Cl$_5$N$_5$O$_{18}$$^+$ (M+H$^+$): 1404.3677, found: 1404.3643.

Embodiment 32

Synthesis of N-benzyl-N-benzyloxycarbonyl-3-aminopropyl 2-acetamido-4-O-benzyl-3-O-(4-O-[benzyl 4-O-benzyl-3-N—(R)-3-O-benzylbutyryl-2-dichloroacetamido-2,3-dideoxy-6-D-glucopyranosyl uronate]-3-O-acetyl-2-(2,2,2-trichloroethoxycarbonyl)amino-2-deoxy-α-L-fucopyranosyl)-2-deoxy-α-D-quinovopyranoside (32*)

A reaction equation is as shown in FIG. 23.

(R)-3-O-benzylbutyric acid (D. Seebach et al. Helv. Chim. Acta 1988, 71, 155-167) (234 mg, 1.205 mmol) was dissolved in 23 mL of anhydrous dichloromethane, and then oxalyl chloride (0.8 mL, 9.156 mmol) was added at 0° C. After the mixture was stirred at room temperature for 4 hours, the solvent and residual reagents were distilled off under reduced pressure, and obtained (R)-3-O-benzylbutyryl chloride was vacuumized for 3 hours. The amino compound 31* (113 mg, 0.081 mmol) was dissolved in 4 mL of anhydrous dichloromethane, and after triethylamine (167 μL, 1.207 mmol) and the anhydrous dichloromethane solution (4 mL) of (R)-3-O-benzylbutyryl chloride were added, the reaction solution was stirred at room temperature overnight. After the reaction was completed, the reaction was quenched by the addition of 0.3 mL of methanol at 0° C. The crude product obtained by concentration was purified by silica gel column chromatography (petroleum ether:acetone, 5:1, v/v) to obtain the colorless syrup-like compound 32* (92 mg, 0.058 mmol, 72%). $[α]_D^{20}$=−47.1° (c=1.00, CHCl$_3$); IR v$_{max}$ (film) 3281, 2935, 1744, 1661, 1532, 1454, 1246, 1045, 737, 698 cm$^{-1}$; $^1$H NMR (400 MHz, CDCl$_3$) δ=7.54 (d, J=5.1 Hz, 1H, 2-NH), 7.46-6.88 (m, 30H, 6Ph), 6.76 (d, J=9.6 Hz, 1H, 2"-NH), 6.64 (d, J=9.1 Hz, 1H, 3"-NH), 5.78 (s, 1H, DCA-1H), 5.40 (d, J=9.9 Hz, 1H, 2'-NH), 5.29-4.94 (m, 6H, 2CH$_2$, CH$_2$-1H, 1'-H), 4.88 (d, J=11.1 Hz, 1H, 3'-H), 4.70 (s, 2H, CH$_2$), 4.65-4.50 (m, 3H, CH$_2$-3H), 4.50-4.45 (m, 1H, 1"-H), 4.44-4.27 (m, 5H, 1-H, 2"-H, 3"-H, CH$_2$), 4.23 (m, 2H, 2'-H, CH$_2$-1H), 4.02-3.85 (m, 4H, 5"-H, 5'-H, 3-H, 2-H), 3.79 (m, 2H, butyryl-CH, 5-H), 3.66 (m, 2H, linker-2H), 3.53 (t, J=8.6 Hz, 1H, 4"-H), 3.40 (s, 1H, 4'-H), 3.26 (s, 2H, linker-2H), 3.14 (t, J=9.2 Hz, 1H, 4-H), 2.40-2.12 (m, 2H, butyryl-CH$_2$), 1.96 (s, 6H, 2CH$_3$CO), 1.72 (s, 2H, linker-2H), 1.28 (d, J=6.3 Hz, 3H, 6-CH$_3$), 1.19 (d, J=6.2 Hz, 3H, butyryl-CH$_3$), 0.65 (d, J=6.4 Hz, 3H, 6'-CH$_3$); 13C NMR (100 MHz, CDCl$_3$) δ=171.9, 171.2, 171.0, 168.0, 164.4, 156.4, 154.5, 137.9, 137.44, 137.35, 136.5, 134.9, 128.8, 128.71, 128.65, 128.6, 128.5, 128.42, 128.38, 128.1, 128.0, 127.9, 127.8, 127.7, 127.6, 127.4, 127.3, 102.0, 97.6, 95.9, 83.3, 77.3, 75.6, 75.3, 74.5, 74.0, 71.5, 70.4, 69.8, 67.7, 67.5, 66.3, 66.0, 63.7, 54.6, 53.4, 52.5, 49.8, 49.1, 43.6, 43.0, 27.2, 23.2, 20.9, 19.4, 18.2, 15.9; HR-ESI-MS (m/z): calcd for C$_{77}$H$_{88}$Cl$_5$N$_5$O$_{20}$Na$^+$ (M+Na$^+$): 1602.4333, found: 1602.4312.

Embodiment 33

Synthesis of N-benzyl-N-benzyloxycarbonyl-3-aminopropyl 2-acetamido-4-O-benzyl-3-O-(4-O-[benzyl 2-acetamido-4-O-benzyl-3-N—(R)-3-O-benzylbutyryl-2,3-dideoxy-6-D-glucopyranosyl uronate]-2-amino-3-O-acetyl-2-deoxy-α-L-fucopyranosyl)-2-deoxy-α-D-quinovopyranoside (33*)

A reaction equation is as shown in FIG. 23.

Excessive zinc powder was added to an acetic acid (10 mL) solution of trisaccharide 32* (48.3 mg, 0.031 mmol), and the reaction solution was heated to 55° C. and stirred for 4 hours. After the reaction solution was filtered by celite, the crude product obtained by concentration was purified by silica gel column chromatography (dichloromethane:methanol, 20:1, v/v) to obtain the compound 33* (33.4 mg, 0.025 mmol, 81%). $[α]_D^{20}$=−73.4° (c=0.50, CHCl$_3$); IR v$_{max}$ (film) 3289, 2924, 1748, 1656, 1546, 1367, 1238, 1073, 739, 698 cm$^{-1}$; $^1$H NMR (400 MHz, CDCl$_3$) δ=7.45-6.99 (m, 30H, 6Ph), 5.13 (m, 5H, 2PhCH$_2$, 1'-H), 4.93 (m, 1H, 3'-H), 4.72 (s, 2H, PhCH$_2$), 4.68-4.44 (m, 4H, NCH$_a$Ph, PhCH$_2$-1H, 1-H, 3"-H), 4.42-4.28 (m, 4H, PhCH$_2$, PhCH$_2$-1H, NCH$_b$Ph), 4.27-4.07 (m, 2H, 2-H, 1"-H), 4.01 (d, J=6.6 Hz, 1H, 5'-H), 3.90 (m, 4H, butyryl-CH, 2"-H, 3-H, 5"-H), 3.71 (m, 5H, 5-H, 4'-H, linker-2H, 4"-H), 3.50-3.03 (m, 4H, 2'-H, linker-2H, 4-H), 2.34 (d, J=31.3 Hz, 2H, butyryl-CH$_2$), 2.16-1.86 (m, 6H, 2CH$_3$CO), 1.82 (s, 3H, CH$_3$CO), 1.77-1.62 (m, 2H, linker-CH$_2$), 1.30 (d, J=6.2 Hz, 3H, 6-CH$_3$), 1.19 (d, J=6.1 Hz, 3H, butyryl-CH$_3$), 0.80-0.48 (d, J=5.6 Hz, 3H, 6'-CH$_3$); $^{13}$C NMR (100 MHz, CDCl$_3$) δ=172.3, 171.0, 168.2, 156.4, 138.3, 138.0, 137.5, 136.5, 134.8, 128.7, 128.6, 128.5, 128.4, 128.3, 128.2, 128.1, 127.8, 127.7, 127.5, 127.2, 97.4, 77.2, 75.7, 75.3, 74.1, 71.8, 70.4, 67.5, 67.4, 66.0, 54.2, 53.2, 49.8, 48.7, 43.5, 43.1, 29.7, 27.2, 23.3, 21.3, 19.2, 18.1, 15.9; HR-ESI-MS (m/z): calcd for C$_{74}$H$_{90}$N$_5$O$_{18}$$^+$ (M+H$^+$): 1336.6281, found: 1336.6243.

Embodiment 34

Synthesis of N-benzyl-N-benzyloxycarbonyl-3-aminopropyl 2-acetamido-4-O-benzyl-3-O-(4-O-[benzyl 2-acetamido-4-O-benzyl-3-N—(R)-3-O-benzylbutyryl-2,3-dideoxy-6-D-glucopyranosyl uronate]-2-acetamidino-3-O-acetyl-2-deoxy-α-L-fucopyranosyl)-2-deoxy-α-D-quinovopyranoside (34*)

A reaction equation is as shown in FIG. 23.

Under protection of argon, the amino compound 33* (12.5 mg, 9.35 μmol) was dissolved in 2 mL of anhydrous pyridine. After cooling to 0° C., benzyl thioacetimidate hydrochloride (3.8 mg, 18.7 μmol) was added. The reaction solution was stirred at 0° C. for 5 hours, and the crude product obtained by concentration was purified by silica gel column chromatography (dichloromethane:methanol, 20:1, v/v) to obtain the colorless syrup-like compound 34* (9.0 mg, 6.53 μmol, 70%). $[α]_D^{20}$=−72.7° (c=0.50, CHCl$_3$); IR v$_{max}$ (film) 3292, 1749, 1657, 1564, 1373, 1232, 1074, 1047, 739, 698 cm$^{-1}$; $^1$H NMR (400 MHz, CDCl$_3$) δ=7.49 (d, J=8.7 Hz, 2H, 2-NH, 3"-NH), 7.44-7.15 (m, 30H, 6Ph), 6.96 (s, 1H, 2'-NH), 5.28-5.07 (m, 4H, 2PhCH$_2$), 4.99 (m, 2H, 1'-H, 3'-H), 4.83 (d, J=10.8 Hz, 1H, PhCH$_2$-1H), 4.67 (d, J=15.7 Hz, 1H, PhCH$_2$-1H), 4.61-4.37 (m, 6H, 2PhCH$_2$, PhCH$_2$-1H, 1-H), 4.35-4.11 (m, 5H, PhCH$_2$-1H, 1"-H, 2'-H, 2-H, 3"-H), 4.06 (d, J=6.6 Hz, 1H, 5'-H), 3.92 (m, 6H, linker-1H, butyryl-CH, 3-H, 2"-H, 4"-H, 5"-H), 3.86-3.77 (m, 1H, 5-H), 3.67 (m, 2H, linker-1H, 4'-H), 3.17 (m, 2H, linker-1H, 4-H), 3.06 (d, J=14.2 Hz, 1H, linker-1H), 2.59 (s, 3H, Am—CH$_3$), 2.39 (m, 2H, butyryl-CH$_2$), 2.09 (s, 3H, CH$_3$CO), 2.02 (s, 3H, CH$_3$CO), 1.81 (s, 3H, CH$_3$CO), 1.73 (m, 2H, linker-CH$_2$), 1.36 (d, J=6.4 Hz, 3H, 6-CH$_3$), 1.17 (d, J=5.8 Hz, 3H, butyryl-CH$_3$), 0.50 (d, J=6.3 Hz, 3H, 6'-CH$_3$); $^{13}$C NMR (100 MHz, CDCl$_3$) δ=172.9, 170.6, 168.2, 166.8, 156.6, 138.5, 137.7, 137.4, 136.3, 134.8, 128.8, 128.7, 128.65, 128.6, 128.5, 128.4, 128.3, 128.2, 128.0, 127.9, 127.71, 127.65, 127.6, 127.5, 127.3, 102.3, 97.6, 96.4, 83.2, 77.2, 76.0, 75.8, 75.1, 74.3, 71.9, 70.8, 70.4, 68.0, 67.7, 67.5, 66.2, 63.3, 54.0, 53.0, 50.1, 49.7, 43.5, 42.6, 27.0, 23.3, 21.2, 19.8, 19.5, 18.2, 15.4; HR-ESI-MS (m/z): calcd for C$_{76}$H$_{93}$N$_6$O$_{18}$$^+$ (M+H$^+$): 1377.6546, found: 1377.6526.

Embodiment 35

Synthesis of 3-aminopropyl 2-acetamido-3-O-(4-O-[2-acetamido-2,3-dideoxy-3-N—(R)-3-hydroxybutyryl-6-D-glucopyranosyl uronate]-2-acetamidino-3-O-acetyl-2-deoxy-α-L-fucopyranosyl)-2-deoxy-α-D-quinovopyranoside (35*)

A reaction equation is as shown in FIG. 23.

Trisaccharide 34* (4.3 mg, 3.1 μmol) was dissolved in the t-butanol/water/dichloromethane mixture (3 mL, 5:2:1, v/v/v). After the reaction system was replaced with nitrogen, the 10% palladium on carbon hydrogenation catalyst was added, and nitrogen replacement was continued for 5 minutes. After further replacing the reaction system with hydrogen for 5 minutes, the reaction solution was stirred in the hydrogen atmosphere for 24 hours, the crude product obtained by celite filtration and concentration was preliminarily purified by the C18 column (Macherey-Nagel, Düren, Germany) (eluent were water and methanol), and the product was further purified by reversed phase high performance liquid chromatography (semipreparative Thermo Scientific Hypercarb column) to obtain the white solid-like target product 35* (1.9 mg, 2.4 ⌧ μmol, 77%). $[α]_D^{20}=-66.26°$ (c=0.10, $H_2O$); $^1H$ NMR (700 MHz, $D_2O$) δ=5.18 (d, J=3.9 Hz, 1H, 1'-H), 5.10 (dd, J=11.3, 2.7 Hz, 1H, 3'-H), 4.74 (d, J=3.6 Hz, 1H, 1-H), 4.61 (d, J=8.3 Hz, 1H, 1"-H), 4.53 (q, J=6.7 Hz, 1H, 5'-H), 4.26 (dd, J=11.1, 3.9 Hz, 1H, 2'-H), 4.21-4.12 (m, 3H, butyryl-CH, 4'-H, 2-H), 4.05-3.99 (m, 1H, 3"-H), 3.92-3.84 (m, 1H, 2"-H), 3.83-3.75 (m, 3H, 5-H, 3-H, linker-CHa), 3.73 (d, J=9.7 Hz, 1H, 5"-H), 3.71-3.62 (m, 1H, 4"-H), 3.55 (ddd, J=21.7, 11.5, 6.1 Hz, 1H, linker-$CH_b$), 3.34 (t, J=9.3 Hz, 1H, 4-H), 3.13-3.03 (m, 2H, linker-$CH_2$), 2.49 (dd, J=14.1, 7.4 Hz, 1H, butyryl-$CH_2$), 2.42-2.36 (m, 1H, butyryl-$CH_2$), 2.26 (s, 3H, Am—$CH_3$), 2.10 (s, 3H, $CH_3CO$), 2.01 (s, 3H, $CH_3CO$), 2.00-1.91 (m, 5H, linker-$CH_2$, $CH_3CO$), 1.31 (d, J=6.2 Hz, 3H, 6-$CH_3$), 1.20 (d, J=6.4 Hz, 6H, 6'-$CH_3$, butyryl-$CH_3$); $^{13}C$ NMR (176 MHz, $D_2O$) δ=175.1, 174.8, 174.4, 173.6, 173.1, 166.1, 102.7, 96.9, 95.8, 78.9, 77.4, 75.9, 73.5, 70.4, 70.2, 67.8, 66.7, 65.0, 64.9, 54.3, 53.9, 53.4, 50.3, 45.1, 37.2, 27.1, 22.2, 21.8, 21.6, 20.3, 18.8, 16.7, 15.0; HR-ESI-MS (m/z): calcd for $C_{33}H_{57}N_6O_{16}^+(M+H^+)$: 793.3831, found: 793.3812.

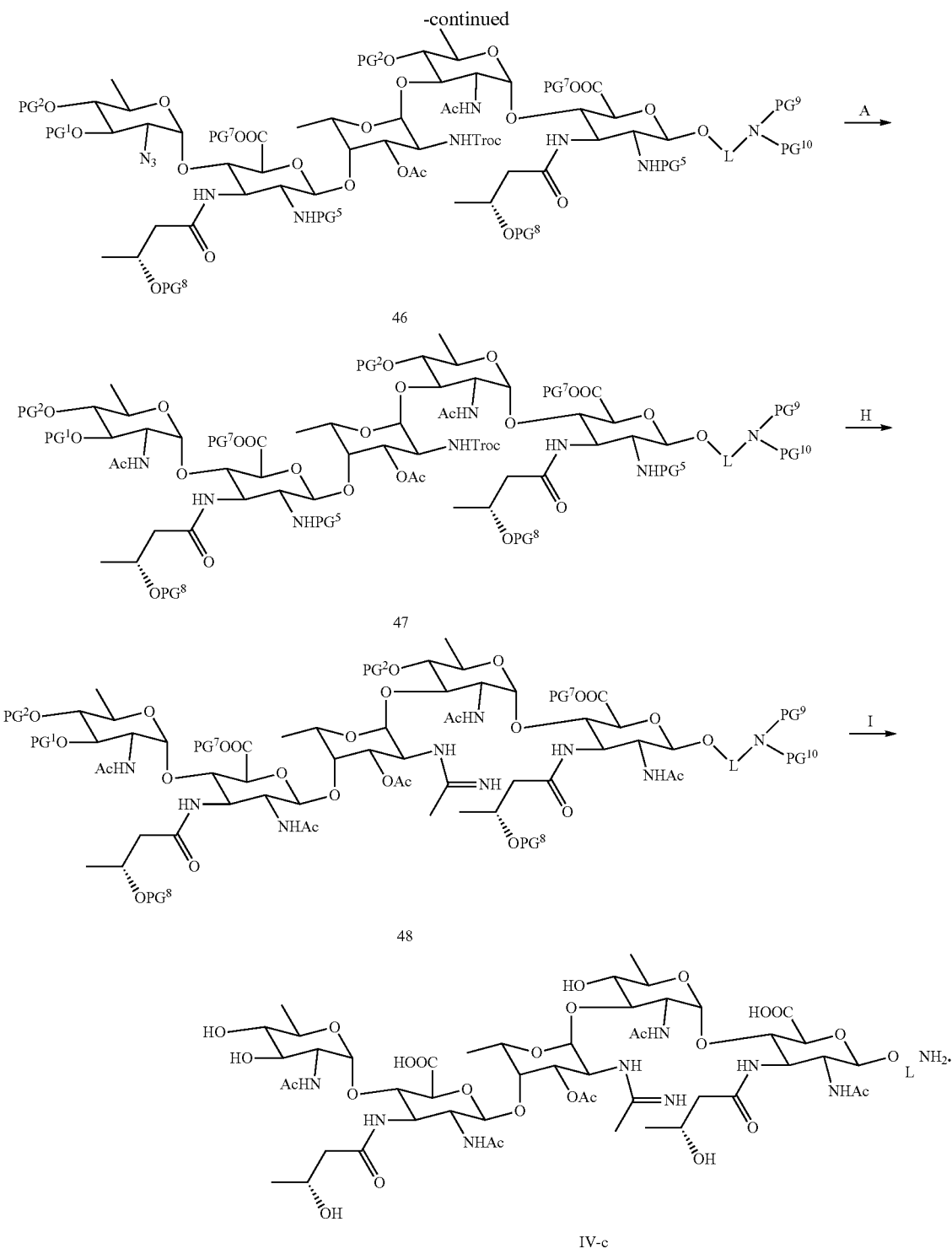

What is claimed is:

1. A linked oligosaccharide chain fragment of the *Plesiomonas shigelloides* serotype O51 O-antigen polysaccharide, wherein the structure of the oligosaccharide chain fragment is expressed as the general Formula I:

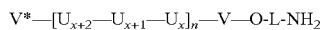

V*—$[U_{x+2}—U_{x+1}—U_x]_n$—V—O-L-$NH_2$  Formula I, wherein:

X is 1, 2, or 3;

n is 1, 2, or 3;

—V— represents: the chemical bond, —$U_{x+2}$—, or —$U_{x+2}$—$U_{x+1}$—;

V*— represents: H—, H—$U_x$—, or H—$U_{x+1}$—$U_x$—;

L represents the linker; and $U_x$, $U_{x+1}$ and $U_{x+2}$ are as shown in Formula V:

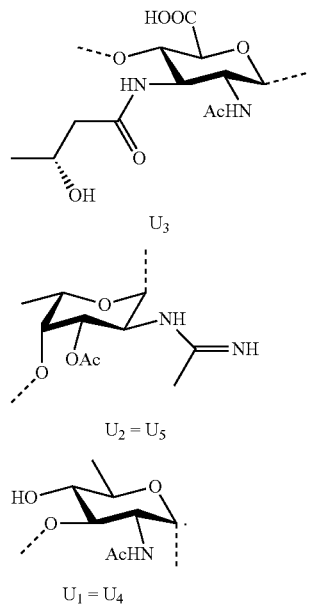

Formula V

2. The linked oligosaccharide chain fragment of the *Plesiomonas shigelloides* serotype O51 O-antigen polysaccharide according to claim 1, wherein the structure of the oligosaccharide chain fragment is expressed as the general Formula II:

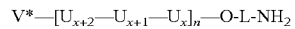

V*—$[U_{x+2}—U_{x+1}—U_x]_n$—O-L-$NH_2$  Formula II, wherein:

x, n, L, $U_x$, $U_{x+1}$, $U_{x+2}$ and V* are in accordance with the general Formula I; and the general Formula II is further expressed as the general Formulae II-a, II-b, or II-c:

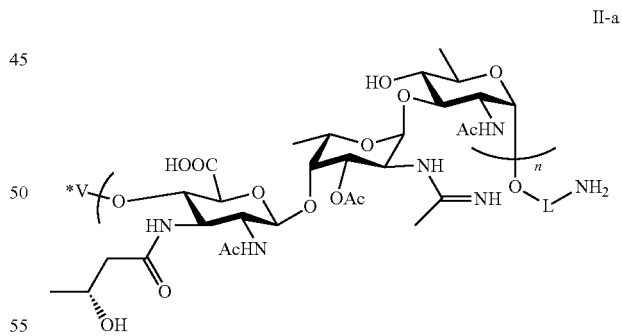

II-a

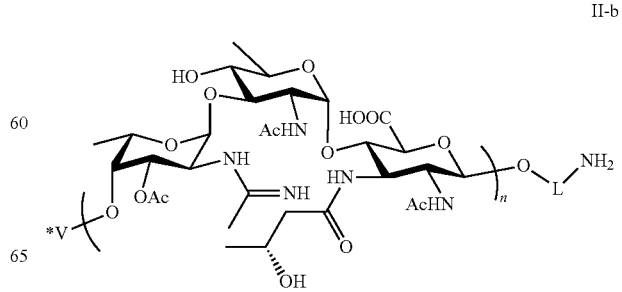

II-b

-continued

II-c

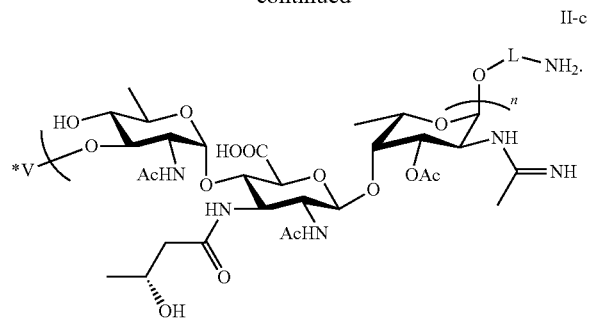

3. The linked oligosaccharide chain fragment of the *Plesiomonas shigelloides* serotype O51 O-antigen polysaccharide according to claim 1, wherein the structure of the oligosaccharide chain fragment is expressed as the general Formula III:

$$V^*-[U_{x+2}-U_{x+1}-U_x]_n-U_{x+2}-O-L-NH_2 \quad \text{Formula III,}$$

wherein:

x, n, L, $U_x$, $U_{x+1}$, $U_{x+2}$ and V* are in accordance with the general Formula I, and the general Formula III is further expressed as the general Formulae III-a, III-b, or III-c:

III-a

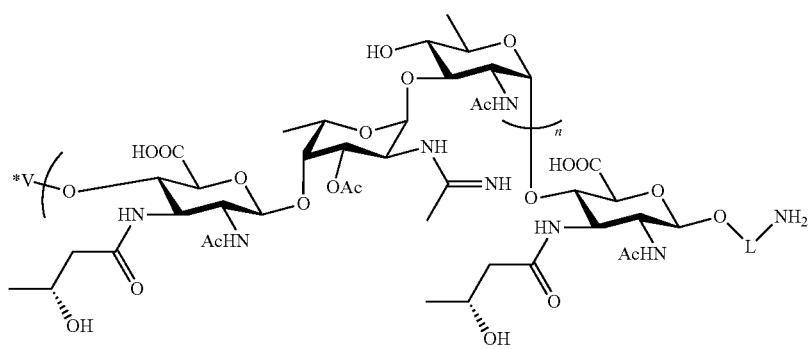

III-b

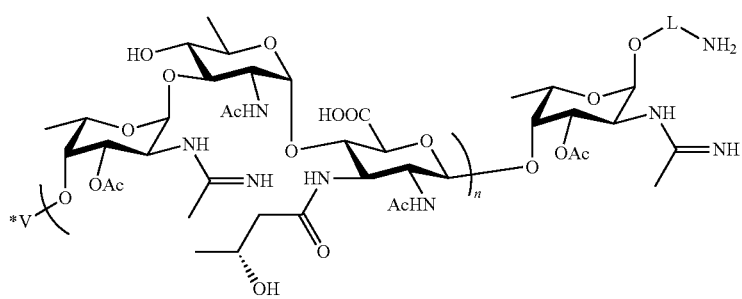

III-c

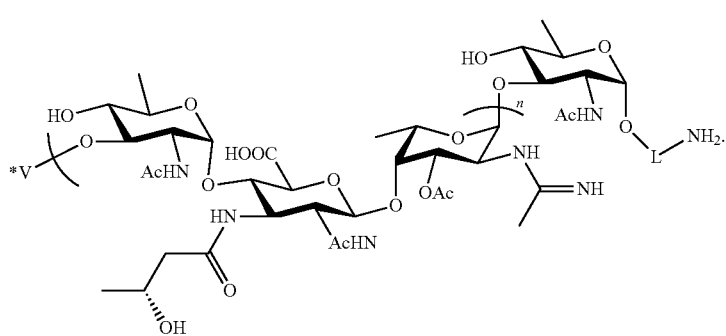

4. The linked oligosaccharide chain fragment of the *Plesiomonas shigelloides* serotype O51 O-antigen polysaccharide according to claim 1, wherein the structure of the oligosaccharide chain fragment is expressed as the general Formula IV:

V*—[$U_{x+2}$—$U_{x+1}$—$U_x$]$n$-$U_{x+2}$—$U_{x+1}$—O-L-NH$_2$   Formula IV, wherein:
x, n, L, $U_x$, $U_{x+1}$, $U_{x+2}$ and V* are in accordance with the general Formula I, and
the general Formula IV is further specifically expressed as general Formulae IV-a, IV-b, and IV-c:

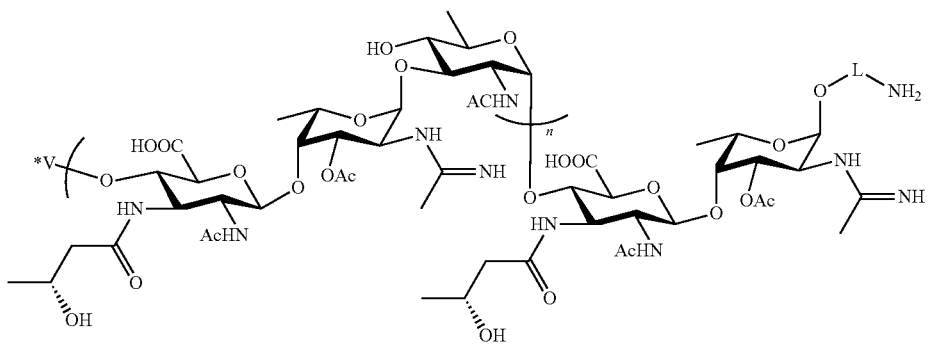

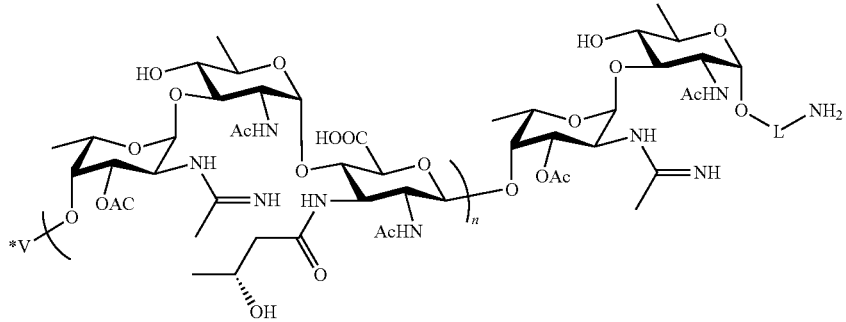

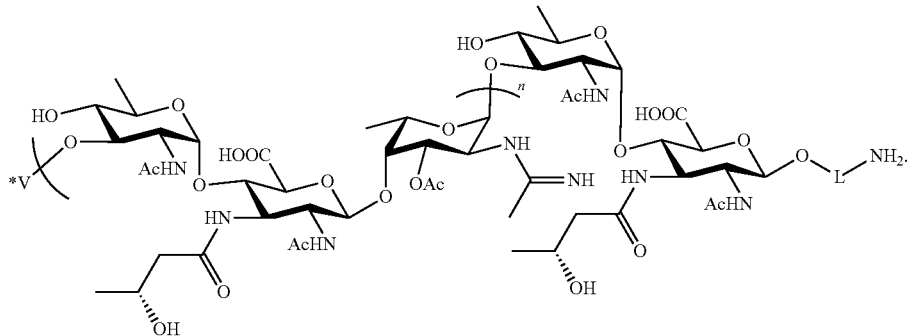

5. A method of preparing the linked oligosaccharide chain fragment of the *Plesiomonas shigelloides* serotype O51 O-antigen polysaccharide of Formula II-a according to claim 2, which comprises:
providing a monosaccharide building block 1 as a starting material for synthesis of D-quinovosamine in an oligosaccharide chain,
wherein:
the monosaccharide building block 1 is expressed as Formula VI-1:

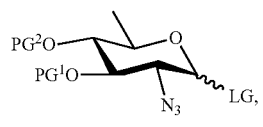

$PG^1$ is acetyl, levulinyl, benzoyl, chloroacetyl, dichloroacetyl, trichloroacetyl, pivaloyl, allyloxycarbonyl, 2-naphthylmethyl, p-methoxybenzyl, tert-butyldimethylsilyl, tert-butyldiphenylsilyl, or triethylsilyl;

$PG^2$ is benzyl; and

LG is ethylthio, p-tolylthio, phenylthio, bromine, fluorine, trichloroacetimidate, N-phenyl trifluoroacetimidate or dibutyl phosphate, and performing chemical synthesis steps A through I in order:

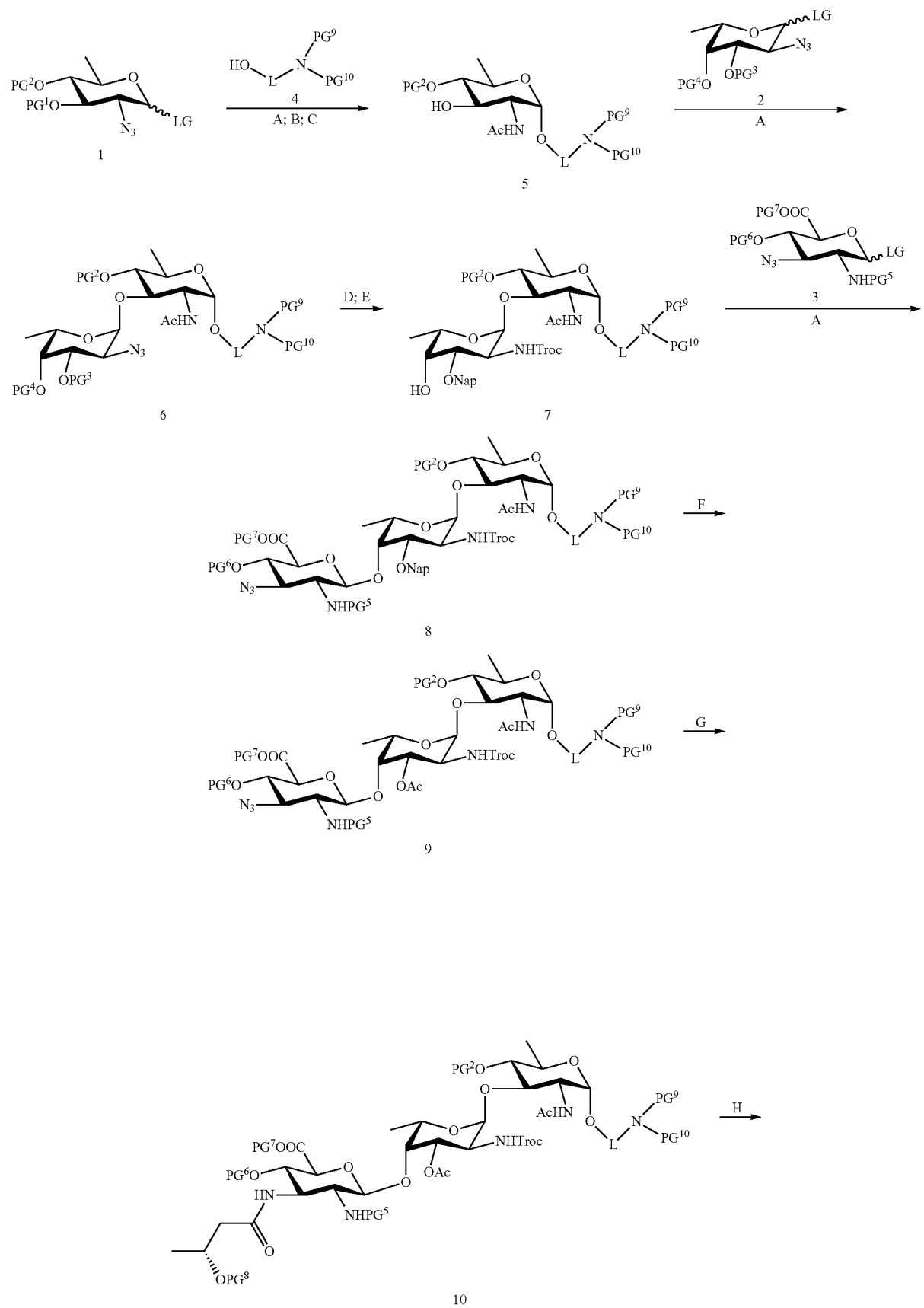

-continued

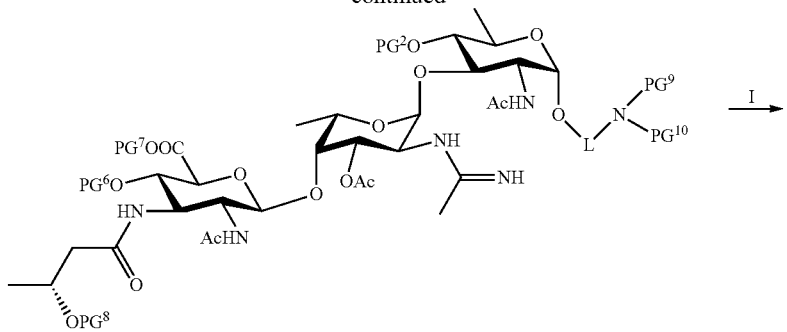

11

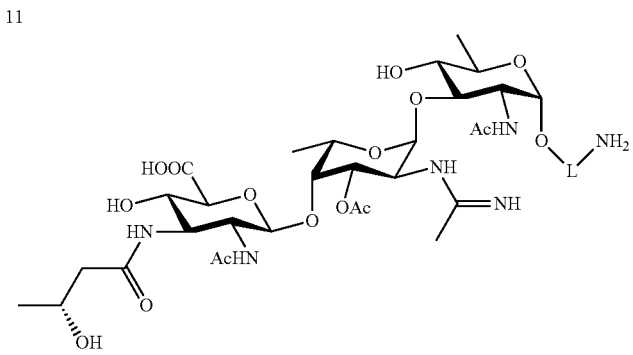

II-a wherein steps A through I are:
A: glycosylation of the monosaccharide building block 1;
B: reduction and acetylation of the azide group of the monosaccharide building block 1;
C: 3-position deprotection of the monosaccharide building block 1, followed by glycosylation of monosaccharide building block 1 with monosaccharide building block 2 to obtain a disaccharide 6, wherein:
the monosaccharide building block 2 is expressed as Formula VI-2:

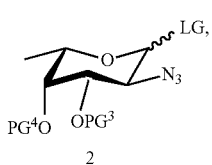

$PG^3$ and $PG^4$ are acetyl, levulinyl, benzoyl, chloroacetyl, dichloroacetyl, trichloroacetyl, pivaloyl, allyloxycarbonyl, 2-naphthylmethyl, p-methoxybenzyl, tert-butyldimethylsilyl, tert-butyldiphenylsilyl, or triethylsilyl;
$PG^9$ and $PG^{10}$ are amino protecting groups, and can be benzyl (Bn) or benzyloxycarbonyl (Cbz), and
LG is ethylthio, p-tolylthio, phenylthio, bromine, fluorine, trichloroacetimidate, N-phenyl trifluoroacetimidate or dibutyl phosphate,
D: azido reduction and protection of disaccharide 6 by 2,2,2-trichloroethoxycarbonyl (Troc), followed by glycosylation of the disaccharide 6 with monosaccharide building block 3 to obtain a trisaccharide,
wherein:
the monosaccharide building block 3 is expressed as Formula VI-3:

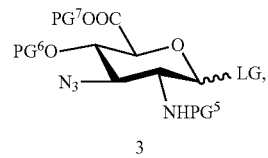

$PG^5$ is trichloroacetyl, dichloroacetyl or chloroacetyl;
$PG^6$ is benzyl, 2-naphthylmethyl, p-methoxybenzyl or levulinyl;
$PG^7$ is benzyl; and wherein LG is ethylthio, p-tolylthio, phenylthio, bromine, fluorine, trichloroacetimidate, N-phenyl trifluoroacetimidate or dibutyl phosphate, and
LG is ethylthio, p-tolylthio, phenylthio, bromine, fluorine, trichloroacetimidate, N-phenyl trifluoroacetimidate or dibutyl phosphate;
E: fucosamine 3-/4-position-selective naphthylmethyl protection to obtain trisaccharide 8;
F: fucosamine 3-position acetylation of the trisaccharide 8;
G: azido reduction and butyrylation to provide trisaccharide 10;
H: removal of Troc and modification to acetamidine;
I: hydrogenation global deprotection;
J: glucuronic acid 4-position deprotection; and
K: azido reduction and modification to acetamidine.

6. A method of preparing the linked oligosaccharide of Formula II-c according to claim 2, which comprises:
providing a monosaccharide building block 2 is used as starting material for synthesis of L-fucosamine in an oligosaccharide chain, wherein:
the monosaccharide building block 2 is expressed as Formula VI-2:

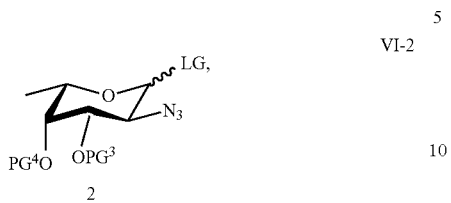

VI-2

PG³ and PG⁴ are acetyl, levulinyl, benzoyl, chloroacetyl, dichloroacetyl, trichloroacetyl, pivaloyl, allyloxycarbonyl, 2-naphthylmethyl, p-methoxybenzyl, tert-butyldimethylsilyl, tert-butyldiphenylsilyl, or triethylsilyl;

LG is ethylthio, p-tolylthio, phenylthio, bromine, fluorine, trichloroacetimidate, N-phenyl trifluoroacetimidate or dibutyl phosphate, and performing chemical synthesis steps A, B, D, E, F, G, H, I, and J, in the following order:

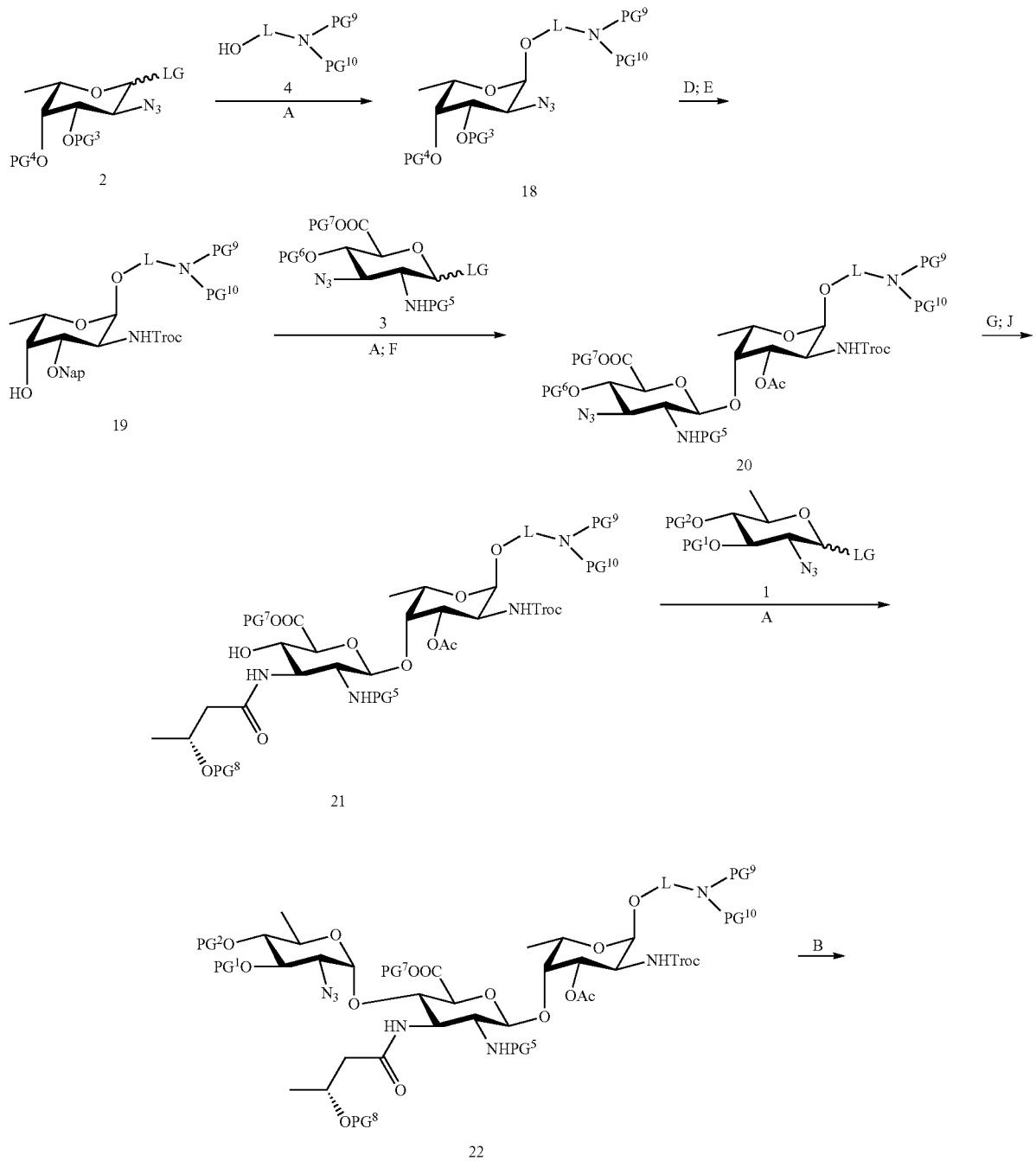

-continued

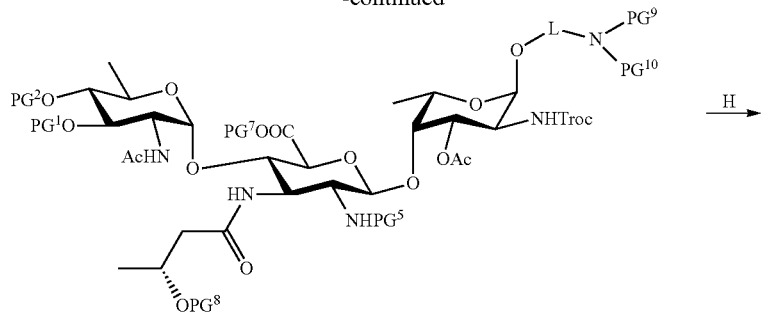

23

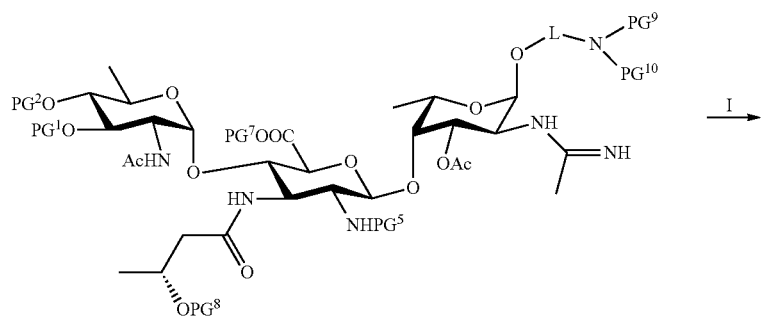

24

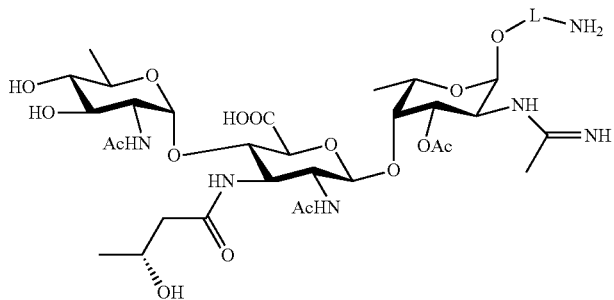

II-c wherein steps A, B, D, E, F, G, H, I, and J, are the following:
A: glycosylation of the monosaccharide building block 2;
D: azido reduction and protection by 2,2,2-trichloroethoxycarbonyl (Troc), E: fucosamine 3-/4-position-selective naphthylmethyl protection to obtain monosaccharide acceptor 19, followed by glycosylation of the monosaccharide acceptor 19 with monosaccharide building block 3 to obtain disaccharide 20,
wherein:
the monosaccharide building block 3 is expressed as Formula VI-3:

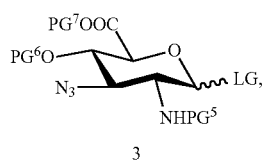

3

$PG^5$ is trichloroacetyl, dichloroacetyl or chloroacetyl;

$PG^6$ is benzyl, 2-naphthylmethyl, p-methoxybenzyl or levulinyl;

$PG^7$ is benzyl; and wherein LG is ethylthio, p-tolylthio, phenylthio, bromine, fluorine, trichloroacetimidate, N-phenyl trifluoroacetimidate or dibutyl phosphate, and LG is ethylthio, p-tolylthio, phenylthio, bromine, fluorine, trichloroacetimidate, N-phenyl trifluoroacetimidate or dibutyl phosphate;

F: fucosamine 3-position acetylation of trisaccharide 8;

G: azido reduction and butyrylation;

J: glucuronic acid 4-position deprotection to obtain disaccharide acceptor 21, followed by glycosylation of the disaccharide acceptor 21 with monosaccharide building block 1 to obtain trisaccharide 22, wherein:
the monosaccharide building block 1 is expressed as Formula VI-1:

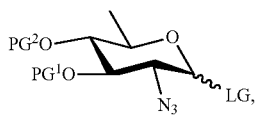

1

- $PG^1$ is acetyl, levulinyl, benzoyl, chloroacetyl, dichloroacetyl, trichloroacetyl, pivaloyl, allyloxycarbonyl, 2-naphthylmethyl, p-methoxybenzyl, tert-butyldimethylsilyl, tert-butyldiphenylsilyl, or triethylsilyl;
- $PG^2$ is benzyl; and
- LG is ethylthio, p-tolylthio, phenylthio, bromine, fluorine, trichloroacetimidate, N-phenyl trifluoroacetimidate or dibutyl phosphate, B: azide group reduction and acetylation to provide trisaccharide 23;

H: removal of Troc and modification to acetamidine; and

I: hydrogenation global deprotection.

7. A method of preparing the linked oligosaccharide of Formula II-b according to claim 1 which comprises:
providing a monosaccharide building block 3 is used as starting material for synthesis of 2,3-diamido-D-glucuronic acid in an oligosaccharide chain, wherein:
the monosaccharide building block 3 is expressed as Formula VI-3:

- $PG^5$ is trichloroacetyl, dichloroacetyl or chloroacetyl;
- $PG^6$ is benzyl, 2-naphthylmethyl, p-methoxybenzyl or levulinyl;
- $PG^7$ is benzyl; and
- LG is ethylthio, p-tolylthio, phenylthio, bromine, fluorine, trichloroacetimidate, N-phenyl trifluoroacetimidate or dibutyl phosphate, and performing chemical synthesis steps A, B, C, G, J, K, and I in the following order:

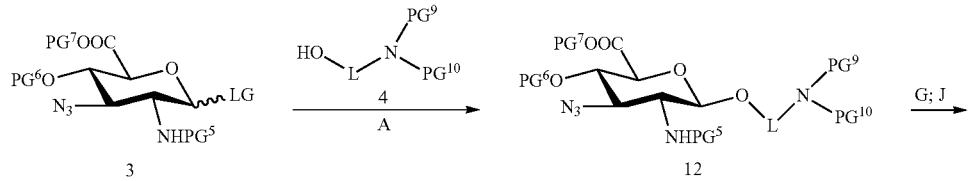

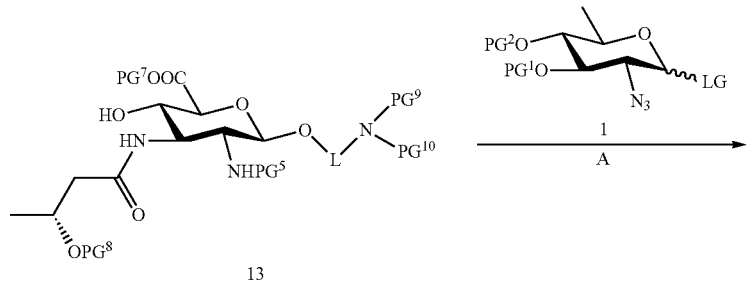

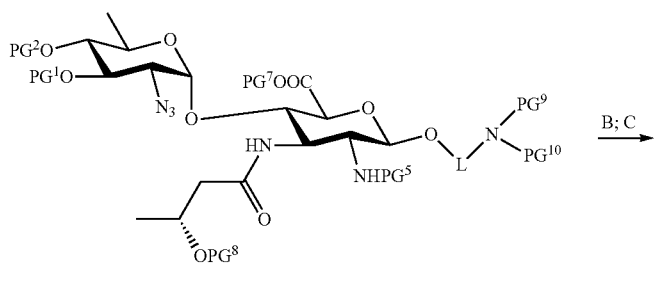

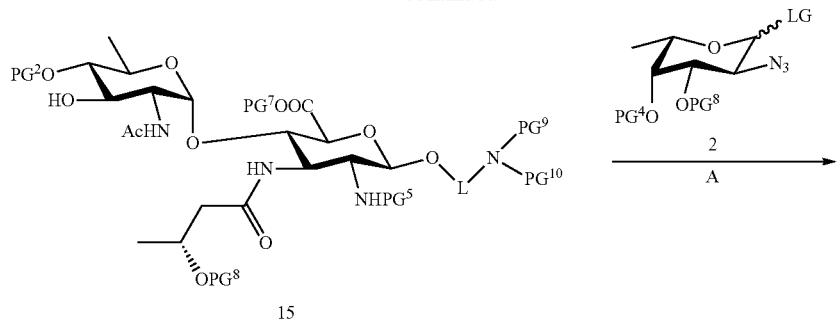
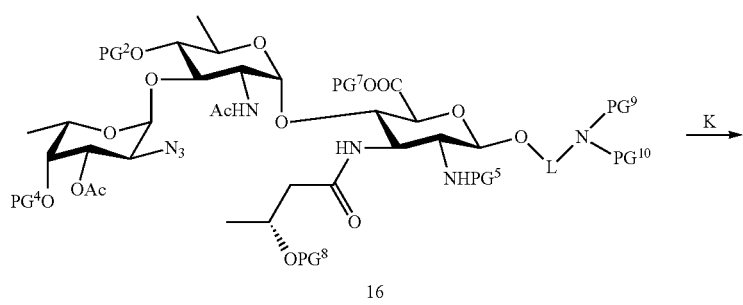
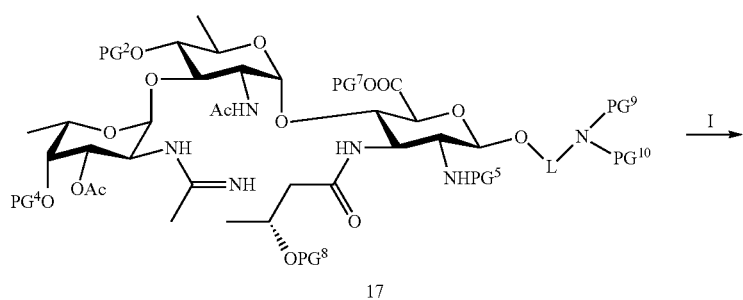
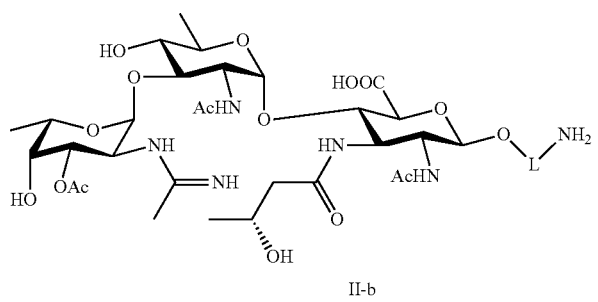

wherein steps A, B, C, G, I, J, and K, are the following:
A: glycosylation of the monosaccharide building block 3;
G: azido reduction and butyrylation;
J: glucuronic acid 4-position deprotection to obtain monosaccharide acceptor 13, followed by glycosylation of monosaccharide acceptor 13 with monosaccharide building block 1 to obtain disaccharide 14,
wherein:
the monosaccharide building block 1 is expressed as Formula VI-1:

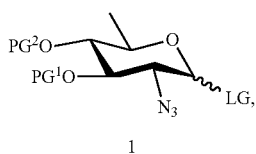

VI-1

1

PG$^1$ is acetyl, levulinyl, benzoyl, chloroacetyl, dichloroacetyl, trichloroacetyl, pivaloyl, allyloxycarbonyl, 2-naphthylmethyl, p-methoxybenzyl, tert-butyldimethylsilyl, tert-butyldiphenylsilyl, or triethylsilyl;
PG$^2$ is benzyl; and
LG is ethylthio, p-tolylthio, phenylthio, bromine, fluorine, trichloroacetimidate, N-phenyl trifluoroacetimidate or dibutyl phosphate,
B: azide group reduction and acetylation;

C: 3-position deprotection to obtain disaccharide acceptor 15, followed by glycosylation of the disaccharide acceptor 15 with monosaccharide building block 2 to obtain trisaccharide 16,
wherein:
the monosaccharide building block 2 is expressed as Formula VI-2:

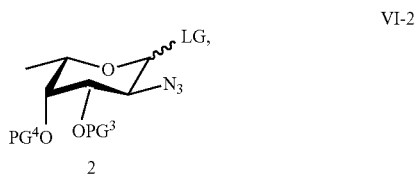

2

PG$^3$ and PG$^4$ are acetyl, levulinyl, benzoyl, chloroacetyl, dichloroacetyl, trichloroacetyl, pivaloyl, allyloxycarbonyl, 2-naphthylmethyl, p-methoxybenzyl, tert-butyldimethylsilyl, tert-butyldiphenylsilyl, or triethylsilyl; and
LG is ethylthio, p-tolylthio, phenylthio, bromine, fluorine, trichloroacetimidate, N-phenyl trifluoroacetimidate or dibutyl phosphate
K: azido reduction and modification to acetamidine; and
I: hydrogenation global deprotection.

8. The method according to claim 7, for preparing a linked oligosaccharide of Formula III-a:

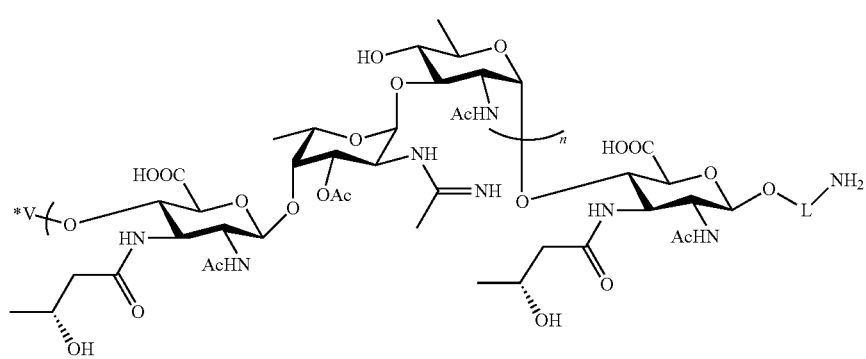

III-a which comprises:
providing the trisaccharide 16 as a starting material; and
performing chemical synthesis steps D, E, F, G, H, and I, in the following order:

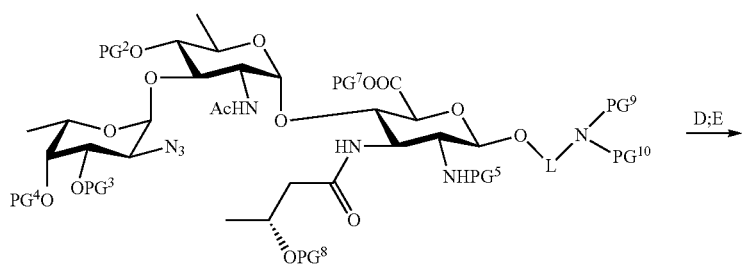

16

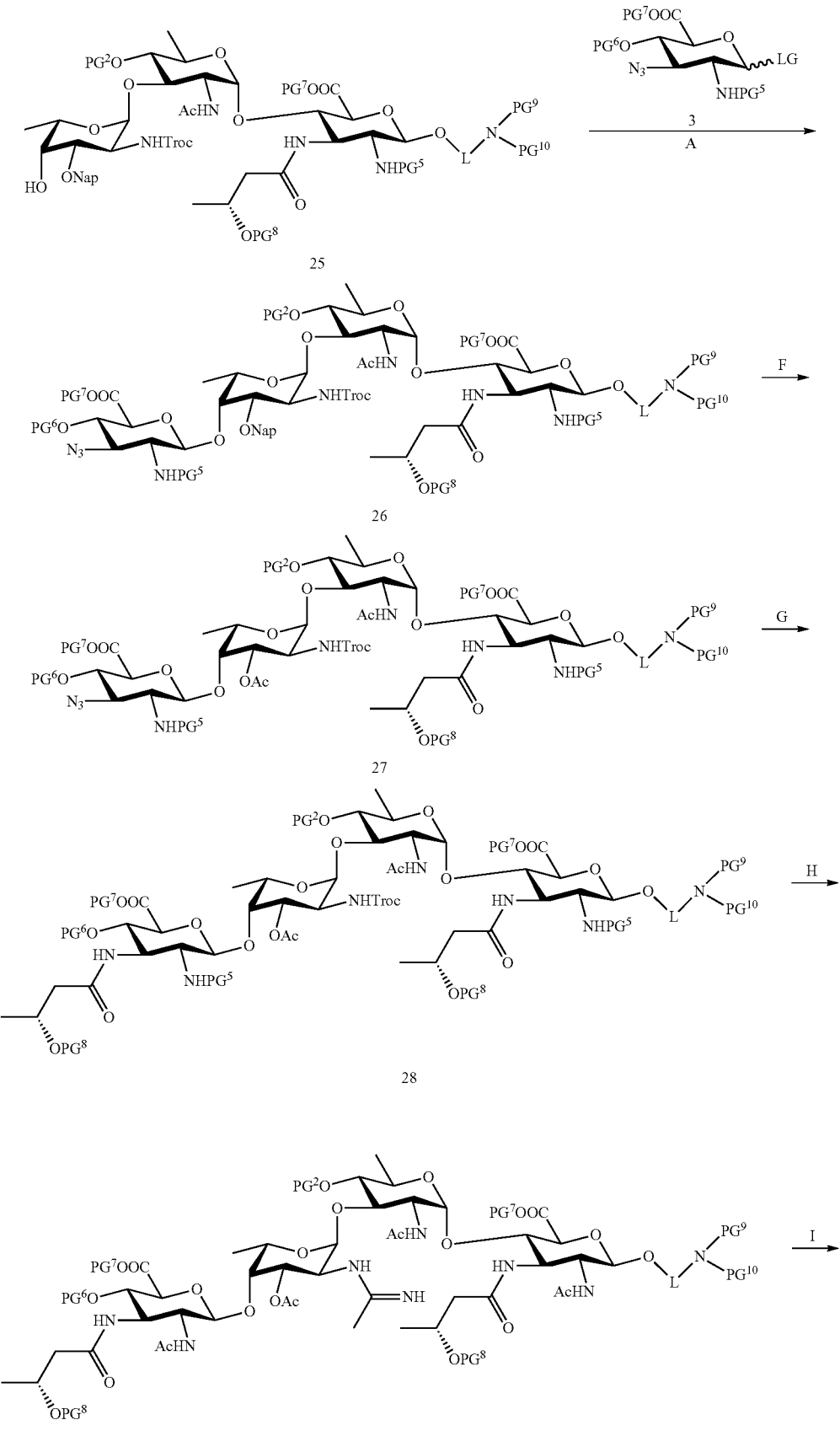

-continued
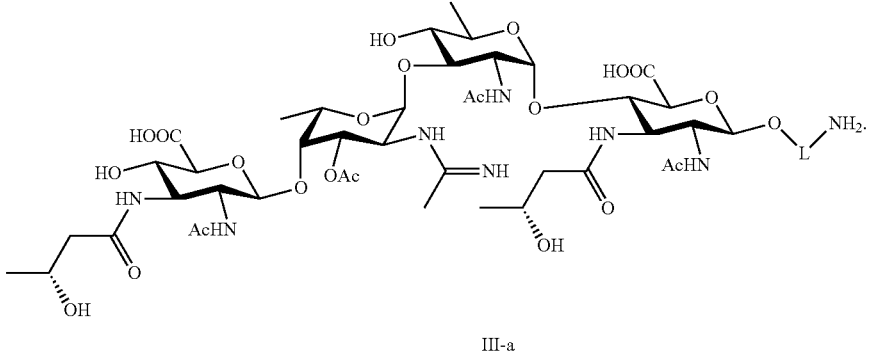
III-a
9. The method according to claim 6, for preparing a linked oligosaccharide of Formula III-b:
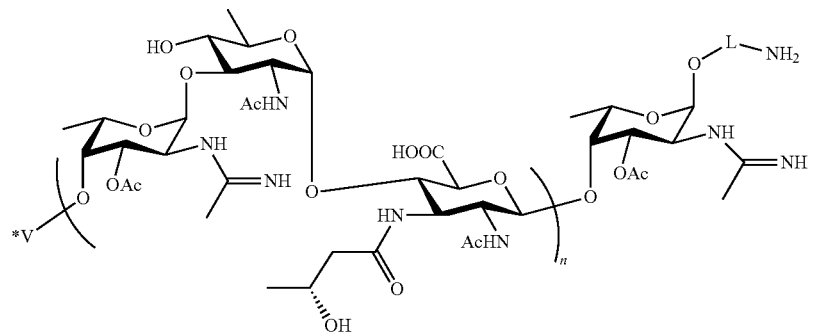
III-b
which comprises:
  providing the trisaccharide 23 as a starting material; and
  performing chemical synthesis steps A, C, D, H, and I,
    in the following order:
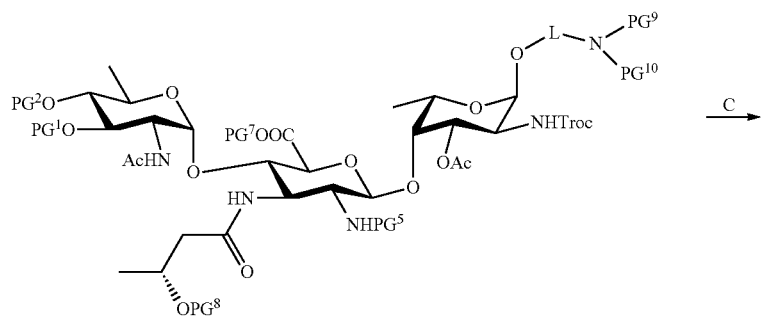
23

-continued

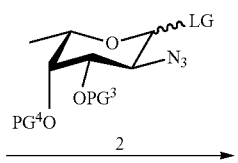
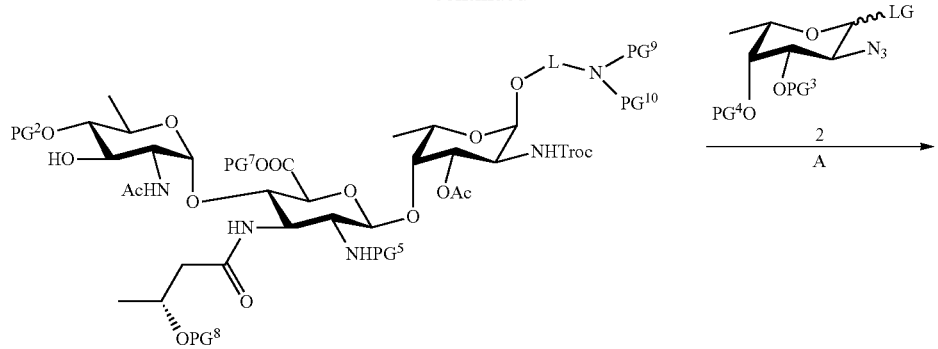

30

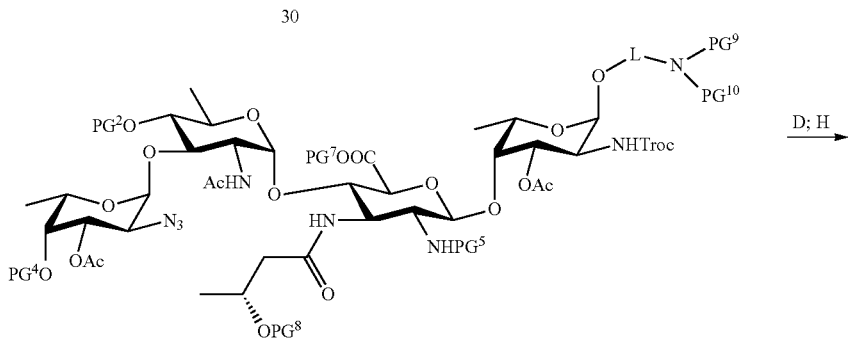

31

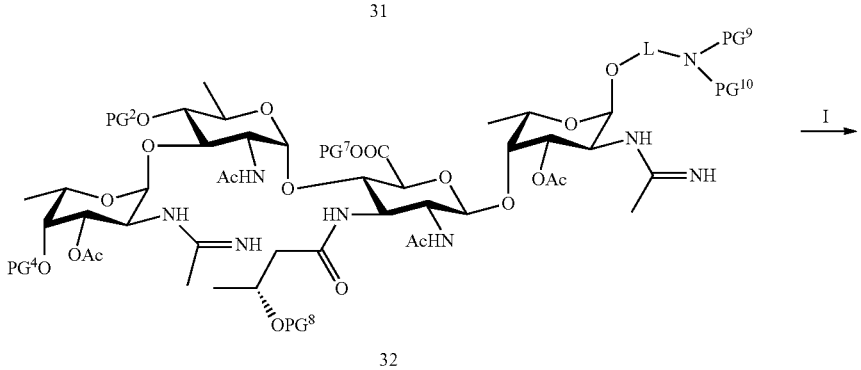

32

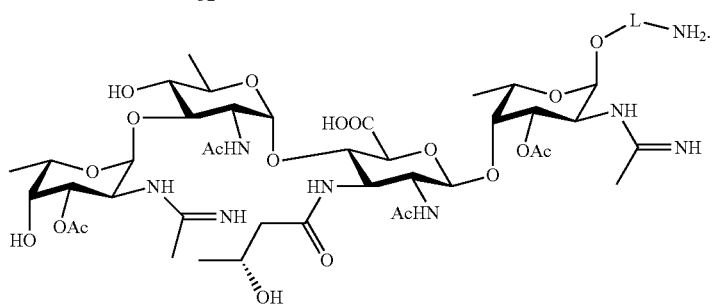

III-b

10. The method according to claim 5, further comprises preparing important intermediate 3-azidoglycosamine for the monosaccharide building block 3, and wherein when performing double inversion at 3-position,
   1) 3-trifluoromethanesulfonyl glucosamine is subjected to the Lattrell-Dax reaction to obtain 3-hydroxyl allosamine;
   2) the 3-hydroxyl allosamine is subjected to trifluoromethanesulfonylation to obtain 3-trifluoromethanesulfonyl allosamine; and
   3) the 3-trifluoromethanesulfonyl allosamine is subjected to azido nucleophilic substitution to obtain the 3-azidoglycosamine.

11. A *Plesiomonas shigelloides* vaccine, comprising:
the linked oligosaccharide chain fragment of the *Plesiomonas shigelloides* serotype O51 O-antigen polysaccharide according to claim 1, which the linked oligosaccharide chain fragment of the *Plesiomonas shigelloides* serotype O51 O-antigen polysaccharide according to claim 2, which serves as the epitope; or the linked oligosaccharide chain fragment of the *Plesiomonas shigelloides* serotype O51 O-antigen polysaccharide according to claim 3, which serves as the epitope; or the linked oligosaccharide chain fragment of the *Plesiomonas shigelloides* serotype O51 O-antigen polysaccharide according to claim 4, which serves as the epitope.

12. The method according to claim 5, for preparing a linked oligosaccharide of Formula III-c:

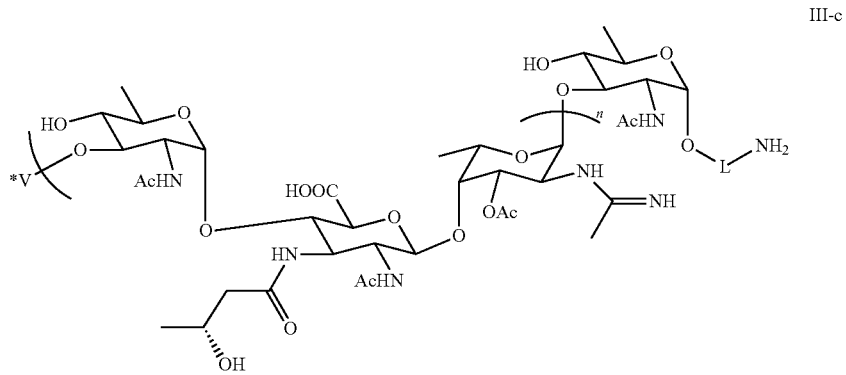

which comprises:
providing the trisaccharide 10 as the starting material; and
performing chemical synthesis steps A, B H, J, and I, in the following order:

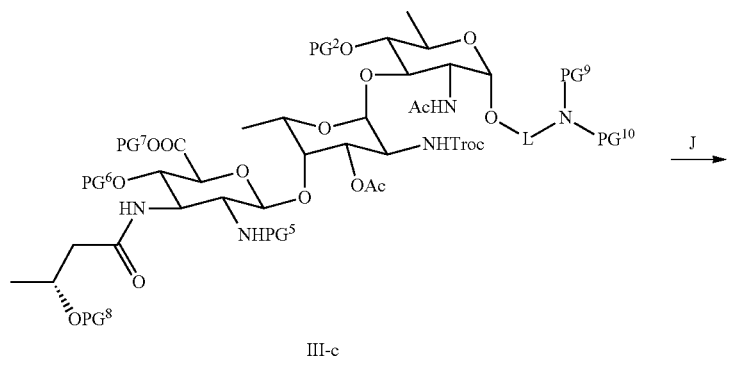

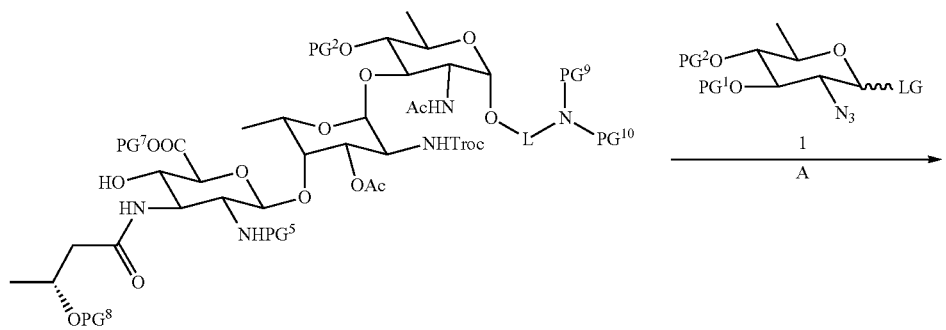

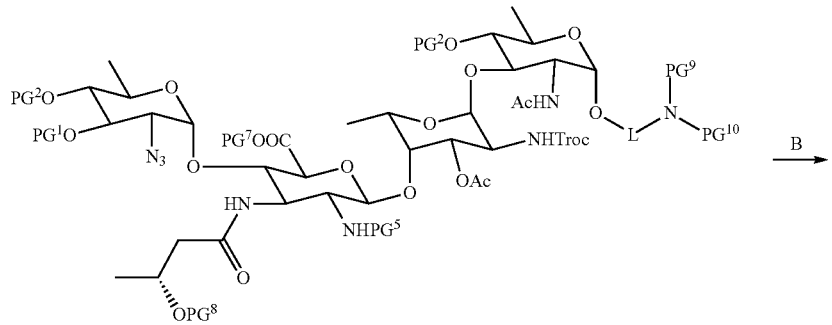
34
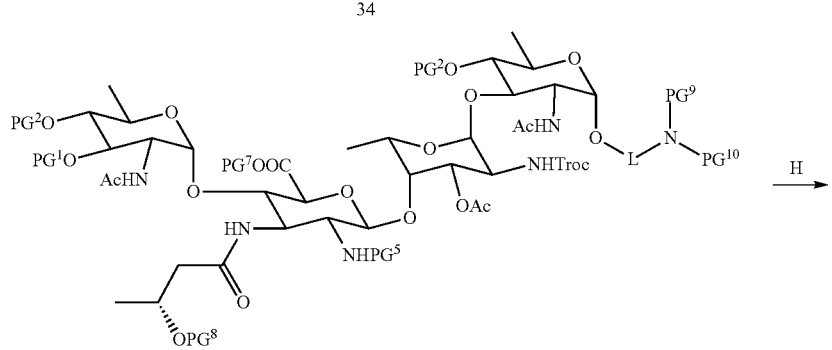
35
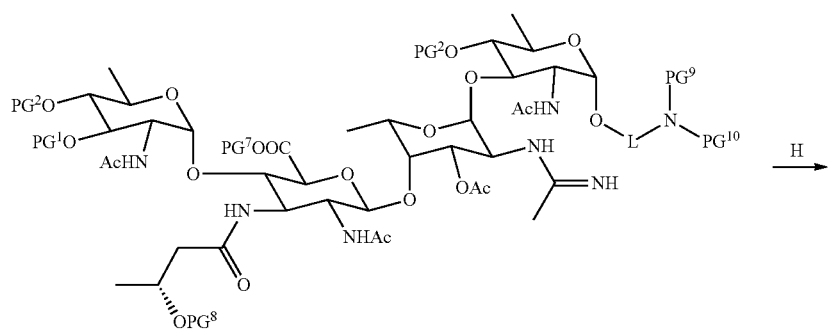
36
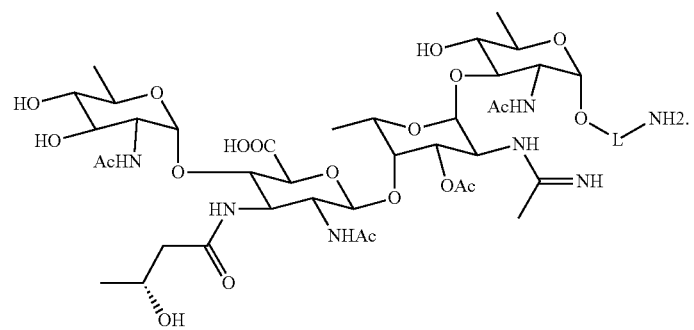
III-c

13. The method according to claim 9, for preparing a linked oligosaccharide of Formula IV-a:
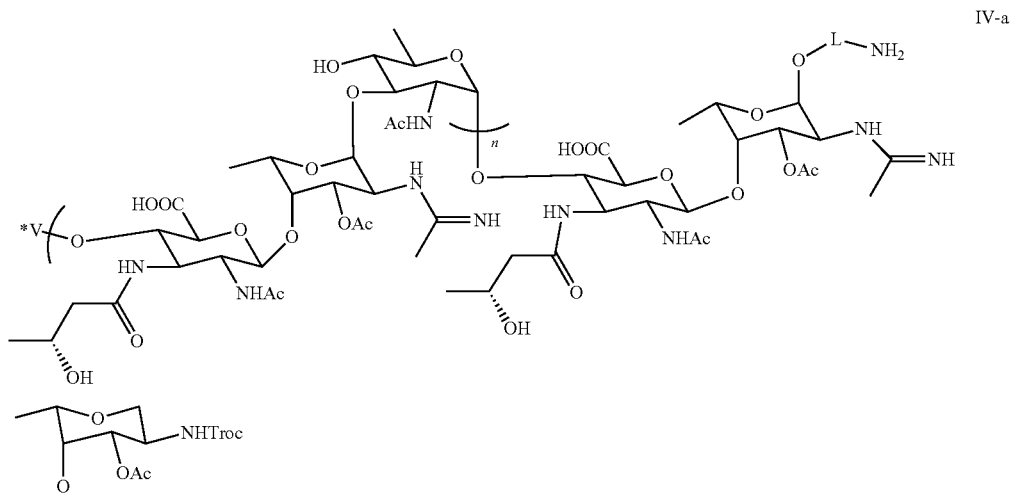
which comprises:
  providing tetrasaccharide 31 as the starting material; and
  performing chemical synthesis steps A, D, E, F, G, H, and I, in the following order:
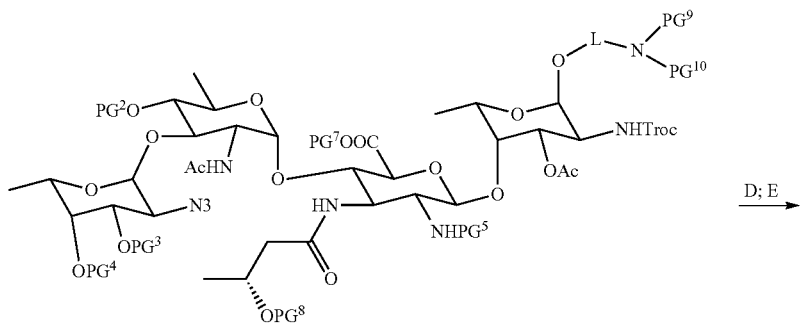
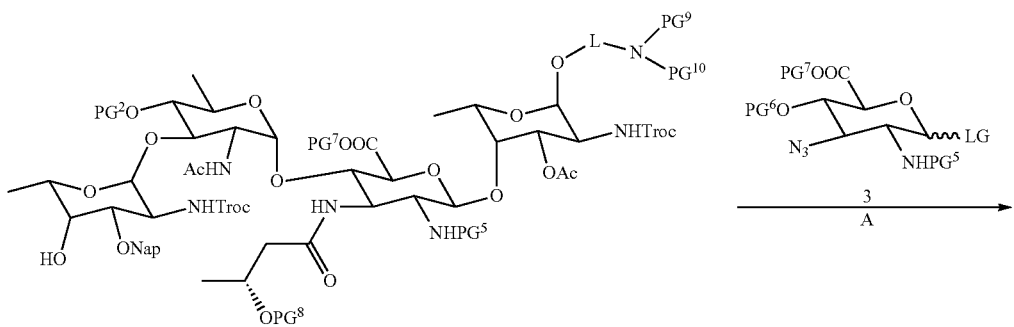

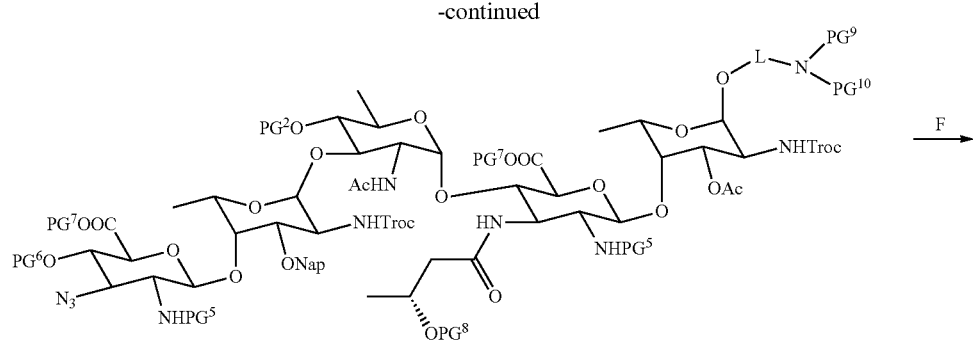
38
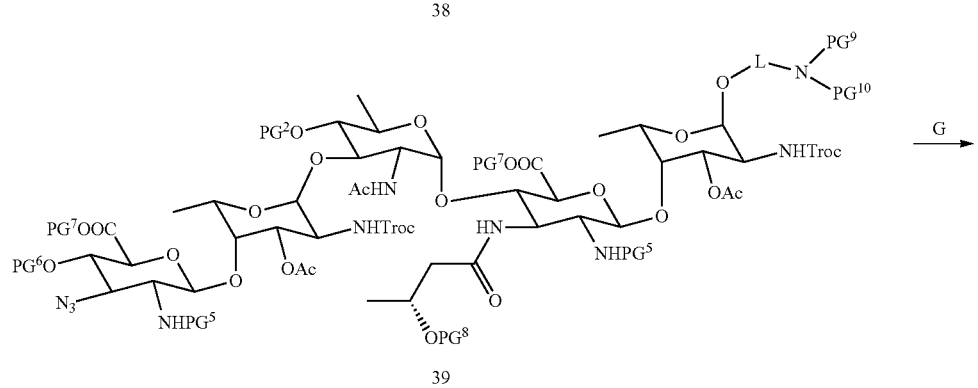
39
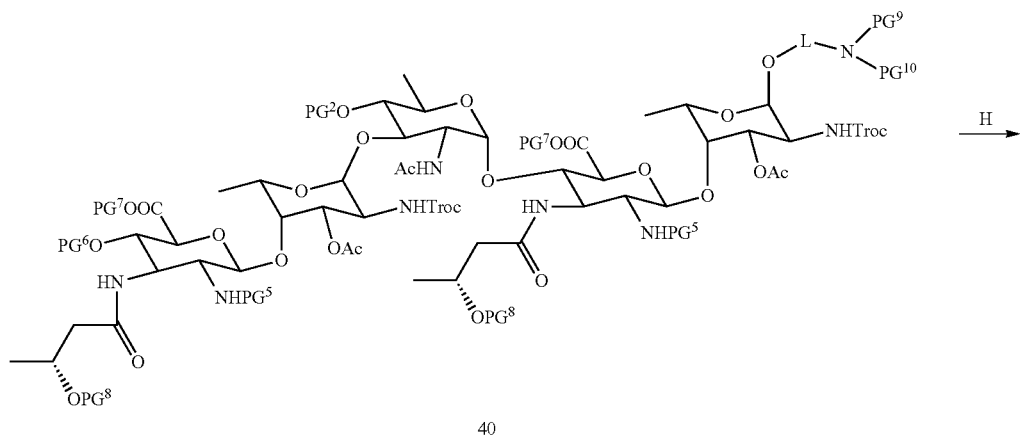
40
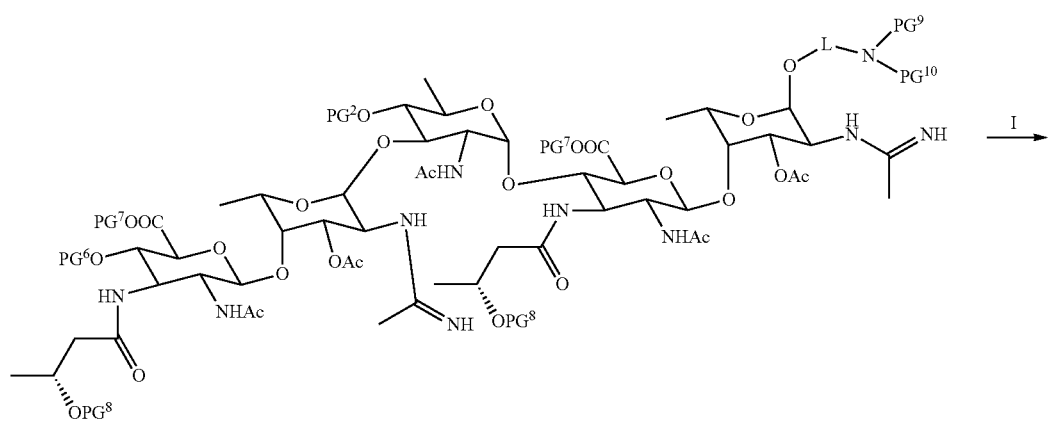
41

-continued
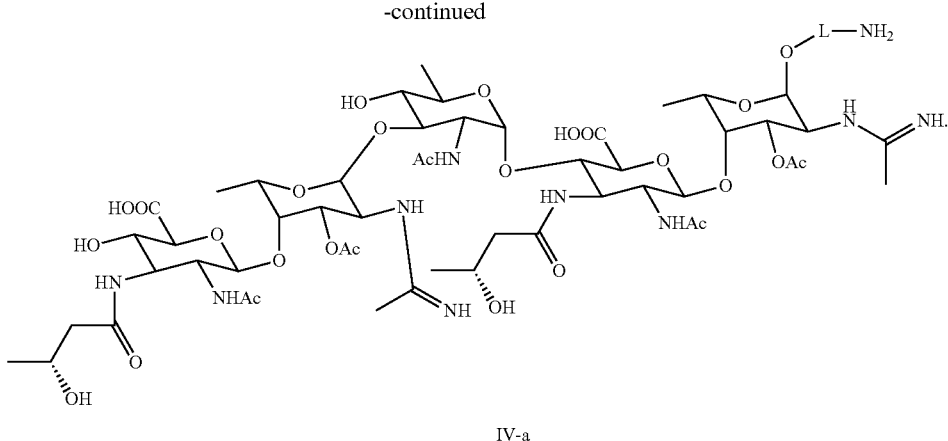
IV-a
14. The method according to claim 10, for preparing a linked oligosaccharide of Formula IV-b:
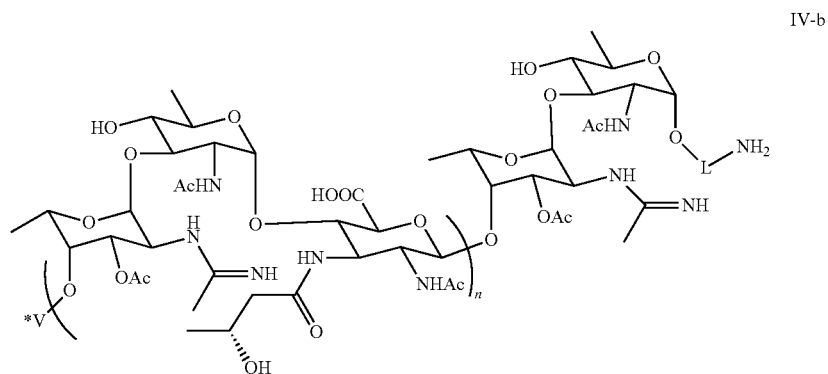
IV-b
which comprises:
   providing the trisaccharide 35 as the starting material; and
   performing chemical synthesis steps A, C, D, H, and I, in the following order:
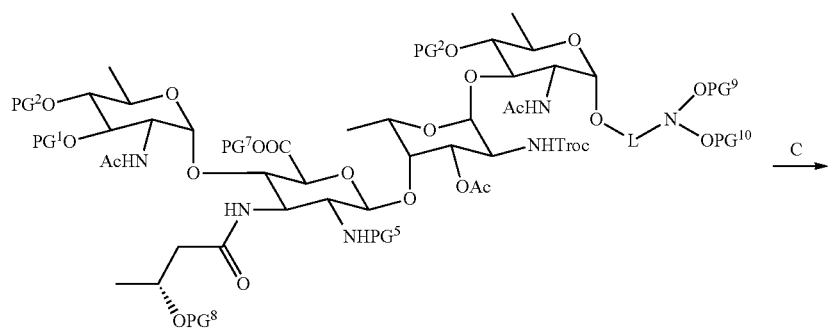
35

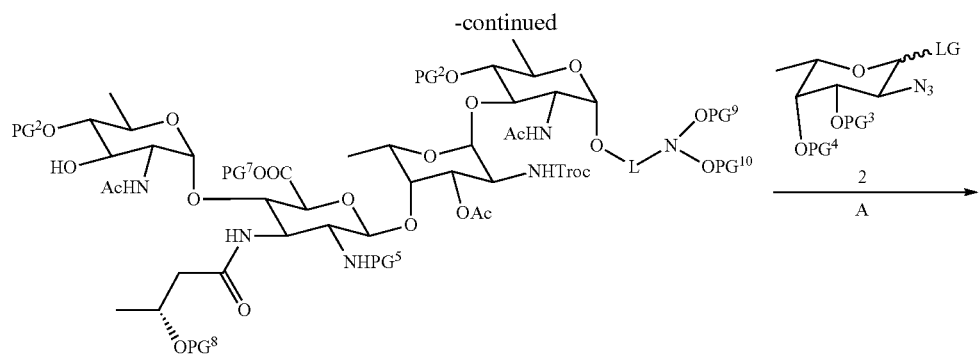
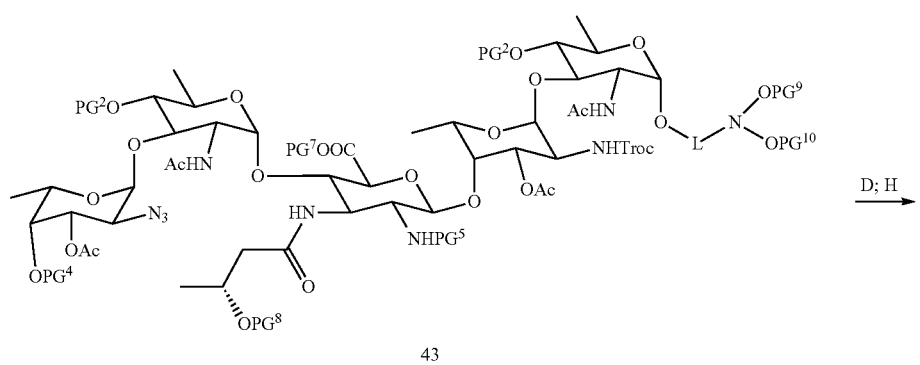
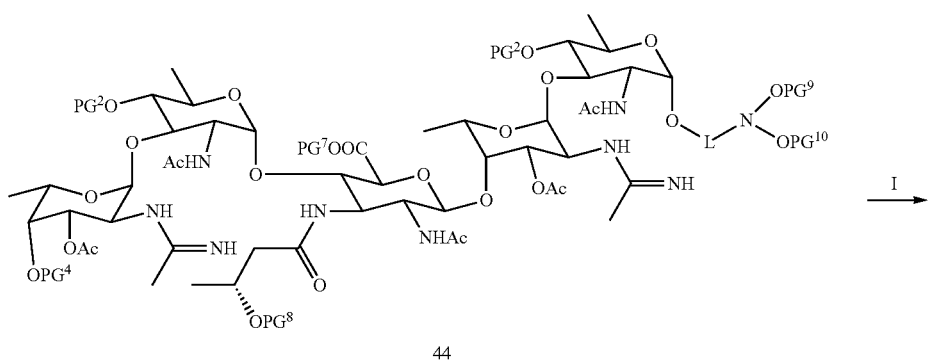
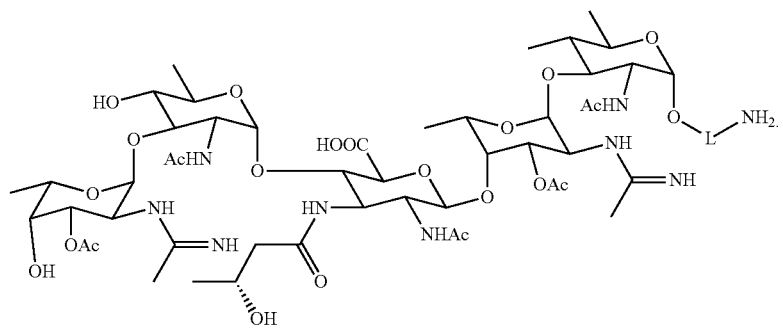

15. The method according to claim 9, for preparing a linked oligosaccharide of Formula IV-c:
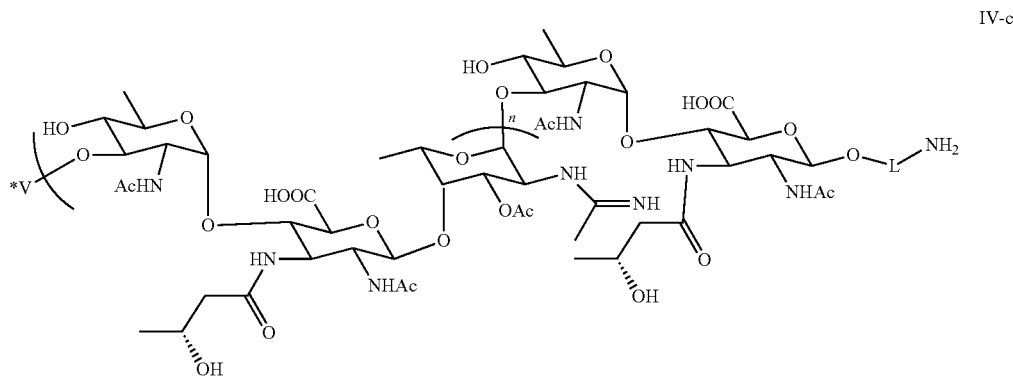
IV-c
which comprises:
   providing trisaccharide 28 as the starting material; and
   performing chemical synthesis steps A, B J, H, and I, in the following order:
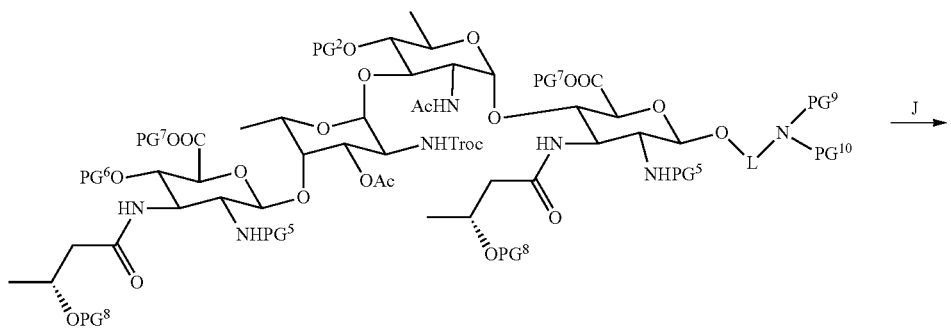
28
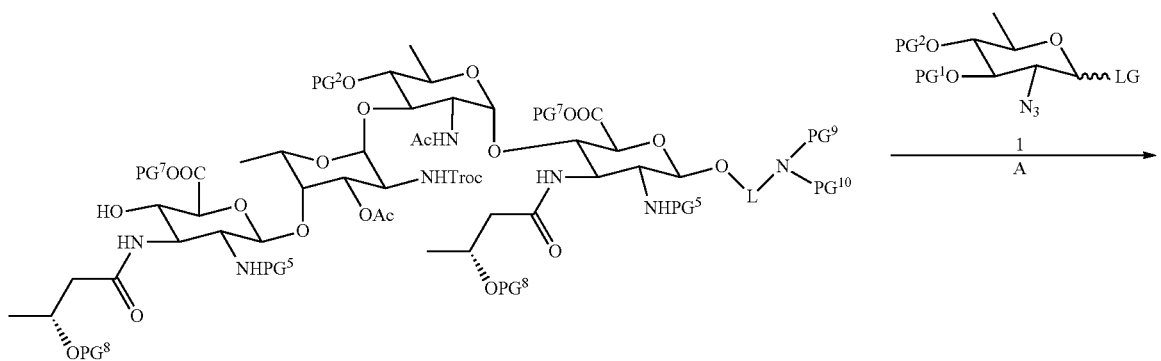
45